US010414809B2

(12) United States Patent
Shen et al.

(10) Patent No.: US 10,414,809 B2
(45) Date of Patent: Sep. 17, 2019

(54) ANIMAL MODEL OF LONGEVITY AND RELATED METHODS FOR INCREASING LONGEVITY AND INHIBITING TUMORIGENESIS

(71) Applicant: ACADEMIA SINICA, Taipei (TW)

(72) Inventors: Che-Kun James Shen, Taipei (TW); Yu-Chiau Shyu, Taichung (TW)

(73) Assignee: Academia Sinica, Taipei (TW)

( * ) Notice: Subject to any disclaimer, the term of this patent is extended or adjusted under 35 U.S.C. 154(b) by 102 days.

(21) Appl. No.: 15/507,650

(22) PCT Filed: Sep. 1, 2015

(86) PCT No.: PCT/US2015/047917
§ 371 (c)(1),
(2) Date: Feb. 28, 2017

(87) PCT Pub. No.: WO2016/036727
PCT Pub. Date: Mar. 10, 2016

(65) Prior Publication Data
US 2017/0283477 A1    Oct. 5, 2017

Related U.S. Application Data

(60) Provisional application No. 62/044,411, filed on Sep. 1, 2014.

(51) Int. Cl.
| | |
|---|---|
| *C07K 14/47* | (2006.01) |
| *A01K 67/027* | (2006.01) |
| *A61K 38/17* | (2006.01) |
| *A61K 45/06* | (2006.01) |

(52) U.S. Cl.
CPC ...... *C07K 14/4702* (2013.01); *A01K 67/0275* (2013.01); *A61K 38/1709* (2013.01); *A61K 45/06* (2013.01); *C07K 14/4703* (2013.01); *A01K 2217/05* (2013.01); *A01K 2227/105* (2013.01); *A01K 2267/0331* (2013.01); *Y02A 50/402* (2018.01)

(58) Field of Classification Search
None
See application file for complete search history.

(56) References Cited

U.S. PATENT DOCUMENTS

2002/0042138 A1    4/2002   Townes et al.

OTHER PUBLICATIONS

Siatecka et al, MCB 27:8547-60, 2007 (Year: 2007), IDS #1, filed on Apr. 10, 2017.*
Siatecka et al., "Sumoylation of EKLF promotes transcriptional repression and is involved in inhibition of megakaryopoiesis", Molecular and Cellular Biology, Dec. 2007, pp. 8547-8560.
Anderson et al., "The GATA-E box-GATA motif in the EKLF promoter is required for in vivo expression", Blood, Mar. 1, 2000, vol. 95, No. 5, pp. 1652-1655.
Tsai et al., "Knock-in Mutation of Transcription Factor GATA-3 into the GATA-1 Locus: Partial Rescue of GATA-1 Loss of Function in Erythroid Cells", Developmental Biology, 1998, 196, pp. 218-227.

* cited by examiner

*Primary Examiner* — Lei Yao
(74) *Attorney, Agent, or Firm* — Muncy, Geissler, Olds & Lowe, P.C.

(57) ABSTRACT

The present invention includes a genetically-modified non-human animal model of longevity and increased health span, which is associated with reduced tumorigenesis and tumor metastasis, as well as related methods for increasing longevity and health span, reducing tumorigenesis and tumor metastasis, and identifying active agents that confer increased longevity or health span, or reduced tumorigenesis or tumor metastasis.

5 Claims, 17 Drawing Sheets
Specification includes a Sequence Listing.

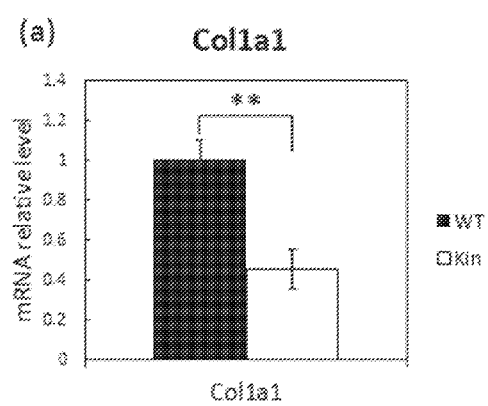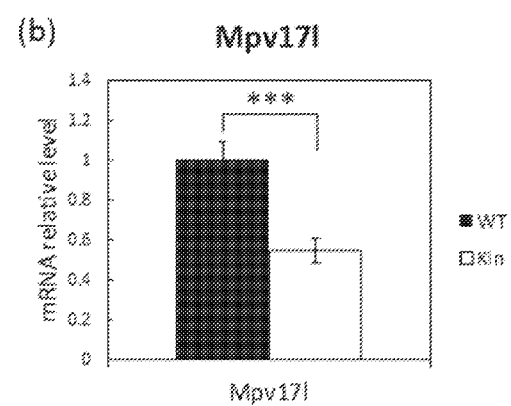
FIG. 2A                    FIG. 2B

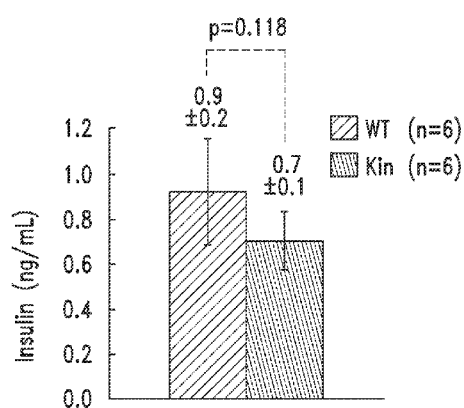 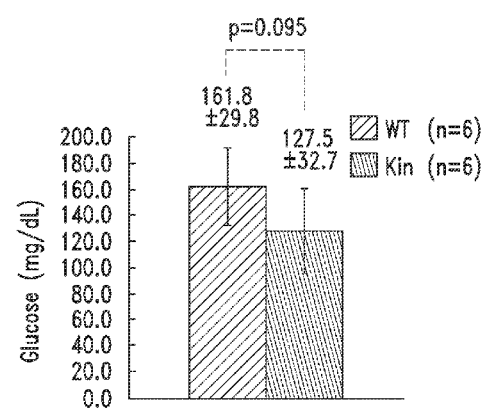
*FIG. 6A*  *FIG. 6B*

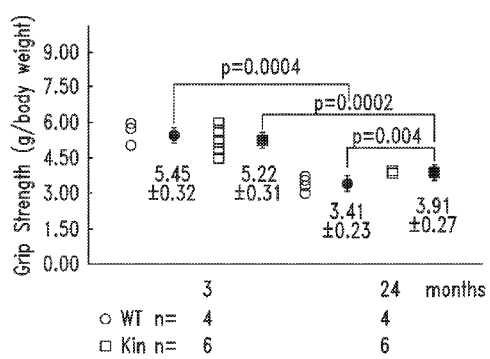
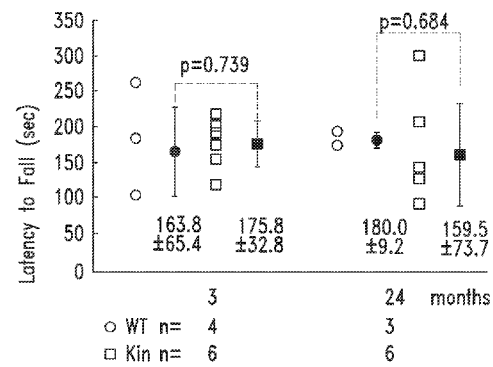
FIG. 7A
FIG. 7B

| Genotype | Presence of Tumor |
|---|---|
| WT 1 | Liver, Pancreas, Spleen |
| WT 2 | Liver |
| WT 3 | No |
| Kin 1 | No |
| Kin 2 | No |
| Kin 3 | No |

ANIMAL MODEL OF LONGEVITY AND RELATED METHODS FOR INCREASING LONGEVITY AND INHIBITING TUMORIGENESIS

CROSS REFERENCE TO RELATED APPLICATIONS

This application claims priority to U.S. Provisional Application No. 62/044,411, filed on Sep. 1, 2014, which is incorporated by reference herein in its entirety.

FIELD OF THE INVENTION

The present invention relates to methods for enhancing life span, increasing health span, and inhibiting tumorigenesis and tumor metastasis, as well as novel non-human animal models of longevity and tumorigenesis, and methods of identifying therapeutic agents for use in enhancing life span or health span, or for use in inhibiting tumorigenesis or tumor metastasis.

BACKGROUND OF THE INVENTION

Longevity genes are of obvious interest and importance, both for their life-extension potential and the possibility of their contributing to the enhancement of the quality of life. However, very few of these genes have been identified and even less is understood about how these genes act to prevent aging and promote life extension. In addition, there is a related need in the art for identifying genes associated with decreased risk of cellular proliferative disorders, including those associated with aging.

Accordingly, there exists the need to discover genes whose function is associated with life-extension and/or reduction of cellular proliferative disorders. These genes and their products would be useful in the screening for anti-aging and/or anti-cancer agents and would serve as key targets in various anti-aging and anti-cancer therapies. In addition, knowledge of these genes allows the development of animal models of disease, which can be used to further identify and study disease pathways, and identify and validate therapeutic agents. Ultimately, such tools and therapeutic agents could help to alleviate cognitive and motor function deficits in the aged population, and reduce the incidence or metastasis of cancer in both the aged and the general population, thereby prolong the independence of the elderly and enhancing health.

BRIEF SUMMARY OF THE INVENTION

A first aspect of the present invention provides a non-human transgenic animal comprising one or more modified Erythroid Kruppel-like factor (EKLF) gene alleles encoding a modified EKLF polypeptide comprising one or more amino acid modifications as compared to a wild-type EKLF polypeptide. In certain embodiments, the wild-type EKLF polypeptide is from the same genus or species of animal as the non-human transgenic animal. In particular embodiments, the non-human transgenic animal is a knock-in animal. In certain embodiments, one or more endogenous EKLF gene alleles of the animal are replaced by the one or more modified EKLF genes. In particular embodiments, the expression of the one or more modified EKLF gene alleles is under the control of an endogenous EKLF promoter. In certain embodiments, both endogenous EKLF gene alleles are replaced by the modified EKLF genes. In one embodiment, the non-human transgenic animal is a knock-in animal wherein both alleles of the EKLF gene are modified as compared to the wild-type, such that they encode a modified EKLF polypeptide described herein, e.g., a modified EKLF polypeptide comprising a mutated sumoylation site that is not sumoylated. In certain embodiments, the animal is a rodent, optionally a mouse or a rat.

In particular embodiments of the first aspect of the present invention, the one or more amino acid modifications comprise a modification at an amino acid position that is sumoylated or phosphorylated in the wild-type EKLF polypeptide. In one embodiment, the one or more amino acid modification comprises a modification of an amino acid corresponding to position 74 of the full length wild-type mouse EKLF polypeptide. In certain embodiments related to animals other than mice, the one or more amino acid modification comprises a modification of a sumoylated amino acid residue corresponding to this residue in the mouse EKLF polypeptide, but it may be located at a different position. For example, in the human EKLF polypeptide, the sumoylation site corresponding to position 74 in the mouse EKLF polypeptide is located at amino acid residue 54. In particular embodiments, it is a Lys residue. In certain embodiments, the modification of the amino acid corresponding to position 74 is a substitution of Lys with Arg (K74R). In particular embodiments, the one or more amino acid modification comprises a modification of an amino acid corresponding to position 68 of the full length wild-type mouse EKLF polypeptide. In one embodiment, the present invention includes a homozygous knock-in mouse comprising the amino acid substitution K74R in both EKLF gene alleles. In certain embodiments related to animals other than mice, the one or more amino acid modification comprises a modification of a phosphorylated amino acid residue, e.g., an amino acid residue corresponding to this residue in the mouse EKLF polypeptide, but it may be located at a different position.

In certain embodiments of first, second, third or fourth aspects of the present invention, the modified EKLF polypeptide has reduced sumoylation or reduced phosphorylation as compared to the wild-type EKLF polypeptide. In certain embodiments, the modified EKLF polypeptide has reduced translocation from the cytoplasm to the nucleus as compared to the wild-type EKLF polypeptide, and/or a modified transactivator activity or a modified repressor activity as compared to the wild-type EKLF polypeptide. In related embodiments, the presence or expression of the modified EKLF polypeptide is associated with an increased lifespan or increased health span of the non-human transgenic animal, or the expression of the modified EKLF polypeptide is associated with reduced tumor occurrence, tumor growth or reduced tumor metastasis in the non-human transgenic animal, as compared to wild-type animals.

In a second aspect, the present invention includes a knock-in vector comprising a polynucleotide sequence encoding a modified EKLF polypeptide, or a portion thereof, comprising one or more amino acid modifications as compared to a wild-type EKLF polypeptide.

In a related third aspect, the present invention includes a cell, tissue or organ derived from a non-human transgenic animal described herein.

In a fourth aspect, the present invention provides a method of treating or preventing a cellular proliferative disorder, or inhibiting or reducing the incidence of tumor occurrence or metastasis, in a subject in need thereof, comprising administering to the subject an effective amount of: a polypeptide or a nucleic acid encoding the polypeptide, wherein the polypeptide is a modified EKLF polypeptide comprising one or more amino acid modifications that confer decreased sumoylation of the modified EKLF polypeptide as compared to a wild-type EKLF polypeptide; and/or a first active agent that alters one or more activities of an endogenous or wild-type EKLF polypeptide. In certain embodiments, the modified EKLF polypeptide is a modified human EKLF polypeptide, and in certain embodiments, the first active agent alters one or more activities of a wild-type human EKLF polypeptide. In some embodiments, the cellular proliferative disorder is a tumor or a tumor metastasis, such as but not limited to, a liver cancer, a colon cancer, a breast cancer, a prostate cancer, a hepatocellular carcinoma, a melanoma, a lung cancer, a glioblastoma, a brain tumor, a hematopoetic malignancy, a cholangiocarcinoma, a retinoblastoma, a renal cell carcinoma, a head and neck cancer, a cervical cancer, a pancreatic cancer, an esophageal cancer, or a squamous cell carcinoma.

In particular embodiments of the fourth aspect wherein the polypeptide or the nucleic acid is administered, the modified EKLF polypeptide has reduced translocation from the cytoplasm to the nucleus as compared to the wild-type EKLF polypeptide. In certain embodiments, the modified EKLF polypeptide has a modified transactivator activity or a modified repressor activity as compared to the wild-type EKLF polypeptide. In one embodiment, the nucleic acid is an expression vector. In one embodiment, the expression vector is a viral vector. In particular embodiments, the viral vector is derived from a herpes virus, a retrovirus, a vaccinia virus, an attenuated vaccinia virus, a canary pox virus, an adenovirus, or an adeno-associated virus.

In particular embodiments of the fourth aspect of the present invention, the one or more amino acid modifications comprises a modification at an amino acid position that is sumoylated or phosphorylated in the wild-type EKLF polypeptide, e.g., the wild-type human EKLF polypeptide. In certain embodiments, the one or more amino acid modifications comprises a modification of an amino acid corresponding to position 54 of the full length wild-type human EKLF polypeptide. In one embodiment, the modification of the amino acid at position 54 is a substitution of Lys, e.g., with Arg (K54R). In certain embodiments, the one or more amino acid modifications comprises a modification of an amino acid that is phosphorylated, e.g., in the human EKLF polypeptide, such as, but not limited to, a phosphorylated amino acid corresponding to position 68 of the full length wild-type mouse EKLF polypeptide.

In particular embodiments of the fourth aspect where the first active agent is administered, the first active agent reduces translocation of the endogenous EKLF polypeptide from the cytoplasm to the nucleus. In certain embodiments, the first active agent modifies a transactivator activity or modifies a repressor activity of the endogenous EKLF polypeptide. In some embodiments, the first active agent binds to the endogenous EKLF polypeptide. In various embodiments, the first active agent is a small organic molecule or a polypeptide, optionally an antibody or a functional fragment thereof. In certain embodiments, binding of the first active agent to the endogenous EKLF polypeptide inhibits its translocation from the cytoplasm to the nucleus.

In certain embodiments of the fourth aspect wherein the polypeptide or the nucleic acid is administered, or wherein the first active agent is administered, the method further comprises administering a second active agent that inhibits expression of the endogenous EKLF polypeptide. In particular embodiments, the second active agent is a nucleic acid molecule, optionally an antisense RNA, siRNA, shRNA or miRNA that binds an mRNA encodes the endogenous EKLF polypeptide or a complement thereof that. In one embodiment, the EKLF cDNA or mRNA sequence is the human sequence provided in GenBank Acession No. BC033580.1.

Certain embodiments of the fourth aspect of the present invention further comprise administering to the subject an effective amount of an anti-proliferation agent suitable for treating the cellular proliferative disorder. In particular embodiments, the anti-proliferation agent is an alkylating agent, a topoisomerase inhibitor, an anti-metabolite, or a cytotoxicity antibiotic. In certain embodiments, the alkylating agent is cisplatin, carboplatin, oxaliplatin, mechlorethamine, cyclophosphamide, melphalan, chlorambucil, ifosfamide, busulfan, N-nitroso-N-methylurea (MNU), carmustine, lomustine, semustine, fotemustine, streptozotocin, dacarbazine, mitozolomide, temozolomide, thiotepa, mytomycin, or diaziquone. In particular embodiments, the topoisomerase inhibitor is camptothecin, irinotecan, topotecan, etoposide, doxorubicin, teniposide, novobiocin, merbarone, or aclarubicin. In certain embodiments, the anti-metabolite is fluoropymidine, deoxynucleoside analogue, thiopurine, methotrexate, or pemetrexed. In particular embodiments, the cytotoxicity antibiotic is actinomycin, bleomycin, plicamycin, mitomycin, doxorubicin, daunorubicin, epirubicin, idarubicin, piraubicin, alcarubicin, or mitoxantrone.

In a fifth aspect, the present invention includes a method of extending the lifespan or health span of a subject, comprising administering to the subject an effective amount of: a polypeptide or a nucleic acid encoding the polypeptide, wherein the polypeptide is a modified EKLF polypeptide comprising one or more amino acid modifications that confer reduced sumoylation of the modified EKLF polypeptide as compared to a wild-type EKLF polypeptide; and/or a first active agent that alters one or more activities of an endogenous EKLF polypeptide. In certain embodiments, the modified EKLF polypeptide is a modified human EKLF polypeptide, and in certain embodiments, the first active agent alters one or more activities of a wild-type human EKLF polypeptide.

In particular embodiments of the fifth aspect wherein the polypeptide or the nucleic acid is administered, the modified EKLF polypeptide has reduced translocation from the cytoplasm to the nucleus as compared to the wild-type EKLF polypeptide. In certain embodiments, the modified EKLF polypeptide has a modified transactivator activity or a modified repressor activity as compared to the wild-type EKLF polypeptide. In one embodiment, the nucleic acid is an expression vector. In one embodiment, the expression vector is a viral vector. In particular embodiments, the viral vector is derived from a herpes virus, a retrovirus, a vaccinia virus, an attenuated vaccinia virus, a canary pox virus, an adenovirus, or an adeno-associated virus.

In particular embodiments of the fifth aspect of the present invention, the one or more amino acid modifications comprises a modification at an amino acid position that is sumoylated or phosphorylated in the wild-type EKLF polypeptide, e.g., the wild-type human EKLF polypeptide. In certain embodiments, the one or more amino acid modifications comprises a modification of an amino acid corresponding to position 54 of the full length wild-type human EKLF polypeptide. In one embodiment, the modification of the amino acid at position 54 is a substitution of Lys, e.g., with Arg (K54R). In certain embodiments, the one or more amino acid modifications comprises a modification of an amino acid that is phosphorylated, e.g., in the human EKLF polypeptide, such as, but not limited to, a phosphorylated amino acid corresponding to position 68 of the full length wild-type mouse EKLF polypeptide.

In particular embodiments of the fifth aspect where the first active agent is administered, the first active agent reduces or inhibits translocation of the endogenous EKLF polypeptide from the cytoplasm to the nucleus. In certain embodiments, the first active agent modifies a transactivator activity or modifies a repressor activity of the endogenous EKLF polypeptide. In some embodiments, the first active agent binds to the endogenous EKLF polypeptide. In various embodiments, the first active agent is a small organic molecule or a polypeptide, optionally an antibody or a functional fragment thereof. In certain embodiments, binding of the first active agent to the endogenous EKLF polypeptide inhibits its translocation from the cytoplasm to the nucleus.

In certain embodiments of the fifth aspect wherein the polypeptide or the nucleic acid is administered, or wherein the first active agent is administered, the method further comprises administering a second active agent that inhibits expression of the endogenous EKLF polypeptide. In particular embodiments, the second active agent is a nucleic acid molecule, optionally an antisense RNA, siRNA, shRNA or miRNA that binds an mRNA or complement thereof that encodes the endogenous EKLF polypeptide.

In particular embodiments of the fifth aspect of the present invention, the method results in reduced graying of the hair, increased motor coordination, increased muscle strength, reduced muscle weakness, increased motor coordination, reduced osteoporosis, greater bone volume, greater bone density, greater trabecular number, reduced trabecular spacing, or reduced loss of balance in the subject.

In certain embodiments of the fourth or fifth aspects, the subject is a mammal, optionally a human.

In a further related sixth aspect, the present invention includes a method of identifying an active agent capable of increasing longevity, enhancing life span or health span and/or inhibiting or reducing tumorigenesis or tumor occurrence or tumor metastasis of a subject, comprising: contacting an EKLF polypeptide or a cell expressing an EKLF polypeptide with a candidate agent; and measuring an amount of post-translational modification present on the EKLF polypeptide, or measuring an amount of an activity of the EKLF polypeptide, wherein if the amount of the post-translational modification or the amount of the activity is altered as compared to a control amount, the candidate agent is an active agent capable of increasing longevity or life span and/or inhibiting tumorigenesis or tumor metastasis of the subject. In particular embodiments, the EKLF polypeptide is a wild-type human EKLF polypeptide, or a variant or fragment thereof. In particular embodiments, the amount of post-translational modification is measured, and the candidate agent is the active agent if the measured amount is lower than the control amount. In some embodiments, the measured post-translational modification is sumoylation or phosphorylation. In particular embodiments, the sumoylation occurs at an amino acid corresponding to position 54 of the human EKLF polypeptide. In certain embodiments, the measured activity is translocation of the EKLF polypeptide from the cytoplasm to the nucleus, and the candidate agent is the active agent if the measured amount is lower than the control amount. In particular embodiments, the measured activity is transactivator activity, and the candidate agent is the active agent if the measured amount is modified, optionally less than, the control amount. In certain embodiments, the measured amount is repressor activity, and the candidate agent is the active agent if the measured amount is modified, optionally greater than, the control amount. In various embodiments, the control amount is a pre-determined value, or an amount associated with an EKLF polypeptide, e.g., a wild-type human EKLF polypeptide or fragment thereof, or cell not contacted with the candidate agent. In some embodiments, the EKLF polypeptide is an endogenous EKLF polypeptide or an exogenous EKLF polypeptide. In some embodiments, the exogenous EKLF polypeptide is a wild-type EKLF polypeptide. In certain embodiments, the cell comprises an exogenous nucleic acid capable of expressing the EKLF polypeptide.

In a related seventh aspect, the present invention includes a method of identifying an active agent capable of increasing longevity, extending the lifespan, enhancing the health span and/or inhibiting tumorigenesis or tumor occurrence or tumor metastasis of a subject, comprising: administering a candidate agent to a non-human transgenic animal described herein (e.g., a non-human animal of first aspect); and comparing the lifespan of the non-human transgenic animal after the administration of the candidate agent with that of a control animal, which was not administered the candidate agent, wherein if the lifespan of the non-human transgenic animal that was administered the candidate agent is longer than that of the control animal, then the candidate agent is the active agent capable of increasing longevity, extending the lifespan, enhancing the health span and/or inhibiting tumorigenesis of the subject.

In a further related eighth aspect, the present invention includes a method of identifying an active agent capable of increasing longevity and/or inhibiting tumorigenesis or tumor metastasis of a subject, comprising: contacting a cell capable of expressing a modified EKLF allele encoding a modified EKLF polypeptide comprising one or more amino acid modifications as compared to a wild-type EKLF polypeptide with a candidate agent; and measuring the expression level of the modified EKLF polypeptide, wherein if the expression level of the modified EKLF polypeptide is higher than the expression level in a control cell not contacted with the candidate agent, the candidate agent is an active agent capable of increase longevity and/or inhibiting tumorigenesis of the subject. In particular embodiments of the eighth aspect of the present invention, the one or more amino acid modifications comprises a modification at an amino acid position that is sumoylated or phosphorylated in the wild-type EKLF polypeptide, e.g., the wild-type human EKLF polypeptide. In certain embodiments, the one or more amino acid modifications comprises a modification of an amino acid corresponding to position 54 of the full length wild-type human EKLF polypeptide. In one embodiment, the modification of the amino acid at position 54 is a substitution of Lys, e.g., with Arg (K54R). In certain embodiments, the one or more amino acid modifications comprises a modification of an amino acid that is phosphorylated, e.g., in the human EKLF polypeptide, such as, but not limited to, a phosphorylated amino acid corresponding to position 68 of the full length wild-type mouse EKLF polypeptide.

BRIEF DESCRIPTION OF THE DRAWINGS

(FIG. 1A; top) Depicts the EKLF gene locus and the targeting locus. (FIG. 1A; bottom) Depicts the recombinant allele prior to (I) and after (II) Cre-mediated recombination. The protein-encoding portion of exon 2 of the EKLF gene was replaced by loxP-PGKgb2-neo-loxP EKLF K74R retroviral vector and a neomycin cassette (Neo, open box) flanked by lox P sites (black box). The hatched regions indicate the portion of the endogenous EKLF locus that was deleted, and the portion of the targeting vector that was inserted in to the EKLF locus, both before (I) and after (II) treatment with Cre recombinase to excise the neomycin cassette by Cre-mediated recombination. Nfix refers to the Nfix gene locus. Fbwx9 refers to the Fbwx9 gene locus. E1, E2, and E3 refers to exon 1, exon 2, and exon 3 of the EKLF gene, respectively; Intron 1 and Intron 2 refer to the first and second introns of the EKLF gene, respectively. Neo refers to neomycin cassette. PGK refers to the eukaryotic promoter PGK; gb2 refers to the gb2 prokaryotic promoter. Delete refers to the deletion of 50 nucleotides form intron 1 of EKLF; 5FA, 5RA, gt EKLF d 5', gt EKLF 3', gt EKLF PGK 5', Kin 5' and Kin 3' respectively refer to PCR primers for genotyping. Left and right arrows refer to location of genotyping primer, respectively. K74R indicates DNA modification resulting K74 substitution. PolyA refers to PolyA region. LoxP refers to LoxP site. (FIG. 1B) Genotyping of the wild-type (+/+) mice, heterozygous EKLF K74R mice (Kin/+) and homozygous EKLF K74R mice (Kin/Kin). (FIG. 1C) E13.5 embryos of wild-type (WT) and homozygous EKLF K74R mice (Kin). (FIG. 1D) Relative levels of the EKLF mRNA of the WT and EKLF K74R mouse.

FIGS. 2A and 2B show that the EKLF K74R substitution affects transcriptional activity of the EKLF polypeptide. (FIG. 2A) Relative levels of mRNA of Col1a1 of E14.5 fetal livers of wild-type (WT) and EKLF K74R (Kin) mice. (FIG. 2B) Relative levels of mRNA of Mpv171 of E14.5 fetal livers of wild-type (WT) and EKLF K74R (Kin) mice. Data were collected from 3 independent experiments. p<0.01, *p<0.001.

(FIG. 3A) Survival curves of the WT and Kin mice are shown. (FIG. 3B) Images demonstrating delayed de-pigmentation in the Kin mice are shown.

(FIG. 4A) Pictures of one each of wild-type (WT) and EKLF K74R (Kin) mice at 3 months of age. (FIG. 4B) Body weights of EKLF K74R (Kin) and WT mice at 3, 6, 12, 18 and 24 months of age. The canonical diurnal metabolic parameters, including food (FIG. 4C) and water (FIG. 4D) intake, were measured for WT and EKLF K74R (Kin) mice at 3 and 24 months of age, respectively. The data are means±SEM. Statistical significance was assessed by two-tailed Student's t-test.

FIGS. 6A-6C show measurements of the concentrations of fasting blood glucose (FIG. 6A) and insulin (FIG. 6B), and the glucose tolerance test (FIG. 6C) for wild-type (WT; circles) and EKLF K74R mice (Kin; squares). The data are presented as means±SEM, with n=3 to 9 in each group. Statistical significance was assessed by the two-tailed Student's t-test.

FIGS. 7A and 7B show comparisons of physical characteristics of wild-type (WT) and EKLF K74R (Kin) mice at 3-month and 24-month of age. (FIG. 7A) Results of the grip strength test are shown. (FIG. 7B) Results of the rotarod performance test are shown. Data are presented as mean±SEM (n=20 each). p-value(s) indicates the significance of the genotype effect in two-way repeated measures ANOVA. The data are presented as means±SEM. Statistical significance was assessed by two-tailed Student's t-test.

(FIG. 9A) MicroPET images are shown of mice administered with 100 Ci of 18F-FDG and scanned for 0.5 hr after injection. The white arrows indicate the tumors in liver, pancreas and spleen of wild-type mice but not EKLF K74R mice (Kin). (FIG. 9B) A table summarizing cancer occurrence in 2 out of 3 WT mice, but none in the 3 Kin mice, as examined after body dissection.

(FIG. 10A) Representative photos of lungs from wild-type (WT) and EKLF K74R (Kin) mice 14 days after injection of the B16F10 melanoma cells are shown. The lungs of all 3 injected WT mice developed tumors on the lungs (left panel), while none of the 3 Kin mice had tumors on their lungs (right panel). Scale bars are 5 mm. (FIG. 10B) Bar diagram of the comparison of tumor.

DETAILED DESCRIPTION OF THE INVENTION

Figure 1A:
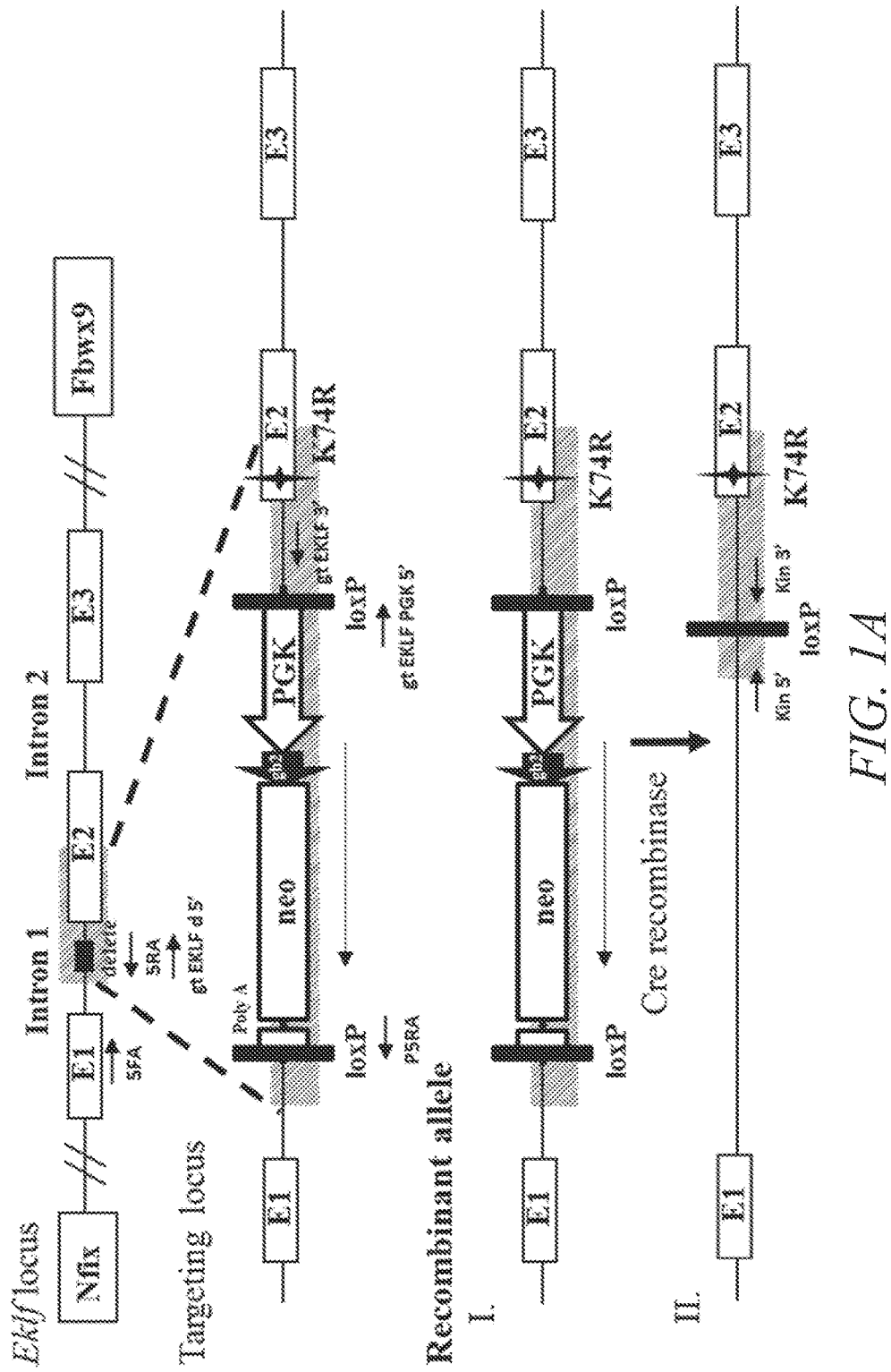
FIGS. 1A-1D show the generation of EKLF K74R mice by homologous recombination.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (3$^{rd}$ Edition, 2000); *DNA Cloning: A Practical Approach*, vol. I & II (D. Glover, ed.); *Oligonucleotide Synthesis* (N. Gait, ed., 1984); *Oligonucleotide Synthesis: Methods and Applications* (P. Herdewijn, ed., 2004); *Nucleic Acid Hybridization* (B. Hames & S. Higgins, eds., 1985); *Nucleic Acid Hybridization: Modern Applications* (Buzdin and Lukyanov, eds., 2009); *Transcription and Translation* (B. Hames & S. Higgins, eds., 1984); *Animal Cell Culture* (R. Freshney, ed., 1986); Freshney, R. I. (2005) *Culture of Animal Cells, a Manual of Basic Technique*, 5$^{th}$ Ed. Hoboken N.J., John Wiley & Sons; B. Perbal, *A Practical Guide to Molecular Cloning* (3$^{rd}$ Edition 2010); Farrell, R., *RNA Methodologies: A Laboratory Guide for Isolation and Characterization* (3$^{rd}$ Edition 2005). *Poly(ethylene glycol), Chemistry and Biological Applications*, ACS, Washington, 1997; Veronese, F., and J. M. Harris, Eds., *Peptide and protein PEGylation, Advanced Drug Delivery Reviews*, 54(4) 453-609 (2002); Zalipsky, S., et al., "*Use of functionalized Poly(Ethylene Glycols) for modification of polypeptides*" in Polyethylene Glycol Chemistry: Biotechnical and Biomedical Applications.

Definitions

For convenience, certain terms employed in the context of the present disclosure are collected here. Unless defined otherwise, all technical and scientific terms used herein have the same meaning as commonly understood by one of the ordinary skill in the art to which this invention belongs.

"Enhancing longevity" "increasing longevity" and "life-extension" are used interchangeably herein and refer to a delay of the normal aging process and/or prolonging the lifespan of an animal, e.g., an animal suffering from a life-threatening disorder (e.g., a cancer or tumor). Preferably, the longevity is due to an extension of the mature life phase, as opposed to an extension of the immature life phase, and is resulted from being treated by the present method.

"Enhancing health span" refers to a delay in the onset or severity of physical deterioration, diseases, or disorders associated with aging. Enhanced health span also refers to a reduction or reduced amount of physical deterioration, diseases, or disorders normally associated with aging, e.g., at a particular age.

As used herein, the term "allele" refers to one specific form of a gene within a cell or within a population, the specific form which may differ from other forms of the same gene in the sequence of at least one, and frequently more than one, variant sites within the sequence of the gene. The sequences at these variant sites that differ between different alleles are termed "variances", "polymorphisms", or "mutations". When a subject has two identical alleles of a gene, the subject is said to be homozygous for that gene or allele. When a subject has two different alleles of a gene, the subject is said to be heterozygous for that gene. Alleles of a specific gene can differ from each other in a single nucleotide or several nucleotides, and can include substitutions, deletions, and insertions of nucleotides. An allele of a gene can also be a form of a gene containing a mutation.

As used herein, the term "expression" is intended to refer to transcription of a gene when a condition is met, resulting in the generation of mRNA and usually encoded protein. Expression can be achieved or performed naturally by the cell (i.e., without artificially intervention) or may be achieved or performed artificially (i.e., with the involvement of artificially intervention, such as by the use of promoters regulated by the use of a chemical agent). The expression may also be initiated by a recombination event triggered by a site-specific recombinase, such as by Cre-mediated recombination. Expression may be measured by measuring mRNA transcribed from the gene or by measuring protein encoded by the gene.

The term "nucleic acid" refers to polynucleotides such as deoxyribonucleic acid (DNA) and where appropriate, ribonucleic acid (RNA). Nucleic acids include but are not limited to single-stranded and double-stranded polynucleotides. Illustrative polynucleotides include DNA, single-stranded DNA, cDNA, and mRNA. The term also includes, analogs of either DNA or RNA made from nucleotide analogs, and as applicable, single (sense or antisense) and double-stranded polynucleotides. The term further includes modified polynucleotides, including modified DNA and modified RNA, e.g., DNA and RNA comprising one or more unnatural nucleotide or nucleoside. The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, and/or which have similar binding properties as the reference nucleic acid, and/or which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

An "isolated" nucleic acid molecule is a nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in nature cells.

The term "vector" refers to a nucleic acid molecule capable of transporting another nucleic acid to which it has been linked. The term "expression vector" refers to a vector comprising a promoter operably linker to a nucleic acid in a manner allowing expression of the operably linked nucleic acid. Vectors or expression vectors as used herein thus include plasmids or phages capable of synthesizing the subject protein encoded by the respective recombinant gene carried by the vector. Vectors or expression vectors also include viral-based vectors capable of introducing a nucleic acid into a cell, e.g., a mammalian cell. Certain vectors are capable of autonomous replication and/or expression of nucleic acids to which they are linked.

In the present disclosure, nucleic acid is "operably linked" when it is placed into a functional relationship with another nucleic acid sequence. For example, a promoter is operably linked to a coding sequence if it affects the transcription of the sequence; or a ribosome binding site is operably linked to a coding sequence if it is positioned so as to facilitate translation. In general, "operably linked" means that the DNA sequences being linked are contiguous, and in reading phase. However, enhancers do not have to be contiguous. Linking is accomplished by ligation at convenient restriction sites, if such sites do not exist, the synthetic oligonucleotide adaptors or linkers are used in accordance with conventional practice.

The term "transfection" refers to the introduction of nucleic acid, e.g., an expression vector, into a recipient cell by nucleic acid mediated gene transfer. "Transformation" refers to a process in which a cell's genotype is changed as the result of the cellular uptake of exogenous DNA or RNA, and the transformed cell expresses a desired heterologous protein.

As used herein the term "transgene" refers to a nucleic acid sequence which is partly or entirely heterologous, i.e., foreign, to the transgenic animal or cell into which it is introduced, or is homologous to an endogenous gene of the transgenic animal or cell into which it is introduced, but which is designed to be inserted, or is inserted, into the animal's genome in such a way that the genome of the cell to which it is inserted is altered. A transgene can be operably linked to one or more transcriptional regulatory sequences and any other nucleic acid, such as introns, that may be necessary for optimal expression of a selected nucleic acid. Therefore, the term "transgenic" is used herein as an adjective to describe the property of an animal or a construct, of harboring a transgene. For example, "a transgenic animal" is a non-human animal, preferably a non-human mammal, more preferably, a rodent, in which one or more of the cells of the animal contain heterologous nucleic acid introduced by way of human intervention, such as by transgenic techniques well known in the art, including gene knock-in techniques. The nucleic acid is introduced into the cell, directly or indirectly by introduction into a precursor of the cell, via deliberate genetic manipulation, such as by microinjection or by infection with a recombinant virus. Transgenic animals include, but are not limited to, knock-in animals.

A "knock-in (Kin)" refers to the targeted insertion of a transgene in a host cell genome that results in expression of the transgene. "Knock-in" transgenics can comprise a heterozygous knock-in of a transgene. In certain embodiments, a "knock-in" results in the replacement of an endogenous gene (or portion thereof) with an exogenous gene (or portion thereof), e.g., resulting in the targeted mutation of one or both alleles. "Knock-in" also encompasses expression of a transgene by exposing the animal to a substance that promotes such expression, by introducing an enzyme that promotes recombination at the site of targeted insertion (e.g., Cre in Cre-lox system), or by some other method.

"Homozygous" state means a genetic condition existing when the same alleles reside at corresponding loci on homologous chromosomes. In contrast, "heterozygous" state means a genetic condition existing when different alleles reside at corresponding loci on homologous chromosomes.

The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammalis except human.

The term "treatment" as used herein is intended to mean obtaining a desired pharmacological and/or physiologic effect, e.g., delaying or inhibiting cancer occurrence, growth, or metastasis, or ameliorating ischemic injury to an organ (e.g., brain). The effect may be prophylactic in terms of completely or partially preventing or inhibiting occurrence of a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition (e.g., a cancer or heart failure) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The term "administered", "administering" or "administration" are used interchangeably herein to refer a mode of delivery, including, without limitation, intraveneously, intramuscularly, intraperitoneally, intraarterially, intracranially, or subcutaneously administering an agent (e.g., a compound or a composition) of the present invention.

The term "an effective amount" as used herein refers to an amount effective, at dosages, and for periods of time necessary, to achieve the desired result with respect to the treatment of a disease or condition, such as aging. For example, in the treatment of a cancer, an agent (i.e., a compound, a polypeptide, or a polynucleic acid encoding a therapeutic polypeptide) which decreases, inhibits, prevents, delays or suppresses or arrests any symptoms of the cancer would be effective. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two or more doses in a suitable form to be administered at one, two or more times throughout a designated time period.

The term "subject" refers to an animal including the human species that is treatable with the method of the present invention. The term "subject" intended to refer to both the male and female gender unless one gender is specifically indicated. Accordingly, the term "subject" comprises any mammal which may benefit from the treatment method of the present disclosure.

The term "cellular proliferative disorder," "tumor," and "cancer" are used interchangeably herein, and is intended to mean any disorder characterized by deregulated or uncontrolled, autonomous cell growth, including malignant and non-malignant growth, lack of differentiation and ability to invade local tissues and metastasize. Examples of this disorder include, but are not limited to, carcinoma, lymphoma, blastoma, sarcoma, and leukemia or lymphoid malignancies. More particular examples of such disorders include, but are not limited to, liver cancer, colon cancer, breast cancer, prostate cancer, hepatocellular carcinoma, melanoma, lung cancer, glioblastoma, brain tumor, hematopoeitic malignancies, retinoblastoma, renal cell carcinoma, head and neck cancer, cervical cancer, pancreatic cancer, esophageal cancer, and squama cell carcinoma.

The singular forms "a", "and", and "the" are used herein to include plural referents unless the context clearly dictates otherwise.

A "decreased" or "reduced" amount is typically a "statistically significant" amount, and may include, for example, a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) relative to a control. Other examples of comparisons and "statistically significant" amounts are described herein. "Decrease," as used herein, can refer to "inhibit," "reduce," "curb," "abate," "diminish," "lessen," or "lower."

A "increased" or "enhanced" amount is typically a "statistically significant" amount, and may include, for example, a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% increase. An increased or enhanced amount may also include a 2-fold, 3, fold, 4 fold, 5 fold, 6 fold, 7 fold, 8-fold, 9-fold, 10 fold, 20-fold, 30 fold, 40 fold, 50 fold, 60 fold 70 fold, 80-fold, 90-fold, 100-fold, 200-fold, 300-fold, 400-fold, 500-fold, 1,000-fold, 10,000-fold, or greater than 10,000-fold increase (including all integers and ranges in between) relative to a control. Other examples of comparisons and "statistically significant" amounts are described herein. "Increase," as used herein, can refer to "agonize," "enhance," "inflate," "escalate," expand," "augment," "enlarge," or "raise."

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. The polypeptides described herein are not limited to a specific length of the product; thus, peptides, oligopeptides, and proteins are included within the definition of polypeptide, and such terms may be used interchangeably herein unless specifically indicated otherwise. The polypeptides described herein may also comprise post-expression modifications, such as glycosylations, acetylations, phosphorylations and the like, as well as other modifications known in the art, both naturally occurring and non-naturally occurring. A polypeptide may be an entire protein, or a subsequence, fragment, variant, or derivative thereof.

The term "similar" as used herein, when referring to properties, characteristics, actions, or activities that can be measured and/or quantified, refers to the absence of a detectable and/or a statistically significant difference.

The term "wild-type" refers to a gene or gene product that has the characteristics of that gene or gene product when isolated from a naturally-occurring source. A wild-type gene or gene product (e.g., a polypeptide) is that which is most frequently observed in a population and is thus arbitrarily designed the "normal" or "wild-type" form of the gene.

A "control animal," as used herein, refers to an animal that closely resembles the experimental animal, e.g. a genetically modified animal that expresses modified EKLF polypeptide, without possessing the experimental feature, e.g. expression of a modified EKLF polypeptide. For a given experiment or experimental comparison, one of ordinary skill in the art will be able to select an appropriate control animal depending on considerations that can include, but are not limited to, the nature of the experiment or comparison, the species and age of the genetically modified animal, and experimental feasibility Unless otherwise stated, the control animal does not comprise a modification at the EKLF locus and does not express modified EKLF polypeptide. In some cases, the control animal may be a littermate of the same gender as the genetically modified animal.

An "aged" animal, as used herein, refers to an adult animal that displays at least one phenotype associated with normal ageing. The exact age that an animal will be considered "aged" depends on the species and/or the strain of the animal, as well as the phenotype in question, and can readily be determined by those of skill in the art.

"Homology" refers to the percentage number of amino acids that are identical or constitute conservative substitutions. Homology may be determined using sequence comparison programs such as GAP (Deveraux et al., 1984, *Nucleic Acids Research* 12, 387-395), which is incorporated herein by reference. In this way sequences of a similar or substantially different length to those cited herein could be compared by insertion of gaps into the alignment, such gaps being determined, for example, by the comparison algorithm used by GAP.

By "statistically significant", it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less. The term "significant" encompasses and includes the term "statistically significant."

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polypeptides include "reference sequence," "comparison window," "sequence identity," "percentage of sequence identity" and "substantial identity." A "reference sequence" is at least 12 but frequently 15 to 18 and often at least 25 monomer units, inclusive of nucleotides and amino acid residues, in length. Because two polypeptides may each comprise (1) a sequence (i.e., only a portion of the complete polypeptides sequence) that is similar between the two polypeptides, and (2) a sequence that is divergent between the two polypeptides, sequence comparisons between two (or more) polypeptides are typically performed by comparing sequences of the two polypeptides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and) XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, Nucleic Acids Res, 25: 3389-3402). When utilizing BLAST and Gapped BLAST programs, the default parameters of the respective programs (e.g., XBLAST and NBLAST) can be used.

The term "antibody" herein is used in the broadest sense and specifically covers intact monoclonal antibodies, polyclonal antibodies, multispecific antibodies (e.g. bispecific antibodies) formed from at least two intact antibodies, and antibody fragments, so long as they exhibit the desired antigen-binding activity. "Antibody fragments" comprise a portion of an intact antibody, preferably comprising the antigen-binding or variable region thereof. Examples of antibody fragments include Fab, Fab', $F(ab')_2$, scFv and Fv fragments; diabodies; nanobodies; linear antibodies; single-chain antibody molecules; and multispecific antibodies formed from antibody fragment(s).

Genetically Modified Animals

The present disclosure is based, in part, on the development of a knock-in animal, e.g. a knock-in mouse, that serves as an animal model for longevity, anti-aging, anti-carcinogenesis, and/or anti-metastasis, wherein one or both of the endogenous Erythroid Kruppel-like factor (EKLF) gene alleles are modified to encode a modified EKLF polypeptide, including any of those specifically described herein. The expression of the modified EKLF polypeptide in the genetically modified animal leads to an enhanced lifespan and/or health span of the animal, and/or the suppression or inhibition of tumor formation and/or the metastasis of cancerous cells. Therefore, the introduction of the modified EKLF allele provides a means for increasing the lifespan or health span of a subject, a means for treating a cellular proliferative disorder, e.g., inhibiting tumor formation or tumor metastasis, as well as a means for screening candidate agents suitable as anti-aging and/or anti-tumor agents.

Particular embodiments contemplate that the genetically modified non-human animal model developed herein is a valuable tool to study aging, longevity, and progression and treatment of a cellular proliferative disorder (e.g., cancer). This animal model is particularly advantageous in that it does not exhibit impaired or modified metabolism as compared to normal animals. In particular, the non-human genetically modified animal model of the present disclosure finds utilities in studying aging, longevity, and screening candidates as anti-aging agents as well as agents for the treatment or prevention of cancer, including metastatic cancer.

Particular embodiments are directed to a genetically modified animal that comprises a nucleic acid (e.g., DNA) sequence that encodes a modified EKLF polypeptide. A "modified EKLF polypeptide" includes EKLF variants having at least one amino acid modification as compared to a wild-type EKLF protein, and fragments thereof having at least 100, 200, 300, or 350 amino acids, that have at least 80%, 85%, 90%, 95%, 96%, 97%, 98%, or 99% sequence identity to a wild-type EKLF protein.

Certain embodiments are directed to a genetically modified animal that comprises a nucleic acid sequence that encodes a modified EKLF polypeptide, wherein the animal also comprises a nucleic acid sequence that encodes a wild-type EKLF. Particular embodiments are directed to a genetically modified animal that comprises a nucleic acid (e.g., DNA) sequence that encodes a modified EKLF polypeptide, wherein the animal does not also comprises a nucleic acid sequence that encodes a wild-type EKLF. In various embodiments, the animal expresses the modified EKLF polypeptide and the endogenous EKLF polypeptide, while in some embodiments, the animal expresses only the modified EKLF polypeptide.

In some embodiments, the nucleic acid sequence encoding the modified EKLF is regulated by an endogenous EKLF gene promoter. Certain embodiments are directed to a genetically modified non-human animal that expresses a modified EKLF protein, wherein the genetically modified animal comprises a nucleic acid sequence that encodes a modified EKLF protein, wherein the EKLF protein is under the control of the endogenous EKLF promoter. Some embodiments are directed to a genetically modified non-human animal that expresses a modified EKLF protein, wherein the genetically modified animal comprises a nucleic acid sequence (e.g., DNA) that encodes a modified EKLF protein and an exogenous promoter, wherein the nucleic acid sequence that encodes the modified EKLF is operably linked to or under control of the exogenous promoter. In some embodiments, the exogenous promoter is selected from promoters that that direct expression of the transgene in a constitutive manner, promoters that direct the expression in a tissue specific manner, inducible promoters e.g. Tet-On inducible promoters, and promoters that direct expression in a developmental or timing dependent manner. Certain embodiments are directed to a genetically modified non-human animal that expresses a modified EKLF protein, wherein the genetically modified animal comprises a nucleic acid sequence that encodes a modified EKLF protein, wherein the EKLF protein is under the control of the endogenous EKLF promoter. By "promoter" is meant a region of DNA that initiates transcription of a particular gene. By "endogenous promoter" is meant a promoter that naturally directs expression of the gene of interest in a cell or subject, i.e., a native promoter. In the case of knock-in mice, the expression of the modified gene may be directed by the endogenous mouse promoter for that gene.

Particular embodiments are directed to a non-human EKLF knock-in animal. As used herein, "knock-in animal" refers to a transgenic animal generated by a genetic engineering method that involves the insertion of a DNA sequence, e.g., a cDNA sequence, at a particular locus in an organism's chromosome. The insert is flanked by DNA from a non-critical locus, and homologous recombination allows the transgene to be targeted to that specific, non-critical integration site. The term "knock-in" is intended to include first generation animals as well as progeny thereof that have the transgene in at least one allele thereof. In some embodiments, the insert comprises DNA that is targeted to the EKLF gene locus, or a fragment thereof, wherein the insert encodes a modified EKLF polypeptide or a region or portion thereof. In some embodiments, the insert is targeted to a protein encoding region of the EKLF gene locus. In certain embodiments, the insert encodes a modified EKLF polypeptide and a modified EKLF promoter.

"EKLF knock-in" as used herein, refers to a transgenic non-human animal whereby nucleic acid that encodes a modified EKLF polypeptide, or portion or region thereof, has been inserted into the EKLF locus, e.g., to replace the nucleic acid of the animal that encodes the corresponding wild-type EKLF polypeptide, or portion or region thereof. In some embodiments, the knock-in animal is heterozygous, comprising one copy of the endogenous EKLF gene and one copy of the modified knock-in EKLF gene. In particular embodiments, the genetically modified animal is an EKLF knock-in mouse. In certain embodiments, the knock-in animal is homozygous, comprising two copies of the modified knock-in EKLF gene.

In certain embodiments, the non-human animal is genetically modified by the replacement of an endogenous EKLF genomic sequence (or a portion thereof), at an endogenous EKLF locus, with a modified EKLF genomic sequence (or a portion thereof) to form a modified locus, wherein the modified EKLF genomic sequence comprises at least one modified protein-coding exon. In some embodiments, the replacement comprises a modified genomic fragment comprising at least two protein-coding exons of EKLF. In some embodiments, the replacement comprises a modified genomic fragment that comprises at least three protein-coding exons of modified EKLF. In particular embodiments, the non-human animal is genetically modified by the replacement of the endogenous exon 2 of the EKLF gene with a modified exon 2 of the EKLF gene (or portion thereof). In particular embodiments, a region of the endogenous EKLF genomic sequence that encodes a sumoylation site or a phosphorylation site of the EKLF protein is replaced by a modified EKLF genomic sequence.

Particular embodiments are directed to genetically modified non-human animals that comprise a modified EKLF locus that encodes an EKLF polypeptide comprising a modification of one or more amino acids compared to the endogenous, wild-type EKLF, including any of those described herein. In particular embodiments, the modified EKLF polypeptide comprises a modification that inhibits its sumoylation. The organisms are generally able to pass the modification to progeny, i.e., through germline transmission. In some embodiments, the genetically modified non-human animals are offspring of a parent comprising a modified EKLF locus that encodes a modified EKLF polypeptide. In some embodiments, the offspring are homozygous for the modified EKLF locus. In certain embodiments, the offspring are heterozygous for the modified EKLF locus.

Certain embodiments are directed to genetically modified non-human animals that comprise a modified EKLF locus that encodes an EKLF polypeptide comprising a modification of one or more amino acids compared to the endogenous, wild-type EKLF, and further comprise a modification at one or more additional loci. In some embodiments, the genetically modified animal comprises modifications at one additional locus, two additional loci, three additional loci, four additional loci, five additional loci, six additional loci, seven additional loci, eight additional loci, nine additional loci, ten additional loci, or more than ten additional loci. In some embodiments, the modification of the additional locus is a gene knockout, gene knock-in, or the insertion of an exogenous gene.

Particular embodiments are directed to a non-human EKLF knock-in animal that is crossed with a genetically modified animal comprising a modification of at least one additional locus. Certain embodiments are directed to offspring that express a modified EKLF polypeptide that are the product of a cross between an EKLF knock-in animal and genetically modified animal comprising a modification of at least one additional, non-EKLF locus. Genetically modified animals are known in the art, and may include transgenic animals with inducible expression of exogenous peptides, inducible knockout animal models, e.g. CRE-loxP, inducible knock-in animals, e.g. crisper/Cas. In certain embodiments, the EKLF knock-in is crossed with a transgenic animal, e.g., a knock-in animal, and/or a knockout animal. In some embodiments, the EKLF knock-in animal is crossed with a genetically modified animal that models a disease, e.g. cancer, or aspects of longevity, e.g. S6K1 knockout.

In some embodiments, the genetically modified non-human animal may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). In certain embodiments, the non-human animal is a mammal, e.g., a non-human mammal. In certain embodiments, the non-human animal is a small mammal, e.g., of the superfamily Muroidea. In some embodiments, the genetically modified animal is a rodent. In some embodiments, the rodent is selected from a mouse, a rat, and a hamster. In some embodiments, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, *Malagasy* rats and mice), Platacanthomyidae (e.g., spiny dormice), and Spalacidae (e.g., mole rats, bamboo rats, and zokors). In some embodiments, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse. In particular embodiments, the genetically modified non-human animal is an EKLF knock-in mouse.

In certain embodiments, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al. (2000) Establishment and Chimera Analysis of 129/SvEv- and C57BL/6-Derived Mouse Embryonic Stem Cell Lines). In some embodiments, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In some embodiments, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain. In yet another embodiment, the mouse is of a hybrid line (e.g., 50% BALB/c-50% 12954/Sv; or 50% C57BL/6-50% 129; e.g., F1H4 cells, see, e.g., Auerbach et al. (2000)).

In certain embodiments, the non-human animal is a rat. In some embodiments, the rat is selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

Although genetically modified cells are also provided that comprise the modifications described herein, in many aspects and embodiments, the genetically modified non-human animals comprise the modification of the endogenous EKLF locus in the germline of the animal.

In various embodiments, the non-human animals are mammals. In certain embodiments, the mammals are rodents. Particular embodiments are directed to rodents that comprise a modification of the EKLF gene at one or both endogenous rodent EKLF loci. Methods are provided for making rodents, e.g., mice, that comprise a replacement of an endogenous EKLF gene or fragment thereof (e.g., a fragment comprising one or more exons) with a modified EKLF gene, or fragment thereof, at one or both of the endogenous EKLF loci. Particular embodiments are directed to cells, tissues, and mice that comprise the modified EKLF gene, as well as cells, tissues, and mice that express human EKLF from an endogenous non-human EKLF locus. Rodents that express a modified EKLF protein under control of an endogenous rodent promoter are also provided.

Certain embodiments are directed to methods of generating a genetically modified knock-in animal that expresses a modified EKLF polypeptide, including but not limited to homozygotes that express the modified EKLF polypeptide but not a wild-type EKLF polypeptide. Techniques and strategies for generating knock-in animals, e.g. mice, are well known in the art and are reviewed in (Doyle et al. 2012 Transgenic Res. 21(2): 327-349; and Roebroek et al. Chapter 10 In: Hofker M H, Deursen Jv, editors. Transgenic mouse: Methods and protocols. Humana Press; Totowa, N.J.: 2003. pp. xiiipp. 3741 pp. 3187-3200).

In one such strategy, knock-in mice are generated in a two-staged process that utilizes pluripotent embryonic stem (ES) cells as a vehicle with which to translate experimental genetic manipulations into Mendelian inheritable traits in mice. In certain strategies, an embryonic stem cell isolated from a mouse is transfected with a DNA targeting construct comprising regions of homology to an endogenous gene or chromosomal sequence, to facilitate homologous recombination. The DNA targeting construct not only contains specific regions of gene homology but also has a uniquely engineered mutation or sequence change such that the 1-to-1 replacement of the endogenous gene (or portion thereof) with sequence derived from the targeting construct following transfection into ES cells yields an allele in the genome of these cells containing this new sequence variant. Targeted ES cell clones containing the appropriate genetic changes are transferred to the blastocoel cavities of 3.5 day blastocyst embryos. In turn, the embryos are transferred to surrogate mothers where gestation is completed generating ES cell-derived founder mice which have inherited the new sequence variant (i.e., the knock-in mutation), generating a gain-of-function allele at this chosen genetic locus. One of skill in the art will recognize other suitable strategies for generating knock-in animals, e.g. strategies utilizing Cre-loxP system, and CRISPER/Cas9 technologies.

For the non-human animals where suitable genetically modifiable ES cells are not readily available, other methods are employed to make a non-human animal comprising the genetic modification. Such methods include, for example but not limited to, modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

Some embodiments are directed to methods of generating a genetically modified animal that expresses a modified EKLF polypeptide utilizing the Cre-loxP system. The Cre-loxP system has been used to modify the expression of a selected gene or induce chromosomal rearrangements in a controlled fashion, through the induction of a recombination in the genome of isolated cells or transgenic animals. The system relies on an enzyme of the PI bacteriophage, Cre recombinase, that recognizes a short (34 bp) asymmetric consensus sequence called loxP. When two such sequences of the same orientation are located on a DNA molecule, the enzyme will catalyze the recombination between these two sites and excise the intervening DNA segment. If the two loxP sequences are located on two different DNA molecules, such as on two chromosomes, then Cre will mediate an intermolecular recombination. The results of the recombination depends on the orientation of the loxP sites, for two lox sites on the same chromosome arm, inverted loxP sites will cause an insertion, while a direct repeat of loxP sites will cause a deletion event. Besides the Cre-loxP recombination system described herein, other site-directed recombination systems can also be used to generate non-human transgenic animal model as exemplified in the Examples of the present disclosure.

The genetically modified animals are screened and evaluated to select those animals having the phenotype of interest. Initial screening can be performed using, for example, Southern blot analysis or PCR techniques to analyze animal tissues to verify that integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and reverse transcriptase-PCR (RT-PCR). Samples of the suitable tissues can be evaluated immunocytochemically using antibodies specific for the transgene. Alternative or additional methods for evaluating the presence of the transgene include, but are not limited to, suitable biochemical assays such as enzyme and/or immunological assays, histological stains for particular marker or enzyme activities, flow cytometric analysis, and the like. Analysis of the blood may also be useful to detect the presence of the transgene product in the blood.

Particular embodiments are directed to methods of producing a genetically modified animal whereby the genetically modified animal is produced from a pluripotent or totipotent cell (e.g., an ES cell). In certain embodiments, the non-human animal is produced by employing a nuclear injection step wherein a nucleic acid construct comprising the modified EKLF gene or a portion thereof (optionally with upstream and/or downstream endogenous non-human regulatory sequences) is introduced by pronuclear injection. In some embodiments, the nucleic acid construct comprises a genomic fragment that comprises at least one modified protein-coding exons EKLF. In certain embodiments, the fragment contains portions of modified EKLF exon 2.

Some embodiments are directed to methods of generating a genetically modified animal that expresses a modified EKLF polypeptide comprising the steps of a) obtaining a vector comprising a polynucleotide encoding a modified EKLF polypeptide or a portion thereof; b) injecting the vector into an embryonic stem (ES) cell of a non-human animal; c) transferring an ES cell comprising the vector into a blastocyst embryo; d) transferring the blastocyst embryo into a surrogate mother where gestation of the embryo is completed, thereby generating a founder animal that comprises the polynucleotide encoding the modified EKLF polypeptide, thereby generating the genetically modified animal. In some embodiments, the genetically modified animal is a knock-in animal, wherein the vector is a targeting vector comprising polynucleotides homologous to endogenous DNA of the animal which flank the polynucleotide that encodes the modified EKLF at the 3' and 5' ends. In particular embodiments, injecting the vector comprising polynucleotides homologous to endogenous DNA of the animal into the ES cell results in insertion of the polynucleotide into the genome of the ES cell through homologous recombination. In certain embodiments, the homologous DNA is homologous to EKLF gene loci. In particular embodiments, the targeting vector further comprises selection cassette for use in identifying an ES cell comprising the vector following injection of the vector into the ES cell. In particular embodiments, the selection cassette is a PGK-gb2-neo cassette. In certain embodiments, the selection cassette is flanked with loxP sites, and the method of generating a genetically modified animal further comprises the step of e) crossing an adult founder animal with a transgenic animal that expresses Cre in germline cells, and obtaining the resulting progeny of the cross, thereby obtaining an animal expressing a modified EKLF polypeptide that does not comprise a selection cassette in its genome.

Particular embodiments are directed to methods of generating a knock-in mouse expressing modified EKLF polypeptide, comprising the steps of a) obtaining a vector comprising a polynucleotide encoding a modified EKLF polypeptide (or portion thereof) flanked on the 5' and 3' ends with polynucleotides homologous to endogenous mouse EKLF gene; b) injecting the vector into an mouse ES cell of a non-human animal, wherein the polynucleotide encoding modified EKLF is inserted into the genome of the ES cell at the EKLF gene loci through homologous recombination; c) transferring an ES cell comprising the vector into a 3.5 day old mouse blastocyst embryo; and d) transferring the blastocyst embryo into a surrogate mouse dam for the remainder of gestation, thereby generating a founder animal that comprises the polynucleotide encoding the modified EKLF polypeptide or portion thereof, thereby generating the genetically knock-in mouse. In certain embodiments, the vector further comprises a selection cassette. In some embodiments, the selection cassette is a PGK-gb2-neo cassette. In some embodiments, the vector comprises a selection cassette flanked by loxP sites, and the method further comprises the step of e) crossing an adult founder animal with a transgenic mouse that expresses Cre in germline cells, and obtaining the resulting progeny of the cross, thereby obtaining an EKLF knock-in mouse that does not comprise a selection cassette in its genome. In some embodiments, the vector comprises a polynucleotide encoding a EKLF with a lysine to arginine substitution at position 74 (K74R).

Once founder animals are produced, they can be bred, inbred, outbred, or crossbred to produce colonies of the particular animal, including homozygous animals. Examples of such breeding strategies include, but are not limited to, outbreeding of founder animals with more than one integration site in order to establish separate lines; inbreeding of separate lines in order to produce transgenics, e.g. knock-in animals, that express the transgene at higher levels because of the effects of additive expression of each transgene; crossing of heterozygous transgenic mice to produce mice homozygous for a given integration site in order to both augment expression and eliminate the need for screening of animals by DNA analysis; crossing of separate homozygous lines to produce compound heterozygous or homozygous lines; breeding animals to different inbred genetic backgrounds so as to examine effects of modifying alleles on expression of the transgene and the effects of expression.

Particular embodiments are directed to a cell of (e.g., derived from or obtained from) a genetically modified animal that comprises DNA encoding modified EKLF polypeptide at one or both EKLF loci. In some embodiments, the cell comprises DNA encoding modified EKLF polypeptide at one EKLF locus. In certain embodiments, the cell comprises DNA encoding modified EKLF polypeptide at both EKLF loci. In some embodiments, the cell is isolated from the genetically modified animal. In particular embodiments, the cell expresses the modified EKLF polypeptide. In certain embodiments, the cell does not express the modified EKLF polypeptide. In certain embodiments, the cell has an ectodermal lineage. In some embodiments, the cell is selected from a Trichocyte, Keratinocyte, Gonadotrope, Corticotrope, Thyrotrope, Somatotrope, Lactotroph, Neuron, Glia, Schwann cell, Satellite glial cell, Chromaffin cell, Parafollicular cell, *Glomus* cell, Melanocyte, Nevus cell, Merkel cell, Odontoblast, Cementoblast, Corneal keratocyte, Oligodendrocyte, Astrocyte, Ependymocytes, and Pinealocyte. In certain embodiments, the cell has an endodermal lineage. In some embodiments, the cell is a selected from a Type 1 Pneumocyte, Type 2 Pneumocyte, Club cell, Goblet cell, Gastric chief cell, Parietal cell, Foveolar cell, Enteroendocrine cell, G cell, Delta cell, Enterochromaffin-like cell, Enteroendocrine cell, Gastric inhibitory polypeptide S cell, Delta cell, Cholecystokinin, Goblet cell, Paneth cell, Enterocyte, Microfold cell, Hepatocyte, Hepatic stellate cell, Kupffer cell, Cholecystocyte, Centroacinar cell, Pancreatic stellate cell, Alpha cell, Beta cell, Delta cell, F cell, PP cell, Epsilon cell, Follicular cell, Parathyroid chief cell, Oxyphil cell, and Urothelial cell. In some embodiments, the cell has a mesodermal lineage. In some embodiments, the cell is selected from an Osteoblast, Osteocyte, Chondroblast, Chondrocyte, Lipoblast, Adipocyte. Myoblast, Myocyte, Myosatellite cell, Tendon cell, Cardiac muscle cell, Fibroblast, Fibrocyte, Interstitial cell of Cajal, Angioblast, Endothelial cell, Mesangial cell, Intraglomerular mesangial cell, Extraglomerular mesangial cell, Juxtaglomerular cell, Macula densa cell, Stromal cell, Interstitial cell, Telocytes, Simple epithelial cell, Podocyte, Kidney proximal tubule brush border cell, Sertoli cell, Leydig cell, Granulosa cell, Peg cell, Germ cell, spermatozoon, ovum, Lymphoid, Lymphoblast, lymphocyte, Myeloid, Endothelial progenitor cell, Endothelial colony forming cell, Endothelial stem cell, Angioblast, Mesoangioblast, Pericyte, and Mural cell. In some embodiments, the cell is a stem cell. In certain embodiments, the cell is a totipotent stem cell, pluripotent stem cell, multipotent stem cell, oliopotent stem cell, or unipotent stem cell.

Particular embodiments are directed to a tissue of (e.g., derived from or obtained from) a genetically modified animal that comprises a modified EKLF locus that encodes a modified EKLF polypeptide. In some embodiments, the tissue is isolated from the genetically modified animal. In particular embodiments, the tissue comprises a modified EKLF locus that encodes a modified EKLF polypeptide, wherein the tissue expresses the modified EKLF polypeptide. In certain embodiments, the tissue comprises a modified EKLF locus that encodes a modified EKLF polypeptide, wherein the tissue does not express the modified EKLF polypeptide. In some embodiments, the tissue is a connective tissue, a nervous tissue, an epithelial tissue, or a muscle tissue.

Certain embodiments are directed to an organ of (e.g., derived from or obtained from) a genetically modified animal that comprises a modified EKLF locus that encodes a modified EKLF polypeptide. In some embodiments, the organ is isolated from the genetically modified animal. In particular embodiments, the organ comprises a modified EKLF locus that encodes a modified EKLF polypeptide, wherein the organ expresses the modified EKLF polypeptide. In certain embodiments, the organ comprises a modified EKLF locus that encodes a modified EKLF polypeptide, wherein the organ does not express the modified EKLF polypeptide. In some embodiments, the organ is an organ of the Integumentary system, Skeletal system, Muscular system, Lymphatic system, Respiratory system, Digestive system, Nervous system, Endocrine system, Cardiovascular system, Urinary system, or reproductive system. In some embodiments, the organ is skin, hair, nail, bone, joint, skeletal muscle, red bone marrow, thymus, lymphatic vessel, thoracic duct, spleen, lymph node, nasal cavity, pharynx, larynx, trachea, bronchus, lung, oral cavity, esophagus, liver, stomach, small intestine, large intestine, rectum, anus, brain, spinal cord, nerve, pineal gland, pituitary gland, thyroid gland, thymus, adrenal gland, pancreas, ovary, testis, heart, blood vessel, kidney, ureter, urinary bladder, urethra, prostate gland, penis, testis, scrotum, ductus deferens, Mammary glands, ovary, uterus, vagina, or uterine tube.

By "isolated" it is meant that the cell, tissue, or organ is removed from the animal. In some embodiments, the cell, tissue, or organ is living, e.g. suitable for culture. In some embodiments, the cell, tissue, or organ is not considered live, e.g. fixed, and is suitable for analysis.

Certain embodiments are directed to a construct for use in generating a genetically modified animal that expresses a modified EKLF polypeptide, e.g., a knock-in targeting vector. In particular embodiments, the construct comprises nucleic acid, e.g. DNA or cDNA, that comprises a modified sequence encoding at least a portion of a transcribed region of the modified EKLF gene. In some embodiments, the construct contains a nucleic acid sequence comprising one or more modified EKLF exons. In particular embodiments, the construct comprises a selection marker, e.g. a PGK-gb2-neo template that encodes the neomycin/kanamycin resistance gene. In some embodiments, the construct comprises a selection marker that is flanked by loxP. Particular embodiments are directed to a construct for use in generating knock-in mouse that comprises a targeting vector comprising a modified mouse EKLF exon 2 (or portion thereof) and a selectable marker, e.g., aPGK-gb2-neo selection cassette, flanked by two LoxP sites. In one embodiment, a knock-in targeting construct comprises: (i) at least a portion of a first EKLF gene sequence; and (ii) at least a portion of a second EKLF gene sequence comprising a modification. In one embodiment, a knock-in targeting construct comprises: (i) at least a portion of a first EKLF gene sequence; (ii) a polyA sequence; (iii) a selectable marker (e.g. neomycin resistance) gene sequence; (iv) a promoter (e.g., PGK (phosphoglycerate kinase 1)) sequence; and (v) at least a portion of a second EKLF gene sequence comprising a modification. In one embodiment, a knock-in targeting construct comprises: (i) at least a portion of a first EKLF gene sequence; (ii) a loxP site; (iii) a polyA sequence; (iv) a selectable marker (e.g., neomycin resistance) gene sequence; (v) a promoter (e.g., PGK (phosphoglycerate kinase 1)) sequence; (vi) a loxP site; and (vii) at least a portion of a second EKLF gene sequence comprising a modification. In various embodiments, the first EKLF gene sequence comprises at least a portion of exon 1 and intron 1 of EKLF, and the second EKLF gene sequence comprises at least a portion of exon 2, intron 2 and exon 3 of EKLF, wherein exon 2 comprises a modification comprises a modified codon that encodes an amino acid residue not present in the endogenous EKLF protein, e.g., a modification of a sumoylation site or phosphorylation site in the EKLF protein. In particular embodiments, the portion of the first EKLF sequence and the portion of the second EKLF sequence are of a length sufficient to allow homologous recombination with an endogenous EKLF gene locus, e.g., at least 20 nucleotides, at least 50 nucleotides, or at least 100 nucleotides in length. In particular embodiments, the EKLF protein is a mouse EKLF protein, and in certain embodiments, the modified codon encodes a modification at amino acid position 74. In particular embodiments, the EKLF protein is a human EKLF protein, and in certain embodiments, the modified codon encodes a modification at amino acid position 54. In particular embodiments, the modified mouse exon 2 encodes a region of mouse EKLF polypeptide comprising an amino acid modification that prevents sumoylation or phosphorylation of the EKLF polypeptide. In particular embodiments, the modified mouse exon 2 encodes a region of mouse EKLF polypeptide comprising an amino acid substitution of lysine at position 74, e.g., substitution of lysine to arginine. In particular embodiments, the modification is any of those described herein.

In certain embodiments, the genetically modified animal expresses a modified EKLF polypeptide, wherein the modified EKLF polypeptide is modified from a wild-type EKLF of the same species as the animal. In certain embodiments, the genetically modified animal expresses a modified EKLF polypeptide, wherein the modified EKLF polypeptide is modified from a wild-type EKLF of a different species from the animal. In some embodiments, the modified EKLF polypeptide is modified from a mouse EKLF polypeptide (Accession: NP 034765.2; SEQ ID NO: 1). In some embodiments, the modified EKLF polypeptide is modified from a rat EKLF polypeptide (Accession: NP_001100634.1; SEQ ID NO: 2). In some embodiments, the modified EKLF polypeptide is modified from a human EKLF polypeptide (Accession: NP_006554.1; SEQ ID NO: 3). In some embodiments, the modified EKLF polypeptide is modified from a chimpanzee EKLF polypeptide (Accession: XP_524128; SEQ ID NO: 4). In some embodiments, the modified EKLF polypeptide is modified from a rhesus monkey EKLF polypeptide (Accession: NP_001181384 XP_001109612; SEQ ID NO: 5). In some embodiments, the modified EKLF polypeptide is modified from a dog EKLF polypeptide (Accession: XP_542040; SEQ ID NO: 6). In some embodiments, the modified EKLF polypeptide is modified from a cattle EKLF polypeptide (Accession: NP_001073828 XP_001251865; SEQ ID NO: 7). In particular embodiments, a modified EKLF locus, or a portion comprised in a vector described herein, is modified from a human EKLF gene sequence (Accession ENSMUSG00000105610; SEQ ID NO:9) or a mouse EKLF gene sequence (Accession ENSMUSG00000054191; SEQ ID NO:10), or a related gene. Portions of these sequences may be present in vectors of the present invention.

In some embodiments, the genetically modified non-human animal expresses a modified EKLF polypeptide that comprises at least one amino acid modification compared to wild-type EKLF. In particular embodiments, the transgenic animal expresses a polypeptide comprising one or more amino acid modifications as compared to a wild-type EKLF polypeptide. In some embodiments, the modified EKLF polypeptide comprises one, two, three, four, five, six, seven, eight, nine, ten, eleven, twelve, thirteen, fourteen, fifteen, sixteen, seventeen, eighteen, nineteen, twenty, greater than twenty, greater than twenty-five, greater than thirty, greater than thirty-five, greater than forty, greater than forty-five, or greater than fifty amino acid modifications as compared to a wild-type EKLF polypeptide. In some embodiments, the amino acid modifications are substitutions, additions, deletions, or a combination thereof.

In some embodiments, the genetically modified non-human animal expresses a modified EKLF polypeptide that comprises less than 100% identity to wild-type EKLF. In particular embodiments, the transgenic animal expresses a polypeptide greater than 80% identity, greater than 85% identity, greater than 90% identity, greater than 91% identity, greater than 92% identity, greater than 93% identity, greater than 94% identity, greater than 95% identity, greater than 96% identity, greater than 97% identity, greater than 98% identity, greater than 99% identity, but less than 100% identity to endogenous wild-type EKLF.

Particular embodiments contemplate that the function of the EKLF polypeptide is tightly regulated by interactions with different cofactor polypeptides and also by posttranslational modifications. EKLF associates with transcriptional activators such as p300, CBP, and P/CAF that have intrinsic histone acetyltransferase (HAT) activity, and EKLF itself is acetylated by p300 and CBP at two sites which results in its transcriptional activation. EKLF stability is regulated by its ubiquitination status (Quadrini, K. J., and J. J. Bieker. 2006. FEBS Lett. 580:2285-2293). Phosphorylation of threonine 41 is essential for optimal transcriptional activity (Ouyang, L., X. Chen, and J. J. Bieker. 1998. J. Biol. Chem. 273: 23019-23025.) Further, sumoylation at lysine 74 can regulate transcriptional repressor activity of EKLF (Siatecka et al. 2007 Mol Cell Biol.: 27(24): 8547-8560), and nuclear import of EKLF (Shyu et al. 2014. Developmental Cell 28, 409-422).

In certain embodiments, the transgenic animal expresses a modified EKLF polypeptide that has an altered, e.g. lacks, a post-translational modification compared to wild-type EKLF polypeptide. In particular embodiments, the transgenic animal expresses a modified EKLF polypeptide comprising at least one amino acid modification, wherein the at least one amino acid substitution prevents a post translational modification of the EKLF polypeptide at the site of the post-translational modification. In some embodiments, post-translational modification refers to the modification of a polypeptide during or after protein synthesis. Post translational modifications include, but are not limited to, phosphorylation, acetylation, methylation, glycosylation, lipidation, myristoylation, palmitoylation, farnesylation, geranylgeranylation, formylation, amidation, glypiation, lipoylation, acylation, butyrylation, malonylation, hydroxylation, S-nitrosylation, succinylation, sumoylation, ubiquitination, and Neddylation. In certain embodiments, the transgenic animal expresses a modified EKLF polypeptide with an amino acid modification that prevents or inhibits phosphorylation. In particular embodiments, the transgenic animal expresses a modified EKLF polypeptide with an amino acid that prevents or inhibits sumoylation. In certain embodiments, the transgenic animal is an EKLF knock-in mouse that expresses a modified EKLF polypeptide that has altered post-translational modification as compared to wild-type EKLF polypeptide.

"Phosphorylation," as used herein, refers to the addition of a phosphate ($PO_4^{3-}$) group to an amino acid residue of a polypeptide. Reversible protein phosphorylation, principally on serine, threonine or tyrosine residues, is one of the most important and well-studied post-translational modifications. Phosphorylation plays critical roles in the regulation of many cellular processes including cell cycle, growth, apoptosis and signal transduction pathways. In certain embodiments, the transgenic animal expresses a modified EKLF polypeptide comprising an amino acid modification that prevents phosphorylation of the modified EKLF polypeptide. In some embodiments, the modified EKLF polypeptide comprises an amino acid modification that prevents phosphorylation on the modified amino acid residue.

"Sumoylation", also referred to in the art as "SUMOylation," is the covalent linkage of a polypeptide to the SUMO protein (Small Ubiquitin-related MOdifier). SUMO proteins are a family of small proteins that are covalently attached to and detached from other proteins in cells to modify their function. Sumoylation is a post-translational modification involved in various cellular processes, such as nuclear-cytosolic transport, transcriptional regulation, apoptosis, protein stability, response to stress, and progression through the cell cycle. In certain embodiments, the transgenic animal expresses a modified EKLF polypeptide comprising an amino acid modification that prevents summolaytion of the modified EKLF. In some embodiments, the modified EKLF polypeptide comprises an amino acid modification that prevents sumoylation on the modified amino acid residue.

Particular embodiments contemplate that EKLF polypeptide is post-translationally modified by sumoylation at a single site, and that the E3 ligase PIAS1 plays a critical role in this process. Certain embodiments contemplate that the EKLF polypeptide is sumoylated at lysine at position 74 in mice, at lysine at position 54 in humans, or at a corresponding sumoylation site. Particular embodiments contemplate that the human EKLF polypeptide is sumoylated at lysine at position 54. In certain embodiments, a sumoylation site that corresponds to lysine at position 74 of the mouse EKLF polypeptide is lysine at position 54 of the human EKLF polypeptide. Some embodiments contemplate that modification to lysine 74 in mouse EKLF polypeptide, to lysine 54 in human EKLF polypeptide, or to a corresponding sumoylation site in other EKLF polypeptides, prevents sumoylation of the EKLF polypeptide. In particular embodiments, the genetically modified animal expresses a modified EKLF polypeptide that comprises a modification of lysine 74, or a corresponding sumoylation site, that prevents sumoylation of the modified EKLF polypeptide. In particular embodiments, the modification is a substitution. In certain embodiments, the modification is a lysine to arginine substitution at position 74 in mouse EKLF polypeptide.

Particular embodiments contemplate that phosphorylation of serine at position 68 in mice, or a corresponding phosphorylation site, by PKC theta triggers the summoylation of the EKLF polypeptide. Some embodiments contemplate that an amino acid modification that prevents the phosphorylation of EKLF at serine 68 prevents or reduces the likelihood of EKLF sumoylation at the lysine at position 74. In certain embodiments, the genetically modified animal expresses a modified EKLF polypeptide that comprises an amino acid modification that prevents phosphorylation at serine 68 and reduces or prevents sumoylation of the modified EKLF polypeptide. In certain embodiments, the genetically modified animal expresses a modified EKLF polypeptide comprising an amino acid modification at position 68 that prevents phosphorylation at position 68 and reduces or prevents sumoylation of the modified EKLF polypeptide. In particular embodiments, the modification is a substitution. In certain embodiments, the modification is a serine to alanine substitution at position 68.

Certain embodiments contemplate that the human EKLF polypeptide comprises one or more phosphorylation sites. In particular embodiments, phosphorylation at a phosphorylation site of the human EKLF polypeptide triggers the sumoylation of the human EKLF polypeptide. Some embodiments contemplate that an amino acid modification that prevents the phosphorylation of human EKLF polypeptide prevents or reduces the likelihood of EKLF sumoylation at the lysine at position 54. In certain embodiments, a modified human EKLF comprises an amino acid modification at a phosphorylation site that prevents phosphorylation and reduces or prevents sumoylation of the modified human EKLF polypeptide.

In some embodiments, the genetically modified non-human animal expresses a modified EKLF polypeptide that comprises a modification of at least one amino acid, wherein the modification of the at least one amino acid prevents or reduces sumoylation of the EKLF polypeptide. In some embodiments, the genetically modified non-human animal expresses a modified EKLF polypeptide that comprises a modification of at least one amino acid, wherein the modification of the at least one amino acid prevents sumoylation of the EKLF polypeptide. In some embodiments, the modification of the at least one amino acid reduces the amount of modified EKLF polypeptides that are sumoylated as compared to wild-type EKLF polypeptide. In some embodiments, the modification of the at least one amino acid reduces the amount of modified EKLF polypeptides that are sumoylated by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between) compared to the wild-type EKLF polypeptide. In some embodiments, the modification of the at least one amino acid reduces the probability that a modified EKLF polypeptide will be sumoylated. In some embodiments, the modification of the at least one amino acid reduces the probability that a modified EKLF polypeptide will be sumoylated by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between).

In some embodiments, the genetically modified non-human animal expresses a modified EKLF polypeptide that comprises a modification of at least one amino acid, wherein the modification of at least one amino acid prevents or reduces phosphorylation of the EKLF polypeptide. In some embodiments, the genetically modified non-human animal expresses a modified EKLF polypeptide that comprises a modification of at least one amino acid, wherein the modification of at least one amino acid prevents phosphorylation of the EKLF polypeptide. In some embodiments, the modification of the at least one amino acid reduces the amount of modified EKLF polypeptides that are phosphorylated compared to wild-type EKLF polypeptide. In some embodiments, the modification of the at least one amino acid reduces the amount of modified EKLF polypeptides that are phosphorylated by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between) compared to the wild-type EKLF polypeptide. In some embodiments, the modification of the at least one amino acid reduces the probability that a modified EKLF polypeptide will be sumoylated. In some embodiments, the modification of the at least one amino acid reduces the probability that a modified EKLF polypeptide will be sumoylated by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between).

In some embodiments, the genetically modified non-human animal expresses a modified EKLF polypeptide that comprises a modification of an amino acid, wherein the modification of the amino acid prevents phosphoryation of the modified EKLF polypeptide at serine 68, or a corresponding phosphorylation site. In some embodiments, the genetically modified non-human animal expresses a modified EKLF polypeptide that comprises a modification of serine 68, or a corresponding phosphorylation site, wherein the modification prevents phosphorylation of sumoylation of the EKLF polypeptide. In certain embodiments, the modification is a serine to alanine substitution at position 68, or a corresponding phosphorylation site. In some embodiments, the modification that prevents phosphorylation of serine 68, or a corresponding phosphorylation site, reduces the amount of modified EKLF polypeptides that are sumoylated. In some embodiments, the modification of the at least one amino that prevents phosphorylation of serine 68, or a corresponding phosphorylation site, reduces the amount of modified EKLF polypeptides that are sumoylated by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between) compared to wild-type EKLF polypeptide. In some embodiments, the modification that prevents phosphosphorylation of the amino acid at position 68, or a corresponding or different phosphorylation site, reduces the probability that a modified EKLF polypeptide will be sumoylated by about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between) compared to wild-type EKLF polypeptide.

Certain embodiments contemplate that a modified EKLF polypeptide expressed by a genetically modified animal may have altered properties or activities, e.g. stability, subcellular localization, or transcriptional activity, as compared to a wild-type EKLF polypeptide depending on the cell-type or tissue-type where the modified EKLF polypeptide is expressed. Thus, in a given cell-type or tissue-type of the genetically modified animal, the property of the modified EKLF polypeptide may be similar to or different from the property of the wild-type EKLF polypeptide in the equivalent cell or tissue. Therefore, in some embodiments, the genetically modified animal comprises a cell-type or tissue-type where the property or activity of the modified EKLF polypeptide is different from the wild-type EKLF polypeptide and also comprises a cell-type or tissue-type where the same property or activity of the modified EKLF polypeptide is similar to the wild-type EKLF polypeptide. In particular embodiments, a property or activity of the modified EKLF polypeptide is different from the wild-type EKLF polypeptide in all of the cell-types and tissue-types of the genetically modified animal where EKLF is expressed.

Some embodiments contemplate that the modification of the EKLF polypeptide does not alter the expression of the modified EKLF polypeptide compared to the endogenous, wild-type EKLF polypeptide. Some embodiments contemplate that in a given cell or tissue of the genetically modified animal, the levels of mRNA encoding modified EKLF polypeptide will be similar to the levels of mRNA encoding wild-type EKLF polypeptide in an equivalent cell or tissue type of a control animal, e.g. a littermate of the same gender. Particular embodiments contemplate that in a given cell or tissue of the genetically modified animal, the levels of the modified EKLF polypeptide will be similar to the levels of mRNA encoding wild-type EKLF polypeptide in an equivalent cell or tissue type of a non-genetically modified animal of the same species.

In some embodiments, the genetically modified animal expresses a modified EKLF polypeptide, wherein the modification alters the stability of the modified EKLF compared to an endogenous, wild-type EKLF polypeptide. In some embodiments, the modification of the EKLF polypeptide increases the half-life of the modified EKLF by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 200%, or by about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold, or by greater than 10-fold (including all integers and ranges in between), compared to the endogenous, wild-type EKLF polypeptide. In some embodiments, the modification of the EKLF polypeptide reduces the half-life of the modified EKLF by about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between) compared to the wild-type EKLF polypeptide.

In some embodiments, the genetically modified animal expresses a modified EKLF polypeptide, wherein the modification alters the subcellular localization of the modified EKLF compared to an endogenous, wild-type EKLF polypeptide. In some embodiments, the modification of the EKLF polypeptide increases the cytosolic localization of the modified EKLF by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 200%, or by about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold, or by greater than 100-fold (including all integers and ranges in between), compared to the endogenous, wild-type EKLF polypeptide. In some embodiments, the modification of the EKLF polypeptide reduces the nuclear localization of the modified EKLF by about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between) as compared to the wild-type EKLF polypeptide. In particular embodiments, subcellular localization of the modified EKLF polypeptide is altered in the progenitors and precursor cells of the erythroid lineage. In some embodiments, subcellular localization is altered in cells undergoing erythroid maturation during the transition from pro-erythroblast (Pro-E) to basophilic erythroblast (Baso-E). In certain embodiments, subcellular localization is altered during or following DMSO-induced murine erythroleukemia (MEL) cell differentiation.

In some embodiments, the genetically modified animal expresses a modified EKLF polypeptide, wherein the modification increases the transcriptional activation activity, i.e. the promotion of transcription of a target gene or genes, of the modified EKLF compared to an endogenous, wild-type EKLF polypeptide. In some embodiments, the modified EKLF polypeptide increases the transcription of at least one gene by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 200%, or by about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold, or by greater than 100-fold (including all integers and ranges in between) as compared to the transcription of the gene promoted by the wild-type EKLF. In some embodiments, the modified EKLF polypeptide promotes an increase in transcription of one, two, three, four, five, six, seven, eight, nine, ten, greater than ten, greater than fifteen, greater than twenty, greater than twenty-five, greater than thirty, greater than forty, greater than fifty, greater than sixty, greater than seventy, greater than eighty, greater then ninety, greater than 100, greater than 200, greater than 300, greater than 400, greater then 500, or greater than 1,000 genes that are not transcriptionally promoted by the wild-type EKLF polypeptide.

In some embodiments, the genetically modified animal expresses a modified EKLF polypeptide, wherein the modification increases the transcriptional repression activity, i.e. repression of transcription of a target gene or genes, of the modified EKLF compared to an endogenous, wild-type EKLF polypeptide. In some embodiments, the modified EKLF polypeptide represses the transcription of at least one gene by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 200%, or by about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold, or by greater than 100-fold (including all integers and ranges in between) as compared to the transcription of the gene promoted by the wild-type EKLF. In some embodiments, the modified EKLF polypeptide represses the transcription of one, two, three, four, five, six, seven, eight, nine, ten, greater than ten, greater than fifteen, greater than twenty, greater than twenty-five, greater than thirty, greater than forty, greater than fifty, greater than sixty, greater than seventy, greater than eighty, greater then ninety, greater than 100, greater than 200, greater than 300, greater than 400, greater then 500, or greater than 1,000 genes that are not repressed by the wild-type EKLF polypeptide.

In some embodiments, the genetically modified animal expresses a modified EKLF polypeptide, wherein the modification decreases the transcriptional activation activity, i.e. the promotion of transcription of a target gene or genes, of the modified EKLF compared to an endogenous, wild-type EKLF polypeptide. In some embodiments, the modified EKLF polypeptide decreases the transcription of at least one gene by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between) as compared to the transcription of the gene promoted by the wild-type EKLF. In some embodiments, the modified EKLF polypeptide promotes an increase in transcription of one, two, three, four, five, six, seven, eight, nine, ten, greater than ten, greater than fifteen, greater than twenty, greater than twenty-five, greater than thirty, greater than forty, greater than fifty, greater than sixty, greater than seventy, greater than eighty, greater then ninety, greater than 100, greater than 200, greater than 300, greater than 400, greater then 500, or greater than 1,000 less genes that are transcriptionally promoted by the wild-type EKLF polypeptide.

In some embodiments, the genetically modified animal expresses a modified EKLF polypeptide, wherein the modification decreases the transcriptional repression activity, i.e. repression of transcription of a target gene or genes, of the modified EKLF compared to an endogenous, wild-type EKLF polypeptide. In some embodiments, the modified EKLF polypeptide reduces the repression of the transcription of at least one gene by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between) as compared to the transcription of the gene repressed by the wild-type EKLF polypeptide. In some embodiments, the modified EKLF polypeptide represses the transcription of one, two, three, four, five, six, seven, eight, nine, ten, greater than ten, greater than fifteen, greater than twenty, greater than twenty-five, greater than thirty, greater than forty, greater than fifty, greater than sixty, greater than seventy, greater than eighty, greater then ninety, greater than 100, greater than 200, greater than 300, greater than 400, greater then 500, or greater than 1,000 less genes that are repressed by the wild-type EKLF polypeptide.

Certain embodiments are directed to genetically modified animals that express modified EKLF polypeptide with enhanced lifespan, health span, and/or cancer resistance compared to control animals that express wild-type EKLF polypeptide. Particular embodiments contemplate a model whereby the enhancement of lifespan, health span, and/or cancer resistance are conferred by the modified EKLF polypeptide through a mechanism that is distinct from existing animal models of longevity and cancer resistance. This model is based on observations that phenotypes observed in the animals expressing modified EKLF are distinct from the phenotypes observed in previously described models of longevity, e.g. calorie restricted animals, animal administered metformin, IGF1 receptor knockout animals, transgenic PTEN animals, Heterozygous Myc knockout animals, animals administered rapamycin, S6K1 knockout animals, Fat10 knockout animals, Sirt1 mutant animals, and transgenic Cisd2 animals. Particular embodiments contemplate that expression of modified EKLF polypeptides extends lifespan and health span without altering one or more of metabolism, fertility, autophagy homeostasis, genomic stability, or mitochondrial function.

In some embodiments, genetically modified animals that express modified EKLF polypeptide have increased lifespan compared to control animals that express wild-type EKLF polypeptide. In particular embodiments, the increased lifespan is manifested as an increase in the mean lifespan compared to control animals. In certain embodiments, the increased lifespan is manifested as an increase in the maximum age the animal can reach compared to control animals. In some embodiments, the increased lifespan is manifested as an increase in the maximum lifespan, i.e. the mean lifespan of the longest-lived 10% of a population. In particular embodiments, genetically modified animals that express modified EKLF polypeptide have increased lifespan of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 45%, about 50%, about 55%, about 60%, about 65%, about 70%, about 75%, about 80%, about 85%, about 90%, about 95%, or about 100% (including all integers and ranges in between) as compared to control animals that express wild-type EKLF.

In some embodiments, genetically modified animals that express modified EKLF polypeptide have increased health span compared to control animals that express wild-type EKLF polypeptide. Health span refers to the length of time where the organism is in optimal health, e.g. free from age-related diseases. In particular embodiments, genetically modified animals that express modified EKLF polypeptide have increased health span of about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 45%, about 50%, about 55%, about 60%, about 65%, about 70%, about 75%, about 80%, about 85%, about 90%, about 95%, about 100% (including all integers and ranges in between), or greater than 100%, as compared to control animals that express wild-type EKLF. Increased health span may be measured with respect to one or more physical attributes associated with increased health, including but not limited to any of those described herein.

In certain embodiments, genetically modified animals that express modified EKLF polypeptide have delayed onset and/or slower progression of aging-related symptoms. In particular embodiments, aged genetically modified animals show less severity of at least one aging-related symptoms, e.g. gray hairs, muscle weakness, motor coordination, osteoporosis, loss of balance, cancer incidence, susceptibility to chemical stress, susceptibility to infection, or susceptibility to inflammation, than aged-matched controls. In particular embodiments, genetically modified animals expressing modified EKLF polypeptide experience a delayed onset of aging relating symptoms, as compared to as compared to age-matched control animals. In certain embodiments, genetically modified animals expressing modified EKLF polypeptide experience a slower progression of aging relating symptoms, as compared to as compared to age-matched control animals.

In certain embodiments, genetically modified animals that express modified EKLF polypeptide have a delayed onset and/or a slower progression of age-related changes, e.g., in muscle strength and motor coordination. Particular embodiments contemplate that normal aging is accompanied by progressive weakness and loss of motor coordination. In certain embodiments, young genetically modified animals that express modified EKLF polypeptide have similar muscle strength and motor coordination as young control animals that express wild-type EKLF polypeptide; and aged genetically modified animals that express modified EKLF polypeptide greater muscle strength and motor coordination as compared to young control animals that express wild-type EKLF polypeptide. In particular embodiments, genetically modified animals that express modified EKLF retain about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about greater than 80%, about greater than 85%, about greater than 90%, about greater than 95%, about greater than 99%, of their muscle strength and motor coordination throughout the progression of their lifespan. Those of skill in the art will recognize methods suitable for measuring and evaluating muscle strength and motor coordination, including but not limited to the rotarod test and the grip strength test.

In certain embodiments, aged genetically modified animals that express modified EKLF have increased muscle strength of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 200%, or by about 2-fold, about 3-fold, about 4-fold, about 5-fold, about 6-fold, about 7-fold, about 8-fold, about 9-fold, about 10-fold (including all ranges and integers in between), or about greater than 10-fold compared to age-matched control animals. In particular embodiments, aged genetically modified animals that express modified EKLF have increased motor coordination as compared to age-matched control animals of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 200%, or by about 2-fold, about 3-fold, about 4-fold, about 5-fold, about 6-fold, about 7-fold, about 8-fold, about 9-fold, about 10-fold (including all ranges and integers in between), or about greater than 10-fold.

Particular embodiments contemplate that osteoporosis can develop as a symptom of normal aging, and that normal aging can be accompanied by a reduction in bone volume and trabecular number, and an increase in trabecular spacing. In certain embodiments, genetically modified animals that express modified EKLF do not develop osteoporosis during the progression of their lifespan. In some embodiments, genetically modified animals that express modified EKLF do not experience a reduction in bone volume and/or trabecular number throughout the progression of their lifespan. In some embodiments, genetically modified animals that express modified EKLF do not experience an increase in trabecular spacing throughout the progression of their lifespan. In certain embodiments, genetically modified animals that express modified EKLF have slower rate of development of osteoporosis during the progression of their lifespan as compared to age-matched control animal that express wild-type EKLF. In some embodiments, genetically modified animals that express modified EKLF have a slower progression of the reduction in bone volume and/or trabecular number throughout the progression of their lifespan as compared to age-matched control animals. In some embodiments, genetically modified animals that express modified EKLF have a slower progression of the increase in trabecular spacing throughout the progression of their lifespan.

In certain embodiments, aged genetically modified animals that express modified EKLF have increased bone volume of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 200%, or by about 2-fold, about 3-fold, about 4-fold, about 5-fold, about 6-fold, about 7-fold, about 8-fold, about 9-fold, about 10-fold (including all ranges and integers in between), or about greater than 10-fold compared to age-matched control animals. In certain embodiments, aged genetically modified animals that express modified EKLF have increased trabecular number of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 110%, about 120%, about 130%, about 140%, about 150%, about 200%, or by about 2-fold, about 3-fold, about 4-fold, about 5-fold, about 6-fold, about 7-fold, about 8-fold, about 9-fold, about 10-fold (including all ranges and integers in between), or about greater than 10-fold compared to age-matched control animals. In certain embodiments, aged genetically modified animals that express modified EKLF have decreased trabecular spacing by about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between) as compared to age-matched control animals.

Particular embodiments contemplate that genetically modified animals that express a modified EKLF polypeptide have a lower probability of developing a cellular proliferative disorder, i.e. cancer, throughout their lifespan as compared to control animals that express wild-type EKLF. In some embodiments, a genetically modified animal expressing a modified EKLF polypeptide has a reduced probability of developing cancer throughout its lifetime of about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between) compared to a control animal. In particular embodiments, the genetically modified animal is less likely to develop a cellular proliferative disorder selected from liver cancer, colon cancer, breast cancer, prostate cancer, hepatocellular carcinoma, melanoma, lung cancer, glioblastoma, brain tumor, hematopoietic malignancies, retinoblastoma, renal cell carcinoma, head and neck cancer, cervical cancer, pancreatic cancer, esophageal cancer, or squama cell carcinoma compared to an aged matched control. In some embodiments, the genetically modified animal that expresses modified EKLF has a lower probability of developing melanoma over its lifespan than a control animal.

Certain embodiments contemplate that the expression of modified EKLF polypeptide by a genetically modified animal suppresses the growth of a tumor or cancer, or suppresses the ability of a tumor, cancer cell or precancerous cell to undergo metastasis. Some embodiments contemplate that the expression of modified EKLF polypeptide by a genetically modified animal suppresses the ability of a tumor, cancer cell or precancerous cell to undergo metastasis, but does not alter the rate of tumor growth. Particular embodiments contemplate that the intravenous injection of precancerous or cancer cells, e.g. B16F10 melanoma cells, into a genetically modified animal that expresses modified EKLF polypeptide will result in cancer metastasis and tumor formation that are significantly reduced compared to control animals intravenously injected with precancerous or cancer cell. In certain embodiments, a cancer cell or precancerous cell has a reduced likelihood of forming a tumor in a genetically modified animal that expresses modified EKLF as compared to a cancer cell or precancerous cell in a control animal. In particular embodiments, a cancer cell or precancerous cell has reduced incidence of metastasis in a genetically modified animal that expresses modified EKLF as compared to a cancer cell or precancerous cell in a control animal. In some embodiments, the cancer cell or precancerous cell does not comprise a modification at the EKLF locus and does not express modified EKLF.

In some embodiments, a precancerous or cancer cell is in a genetically modified animal that expresses a modified EKLF polypeptide, and growth or metastasis of the cell is reduced by about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between) compared to an equivalent cell in a control animal. In some embodiments, the precancerous or cancer cell is intravenously injected into the genetically modified animal. In some embodiments, the cell is a B16F10 melanoma cell.

In some embodiments, a precancerous or cancer cell is in a genetically modified animal that expresses a modified EKLF polypeptide, and the number of tumors the cell can form is reduced by about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, or about 100% (including all integers and ranges in between) compared to an equivalent cell in a control animal. In some embodiments, the precancerous or cancer cell is intravenously injected into the genetically modified animal. In some embodiments, the cell is a B16F10 melanoma cell.

Particular embodiments are directed to an EKLF knock-in mouse that expresses a modified EKLF polypeptide, wherein the modified EKLF polypeptide comprises at least one amino acid modification that prevents sumoylation of the modified EKLF polypeptide, and wherein the EKLF knock-in mouse has enhance longevity, extended health span, and/or resistance to tumorigenesis and cancer metastasis. Certain embodiments are directed to an EKLF knock-in mouse that expresses a modified EKLF polypeptide, wherein the modified EKLF polypeptide comprises a lysine to arginine substitution at position 74, wherein the EKLF knock-in mouse has enhance longevity, extended health span, and/or resistance to tumorigenesis and cancer metastasis.

Methods of Identifying Agents that Enhance Longevity and/or Decrease Tumorigenicity or Tumor Metastasis The present invention includes methods for identifying active agents that confer increased longevity, extended life span, extended health span, decreased tumorigenesis, and/or decreased tumor metastasis to a subject, e.g., a mammal such as a human. Such methods of the invention are based on the unexpected finding that modifications of EKLF have these effects in mammals. As described herein, the term "tumorigenesis" refers to the initiation or onset of a tumor, i.e., the occurrence of a tumor. The composition and methods described herein may also be used to achieve, or retain for a longer period of time, a specific phenotype or characteristic associated with youthfulness or increased longevity, including any of those described or demonstrated herein, such as reduced graying of the hair, increased motor coordination, increased muscle strength, reduced muscle weakness, increased motor coordination, reduced osteoporosis, greater bone volume, greater bone density, greater trabecular number, reduced trabecular spacing, reduced loss of balance, e.g., as compared to untreated subjects of the same age.

Accordingly, the methods described below may be used to identify active agents that confer any of these phenotypes or characteristics to a treated subject.

In certain embodiments, a method of identifying an active agent capable of increasing longevity, life span or health span and/or inhibiting tumorigenesis or tumor metastasis of a subject comprises identifying an agent that alters one or more post-translational modifications of an EKLF polypeptide, e.g., a human EKLF protein. In particular embodiments, the post-translational modification is sumoylation or phosphorylation. Reversible post-translational modifications including sumoylation and phosphorylation play important roles in the nucleic import of certain proteins, including EKLF. It has been shown that murine EKLF is sumoylated at Lys74, which is located within a consensus negatively charged amino acid-dependent sumoylation motif. The corresponding sumoylation site of human EKLF is located at Lys54. Without wishing to be bound to any particular theory, it is thought that sumoylation may or may not reduce nuclear translocation of EKLF. In addition, it is thought that sumoylation may alter the transcriptional activity, e.g., activator or repressor activity, of EKLF on one or more EKLF target genes.

Small ubiquitin related modifier (SUMO) was discovered as a modifier of mammalian proteins (Sarge, K. and Parke-Sarge, O-K., Methods in Mol. Biol. 2009; 590: 265-277 (2010)). As described therein, protein sumoylation does not promote degradation of proteins but instead regulates functional properties of target proteins, such as subcellular localization, protein partnering, and transactivation functions of transcription factors. SUMO proteins are covalently attached to lysine residues of proteins, which are generally found within the consensus motif $\Psi$KXE where $\Psi$ is a hydrophobic amino acid and X is any residue. The covalent attachment of SUMO to other proteins involves a series of enzymatic steps in vivo. First, the SUMO proteins undergo proteolytic processing near their C-terminal end to form the mature proteins, a step which is performed by SUMO proteases (Ulp's). These proteases are dual-functional, as they are also responsible for cleaving SUMO groups from substrate proteins by cleaving the isopeptide bonds by which they are joined. The mature processed SUMO protein is covalently attached via a thioester bond to the SAE2 (Uba2) subunit of the heterodimeric SUMO E1 activating enzyme in an ATP-dependent reaction). The SUMO moiety is transferred from the E1 to ubc9, the SUMO E2 enzyme, which then binds to the $\Psi$KXE consensus sequence in target proteins and forms an isopeptide bond between the ε-amino group of the lysine within this sequence and the carboxyl group of the C-terminal glycine of the SUMO polypeptide. SUMO E3 proteins have been identified that enhance the efficiency of SUMO attachment by interacting with both ubc9 (the E2 enzyme) and the substrate, thereby acting as bridging factors. Vertebrate cells contain three SUMO paralogs. SUMO-2 and SUMO-3 are very similar to each other in sequence, and have approximately 50% sequence identity with SUMO-1, which is the best characterized of the three vertebrate SUMO proteins.

The protein kinase C theta (PKCΘ)-mediated Ser68 phosphorylation site of EKLF is close to Lys74, and it has been hypothesized that Ser68 phosphorylation coupled sumoylation at Lys74 facilitates the nuclear import of EKLF, and that Ser68 phosphorylation of EKLF might not only dissociate EKLF from FOE, but it might also affect the sumoylation of EKLF, playing a regulatory role in the nuclear import of EKLF during erythroid maturation (Yang et al. (2006) EMBO J. 25, 5083-5093). Without wishing to be bound to any particular theory, it is believed that active agents that inhibit phosphorylation of Ser68 or sumoylation of Lys74 may or may not inhibit the translocation of EKLF to the nucleus, thus affecting its ability to transcriptionally activate or repress target genes. In addition, it is thought that active agents that inhibit phosphorylation of Ser68 or sumoylation of Lys74 may alter the transcriptional activity, e.g., activator or repressor activity, of EKLF on one or more EKLF target genes.

In one embodiment, a method of identifying an active agent comprises: contacting an EKLF polypeptide, e.g., a human EKLF protein, with a candidate agent; and measuring an amount of a post-translational modification present on the EKLF polypeptide, wherein the candidate agent is considered an active agent if the measured amount of the post-translational modification on the EKLF polypeptide is significantly different than (e.g., less than) a predetermined amount or significantly different than (e.g., less than) the amount on a control EKLF polypeptide that was not contacted with the candidate agent. In particular embodiments, the method further comprises measuring an amount of post-translational modification present on the EKLF polypeptide not contacted with the candidate agent. In particular embodiments, the pre-determined amount is zero, or the pre-determined amount indicates that less than 10%, less than 20%, or less than 50% or the EKLF polypeptide contains the post-translational modification.

In various embodiments, the EKLF polypeptide is contacted with the candidate agent before and/or while performing an assay to detect the presence of the post-translational modification, e.g., an in vitro phosphorylation or sumoylation assay. In particular embodiments, the assay comprises contacting an EKLF polypeptide with the enzyme(s) that performs the post-translational modification of the EKLF polypeptide, e.g., in the presence of a chemical group that is attached to the EKLF polypeptide, such as a phosphate group or a SUMO protein, for a time sufficient and under conditions that allow the post-translational modification to occur, and then determining the amount of EKLF polypeptide that comprises the post-translational modification or the amount of the post-translational modification present on the EKLF polypeptide. The EKLF polypeptide may be contacted with various amounts of the candidate agent, e.g., to measure an IC50 for the candidate agent.

In particular embodiments wherein the post-translational modification is sumoylation, the ELKL polypeptide is contacted with the candidate agent either before or while performing an in vitro sumoylation assay. Such assays are known in the art and kits for performing such assays are available, e.g., ENZO Sumoylation Kit (Farmingdale, N.Y., USA). In particular embodiments, the EKLF polypeptide is contacted with the candidate agent in the presence of SUMO-1, -2, and/or -3 under conditions and for a time sufficient to allow sumoylation, and then SUMO specific antibodies are used to detect sumoylated EKLF protein, e.g., via SDS-PAGE or Western blotting.

In certain embodiments wherein the post-translational modification is sumoylation, an EKLF polypeptide is in vitro translated in the presence of a radioactive label (e.g., $^{35}$S-Met) and then contacted with the candidate agent before or while incubated in a reaction containing the SUMO E1 and E2 enzymes and SUMO-1 under conditions and for a time sufficient to allow sumoylation of the EKLF polypeptide, followed by SDS-PAGE and autoradiography to determine whether a sumoylated form of the EKLF polypeptide is present or not.

In certain embodiments wherein the post-translational modification is phosphorylation, EKLF polypeptide is in vitro translated in the presence of a radioactive label (e.g., $^{35}$S-Met) is contacted with the candidate agent before or while incubated with PKCΘ and phosphate group under conditions and for a time sufficient to allow phosphorylation of the EKLF polypeptide, and then analyzed by autoradiography or IB. Alternatively, phosphorylated protein may be isolated by SDS-PAGE and analyzed by mass spectrometry. Related methods are described in Shyu, Y-C. et al., (2014) Developmental Cell 28: 409-422.

In another embodiment, a method of identifying an active agent comprises: contacting a cell comprising an EKLF polypeptide with a candidate agent; and measuring an amount of a post-translational modification present on the EKLF polypeptide, wherein the candidate agent is considered an active agent if the measured amount of the post-translational modification on the EKLF polypeptide is significantly different than (e.g., less than) a predetermined amount or significantly different than (e.g. less than) the amount on a control EKLF polypeptide that was not contacted with the candidate agent. In particular embodiments, the method further comprises measuring an amount of post-translational modification present on the EKLF polypeptide not contacted with the candidate agent.

In various embodiments, the cell comprising the EKLF polypeptide comprises an exogenously introduced EKLF polypeptide, e.g., a human EKLF protein. In certain embodiments, the cell comprises an expression vector that expresses the exogenous EKLF protein. The expression vector may be stably integrated into the cell's genome or transiently present in the cell. In certain embodiments, EKLF protein is introduced into the cell by microinjection or the use of a lipid delivery vehicle. In particular embodiments, the assay comprises contacting the cell comprising the EKLF polypeptide with an agent that promotes or stimulates the post-translational modification of the EKLF polypeptide, e.g. PMA, EPO, PKC theta activators, or SUMO polypeptides, for a time sufficient and under conditions that allow the post-translational modification to occur, and then determining the amount of EKLF polypeptide that comprises the post-translational modification or the amount of the post-translational modification present on the EKLF polypeptide. The cell comprising the EKLF polypeptide may be contacted with various amounts of the candidate agent, e.g., to measure an IC50 for the candidate agent.

In particular embodiments wherein the post-translational modification is sumoylation, the polypeptide or cell is contacted with the active agent under conditions and for a time sufficient for sumoylation of the EKLF polypeptide to occur, and then a sumoylation assay is performed. Such assays are known in the art, e.g. in vivo sumoylation assays. For example, the cell may then be lysed and sumoylated proteins detected by immunoprecipitation (IP) analysis using a primary antibody that binds to EKLF, species-matched non-specific IgG, and antibodies against SUMO-1, SUMO-2, or SUMO-3 (Invitrogen). Other methods that may be employed include but are not limited to in vivo IP-Western blotting, IP-MS, DNA transfection, DNA transfection-IP-Western blotting. Illustrative methods are also described in Sarge, K. and Parke-Sarge, O-K., Methods in Mol. Biol. 2009; 590: 265-277 (2010)).

In certain embodiments wherein the post-translational modification is phosphorylation, a polypeptide or cell is contacted with the active agent under conditions and for a time sufficient for phosphorylation of the EKLF polypeptide to occur, and then phosphorylated EKLF protein is detected using any of a variety of assays known and available in the art e.g., in vitro phospholylation. For example, the cell may be lysed and phosphorylated EKLF protein detected by immunoprecipitation analysis using a primary antibody that binds specifically to the phosphorylated form of EKLF (phosphorylated at Ser68), and a detectable secondary antibody. Other illustrative methods that may be employed include in vivo IP-Western blotting, IP-MS, DNA transfection, DNA transfection-IP-Western blotting, and Western blotting.

In various embodiments that include measuring the amount of a post-translational modification on an EKLF polypeptide, the post-translational modification is sumoylation or phosphorylation. In particular embodiments, it is sumoylation of murine EKLF Lys74 or human EKLF Lys54 or phosphorylation of murine EKLF Ser68. In particular embodiments, it is phosphorylation by P-PKCΘ(5676). Methods of determining the presence of or an amount of sumoylation or phosphorylation of a polypeptide are known and available in the art. For example, illustrative methods that may be employed are described in Yang et al. (2006) EMBO J. 25, 5083-5093; Shyu et al. (2006) Cell Res. 16, 347-355; Siatecka et al. (2007) Mol Cell Biol. 27(24):8547-60; and Shyu, et al. (2014) Developmental Cell, 28, 409-422.

In certain embodiments that include measuring the amount of a post-translational modification on an EKLF polypeptide, the candidate agent is determined to be an active agent if the amount of the post-translational modification present on the EKLF polypeptide contacted with the candidate agent is less than 90%, less than 80%, less than 70%, less than 60%, less than 50%, less than 40%, less than 30%, less than 20%, less than 10%, or 0% as compared to the amount on the EKLF polypeptide not contacted with the candidate agent. In certain embodiments, the candidate agent is determined to be an active agent if the amount of the post-translational modification present on the EKLF polypeptide is less than or equal to a pre-determined cut-off value, which may be determined using agents know to inhibit phosphorylation or sumoylation. In particular embodiments, the pre-determined cut-off value is zero.

In certain embodiments, a method of identifying an active agent capable of increasing longevity, life span or health span and/or inhibiting tumorigenesis or tumor metastasis of a subject comprises identifying an agent that alters one or more activities of an EKLF polypeptide, e.g., a human EKLF protein. In particular embodiments, the activity is nuclear translocation, transcriptional activation or transcriptional repression. Data suggests that in the progenitors and precursor cells of the erythroid lineage, EKLF is located mainly in the cytoplasm, and it is translocated from the cytoplasm to the nucleus during erythroid maturation (Yang et al. (2006) EMBO J. 25, 5083-5093). Without wishing to be bound to any particular theory, it is believed that nuclear import of EKLF is necessary for effective activation of adult globin gene transcription. An EKLF-interacting factor, Foe of EKLF (FOE) interacts with and sequesters EKLF in the cytoplasm, thus determining the functional restriction of EKLF in erythroid progenitor cells, which in turn regulates the activation or repression by EKLF of a set of erythroid genes during CFU-E/Pro-E to Baso-E transition of the erythroid lineage.

In another embodiment, a method of identifying an active agent comprises: contacting a cell comprising an EKLF polypeptide, e.g., a human EKLF protein, with a candidate agent; and measuring an amount of an activity of the EKLF polypeptide, wherein the candidate agent is considered an active agent if the measured amount of the activity the EKLF polypeptide is significantly different than (e.g., more than or less than) a predetermined amount or significantly different than (e.g., more than or less than) the amount of a control EKLF polypeptide that was not contacted with the candidate agent. In particular embodiments, the method further comprises measuring an amount of an activity of the EKLF polypeptide not contacted with the candidate agent. In certain embodiments, the methods are practiced using an EKLF polypeptide instead of cells comprising an EKLF polypeptide, e.g., when the activity is transactivator activity or repressor activity.

Methods of determining nuclear localization of a polypeptide are known and available in the art. For example, methods that may be employed are described in Yang et al. (2006) EMBO J. 25, 5083-5093, such as determining the subcellular (e.g., cytoplasmic or nuclear) localization of the EKLF polypeptide by immunofluorescence. Accordingly, in one method, a cell comprising an EKLF polypeptide is contacted with a candidate agent under conditions and for a time sufficient for nuclear localization, and then the subcellular localization of the EKLF polypeptide is determined by immunofluorescence using an antibody specific for EKLF. In particular embodiments, the assay is performed using megakaryocyte/erythroid precursor cells, or mature erythrocytes. In certain embodiments, the assay is performed using cells at a differentiation stage before, during or following the CFU-E/Pro-E to Baso-E transition. In particular embodiments, the cells are sorted CFU-E/ProE, Baso-E, PolyCh-E, or OrthoCh-E cells. Related methods are described in Shyu, Y-C. et al., (2014) Developmental Cell 28: 409-422.

Methods of determining the transcription activity (e.g., transactivation or repression) of an EKLF polypeptide are also known and available in the art and include, e.g., assays to determine binding of EKLF to a target polynucleotide sequence, or transactivator or repressor activity, such as band-shift assays to measure binding of the EKLF to a target promoter or enhancer sequence, in vitro transcription assays using EKLF polypeptide and reporter constructs, and quantitative polymerase chain reaction (PCR) to determine the mRNA expression levels of genes activated or repressed by EKLF, e.g., in cells. Examples of genes that are regulated by EKLF include but are not limited to: genes that are upregulated by EKLF such as alpha globin, beta globin, Epb4.9, Tspo2, and Fn3k; and genes that are downregulated by EKLF such as Hecw1, Nrip3, and Jak3. Additional genes that are regulated by EKLF are known in the art and include, e.g., those described in Bieker et al. 1995, Mol. Cell. Biol. 15:852-860; Chen and Bieker, 2004, Mol. Cell. Biol. 24:10416-10424; Chen and Bieker, 2001, Mol. Cell. Biol. 21:3118-3125; Miller and Bieker, 1993, Mol. Cell. Biol. 13:2776-2786. In particular embodiment, the mRNA of the Col1a and/or Mpv171 genes are determined. As shown in the accompanying Examples, the mRNA levels of both these gene was reduced in EKLF mutant mice having increase longevity and reduced tumor incidence and metastasis. In certain embodiments, a cell comprising an EKLF polypeptide is contacted with a candidate agent, and the expression levels of any of these genes is determined, e.g., by RT-PCR to determine if their expression varies as compared to their expression levels, e.g., as compared to a control value or in a cell not contacted with the candidate agent.

In particular embodiments, an EKLF polypeptide is contacted with a candidate agent before or during incubation with a labeled polynucleotide comprising an EKLF binding site, e.g., a promoter or enhancer element, under conditions and for a time sufficient to allow binding of the EKLF to the polynucleotide. The amount of EKLF bound to the polynucleotide is determined using a band-shift assay.

In particular embodiments, an EKLF polypeptide, e.g., a human EKLF protein, is contacted with a candidate agent before or during an in vitro transcription assay using a reporter gene operably lined to a promoter or enhancer element bound by EKLF under conditions and for a time sufficient to allow transcription of the reporter gene. The amount of transcribed reporter mRNA or protein may be determined using quantitative PCR or by detection of the reporter protein, e.g., by fluorescence if a fluorescence report or by using an antibody that binds the reporter protein.

In certain embodiments, a cell comprising an EKLF polypeptide, e.g., a human EKLF protein, is contacted with a candidate agent for a time sufficient for the EKLF to have activated or repressed any target genes, and then the amount of target gene expressed is determined by measuring target gene mRNA or encoded protein levels, e.g., by quantitative PCR or an immunoassay using an antibody specific for the target gene.

In certain embodiments that include measuring nuclear translocation of EKLF, the candidate agent is determined to be an active agent if the amount of the EKLF polypeptide contacted with the candidate agent present in the cytoplasm is less than 90%, less than 80%, less than 70%, less than 60%, less than 50%, less than 40%, less than 30%, less than 20%, less than 10%, or 0% as compared to the amount of an EKLF polypeptide not contacted with the candidate agent in the cytoplasm. In certain embodiments, the candidate agent is determined to be an active agent if the amount of the EKLF polypeptide present in the cytoplasm is less than or equal to a pre-determined cut-off value, which may be determined based on the amounts observed in the cytoplasm in megakaryocyte/erythroid precursor cells, mature erythrocytes, cells at a differentiation stage before, during or following the CFU-E/Pro-E to Baso-E transition, or sorted CFU-E/ProE, Baso-E, PolyCh-E, or OrthoCh-E cells. In particular embodiments, the pre-determined cut-off value is 80%, 50% or 10%. In certain embodiments that include measuring nuclear translocation of EKLF, the candidate agent is determined to be an active agent if the amount of the EKLF polypeptide contacted with the candidate agent present in the nucleus is greater than 90%, greater than 80%, greater than 70%, greater than 60%, greater than 50%, greater than 40%, greater than 30%, greater than 20%, or greater than 10%, as compared to the amount of an EKLF polypeptide not contacted with the candidate agent in the nucleus. In certain embodiments, the candidate agent is determined to be an active agent if the amount of the EKLF polypeptide present in the nucleus is less than or equal to a pre-determined cut-off value, which may be determined based on the amounts observed in the nucleus in Baso-E. In particular embodiments, the pre-determined cut-off value is 80%, 50% or 10%.

In certain embodiments that include measuring transactivator activity of EKLF, the candidate agent is determined to be an active agent if the amount of the target gene expressed in the presence of an EKLF polypeptide that was contacted with the candidate agent being examined is less than 90%, less than 80%, less than 70%, less than 60%, less than 50%, less than 40%, less than 30%, less than 20%, less than 10%, or 0% as compared to the amount of the target gene expressed in the presence of an EKLF polypeptide not contacted with the candidate agent. In certain embodiments that include measuring repressor activity of EKLF, the candidate agent is determined to be an active agent if the amount of the target gene expressed in the presence of an EKLF polypeptide that was contacted with the candidate agent being examined is increased by at least 10%, at least 20%, at least 30%, at least 40%, at least 50%, at least 60%, at least 70%, at least 100%, at least 200%, at least 500%, or at least 1000% as compared to the amount of the target gene expressed in the presence of an EKLF polypeptide not contacted with the candidate agent.

In other embodiments, a method of identifying an active agent capable of extending the lifespan or health span and/or inhibiting tumorigenesis or tumor metastasis of a subject, comprises: administering a candidate agent to a transgenic animal, e.g., a knock-in animal, described herein; and comparing the lifespan of the transgenic, e.g., knock-in, animal after the administration of the candidate agent with that of a control animal that was not administered the candidate agent, wherein if the lifespan of the transgenic animal that was administered the candidate agent is longer than that of the control animal, then the candidate agent is the active agent capable of extending the lifespan or health span and/or inhibiting tumorigenesis or tumor metastasis of the subject. In particular embodiments, the lifespan of the animal treated with an active agent is extended by at least 5%, at least 10%, at least 20%, at least 30%, at least 40%, at least 50%, at least 60%, at least 70%, at least 80%, at least 90%, or at least 100% as compared to the lifespan of an animal not treated with the active agent. In particular embodiments, the transgenic animal is a non-human mammal knock-in wherein both EKLF alleles have been modified to reduce sumoylation at Lys74 or phosphorylation at Ser68. In particular embodiments, both EKLF alleles comprise an amino acid substation in place of Lys74 or Ser68. In particular embodiments, the amino acid substitution is K74R.

The candidate agent can be administered to the animal in any manner desired and/or appropriate for delivery of the agent in order to examine the increasing longevity activity or reduced tumorigenesis. For example, the candidate agent can be administered by injection (e.g., by intravenously, intramuscularly, subcutaneously injection), infusion, orally, or any other suitable means.

Administration of a candidate agent to an animal may involve administering varying amounts of the candidate agent, and may include delivery of the agent in different formulations and routes. The ability of a candidate agent to halt or slow down a normal aging process can be assessed by administering the candidate agent to the animal, e.g., transgenic animal, and evaluating its effect on the lifespan of the transgenic animal. The ability of a candidate agent to prevent aging can be assessed by administering the candidate agent to a wild-type animal or without induction of the EKLF K74R mutation that results in enhanced lifespan.

In another embodiment, the present invention provides a method of identifying candidate targets for increasing longevity, life span or health span, or reducing tumorigenesis or tumor metastasis, that includes: measuring the expression level in a wild-type animal (or wild type cell) of one or more genes regulated by an EKLF polypeptide; and measuring the expression level in an animal (or cell) that expresses a modified EKLF polypeptide described herein of the one or more genes regulated by an EKLF polypeptide, wherein genes showing a significant difference in expression level between the two animals (or cells) are identified as candidate therapeutic targets. In certain embodiments, the genes include one or more of the various genes described herein as being regulated by EKLF. In particular embodiments, the measured expression levels are amounts of mRNA transcribed from the one or more genes or amounts of the polypeptide encoded by the one or more genes. Methods of determining amounts of mRNA in a sample are known and available in the art and include, for example, quantitative polymerase chain reaction (qPCR). Methods of determining amounts of a polypeptide in a sample are known and available in the art and include, for example, ELISA, immunoprecipitation, or FACS, typically using antibodies that specifically bind to the encoded polypeptide. In particular embodiments, expression levels of the one or more genes are determined in one or more particular cell types of the animals, e.g., bone marrow cells, erythrocytes, blood cells, erythrocyte and/or megakaryocyte progenitor cells, or multipotent progenitor cells. Such cells may be isolated from the animal using procedures known in the art, including, e.g., FACS using antibodies that bind to specific cell surface markers present on these cell types. In particular embodiments, the transgenic animal is a non-human mammal knock-in wherein both EKLF alleles have been modified to reduce sumoylation at Lys74 or phosphorylation at Ser68. In particular embodiments, both EKLF alleles comprise an amino acid substation in place of Lys74 or Ser68. In particular embodiments, the amino acid substitution is K74R.

Examples of genes that are regulated by EKLF include but are not limited to: genes that are upregulated by EKLF such as alpha globin, beta globin, Epb4.9, Tspo2, Fn3k; and genes that are downregulated by EKLF such as Hecw1, Nrip3, and Jak3. In certain embodiments, genes having higher expression in wild type animals (or cells) as compared to the modified EKLF animals (or cells) of the present invention (and their encoded proteins) are targets for agents that reduce their expression or inhibit their activity, e.g., at the expression level or at the protein level. In certain embodiments, genes having lower expression in wild type animals (or cells) as compared to the modified EKLF animals (or cells) of the present invention (and their encoded proteins) are targets for agents that increase their expression or increase their activity, such as gene therapy vectors.

In particular embodiments of methods of identifying an active agent based on different amounts of expression of genes or their encoded proteins, the method further comprises identifying agents known to modulate the expression or activity of a gene or encoded protein identified as being differentially expressed in wild type animals or cells as compared to modified EKLF animals or cells. Such agents may be identified by a variety of means, including, e.g., reference to scientific publications or databases that include information on how certain chemical compounds affect the expression of specific genes, or based on the known functional activity of the differentially expressed protein.

In one embodiments, the present invention includes a method of identifying an active agent capable of increasing longevity and/or inhibiting tumorigenesis or tumor metastasis of a subject, comprising: contacting a cell capable of expressing a modified EKLF allele encoding a modified EKLF polypeptide comprising one or more amino acid modifications as compared to a wild-type EKLF polypeptide with a candidate agent; and measuring the expression level of the modified EKLF polypeptide, wherein if the expression level of the modified EKLF polypeptide is higher than the expression level in a control cell not contacted with the candidate agent, the candidate agent is an active agent capable of increase longevity and/or inhibiting tumorigenesis of the subject.

In certain embodiments, any of the methods for identifying an active agent described herein further comprise one or more additional steps, e.g., to confirm or validate that the candidate agent has the desired effect on a mammal. In one embodiment, the methods further include providing an identified active agent to a mammal and determining whether the mammal has one or more characteristics associated with increased longevity, increased life span or increased health span, as compared to a mammal not treated with the active agent. Examples of such characteristics include reduced graying of the hair, increased motor coordination, increased muscle strength, reduced osteoporosis, greater bone volume, increased bone density, greater trabecular number, or reduced trabecular spacing, e.g., as compared to untreated mammals of the same age. In addition, cellular changes associated with aging may be examined, or changes in tissue or organ structure or function may be examiner. In one embodiment, the methods further include providing an identified active agent to a mammal and determining whether the mammal has one or more characteristics associated with reduced tumorigenesis or tumor metastasis, as compared to a mammal not treated with the active agent.

In particular embodiments of any of the screening assays, the EKLF polypeptide is a wild type EKLF polypeptide or a fragment thereof capable of being phosphorylated and/or sumoylated. In certain embodiments, a fragment comprises a stretch of at least 10%, at least 20%, at least 30%, at least 40%, at least 50%, at least 70%, at least 80%, or at least 90% of the contiguous amino acids of an EKLF polypeptide. In particular embodiments, an EKLF polypeptide has at least 80%, at least 85%, at least 90%, at least 95%, or at least 98% identity to a wild-type EKLF polypeptide or fragment thereof. In particular embodiments, a wild type EKLF polypeptide is a mammalian EKLF, such as a mouse, human, rat or rabbit EKLF polypeptide, including but not limited to any of those described herein. In certain embodiments, the EKLF polypeptide is a modified EKLF polypeptide, including but not limited to an EKLF polypeptide comprising an amino acid modification, e.g., substitution, at a sumoylation site or phosphorylation site described herein. In particular embodiments, the EKLF polypeptide is endogenous to the cell, whereas in other embodiments, the EKLF polypeptide is exogenous to the cell or has been introduced into the cell. In particular embodiments, the cell comprises an exogenous nucleic acid capable of expressing the EKLF polypeptide. In particular embodiments, the cell is a transgenic cell described herein or derived from a transgenic animal described herein.

The candidate agents that can be screened for increasing longevity activity or reduced tumorigenesis activity, e.g., using the non-human transgenic animal model established herein, include, without limitation, synthetic, naturally occurring, or recombinantly produced molecules, including small molecules, peptides, antibodies, and polypeptides. Candidate agents can be obtained from a wide variety of sources including libraries of synthetic or natural compounds. For example, the candidate agents can be obtained using any of the numerous approaches in combinatorial library methods known in the art, including biological libraries, spatially addressable parallel solid phase or solution phase libraries; synthetic library methods requiring deconvolution, the 'one-bead one compound' library method, and synthetic library method using affinity chromatography selection. The biological library approach includes peptide libraries, while other approaches are applicable to peptide, non-peptide oligomers or small molecule libraries of compounds.

In certain embodiments, active agents (and candidate agents) are small organic compounds, peptides, proteins, polynucleotides, non-peptide compounds, synthetic compounds, fermentation products, or cell extracts. In certain embodiments, small organic compounds have a molecular weight of more than 50 and less than about 20,000 daltons. In particular embodiments, proteins are antibodies or fragments thereof, such as scFv, nanobodies, etc. In particular embodiments, an active agent is an antibody or fragment thereof that binds to EKLF, thus preventing its phosphorylation at Ser68 and/or sumoylation at Lys74. In certain embodiments, the antibody or fragment thereof binds to a region of EKLF that comprises or overlaps with a region of amino acid residues 68-74 of EKLF.

In certain embodiments, polynucleotides are DNA or RNA, either single-stranded or double-stranded, and including modified forms thereof, including those having modified nucleobases and/or modified internucleoside linkages, e.g., to enhance stability or increase potency. In certain embodiments, polynucleotides bind to and/or inhibit expression or translation of an EKLF gene or mRNA. In certain embodiments, polynucleotides are RNA interfering agents, siRNA, shRNA, multivalent siRNA, or miRNA. Polynucleotides that bind to an EKLF gene or mRNA may be designed based on available computer modeling programs, which identify optimal target regions within a gene or mRNA (see, e.g., Halo-Bio RNAi Therapeutics, Seattle, Wash.). In particular embodiments, a polynucleotide agent comprises a region of homology to or a region complementary to an EKLF DNA or mRNA sequence, e.g., a homologous or complementary region of at least 6 nucleotides, at least 8 nucleotides, at least 12 nucleotides, at least 16 nucleotides, at least 24 nucleotides, or at least 30 nucleotides. In particular embodiments, candidate agents are compounds known to decrease or inhibit phosphorylation or sumoylation.

In particular embodiments, an assay described herein is used to screen a library comprising a plurality of candidate agents in order to identify an active agent. In particular embodiments, the library comprises a plurality of small organic compounds, peptides, proteins, or polynucleotides. A variety of libraries of small organic compounds are known and commercially available, which may be used according to the present invention.

Methods for Enhancing Longevity, Lifespan, or Health Span, and Reducing Tumorgenisis or Tumor Metastasis The present invention further provides methods for increasing longevity, life span or health span of a subject, as well as methods for inhibiting tumorigenesis or tumor metastasis of a subject in need thereof. As shown in the accompanying Examples, it has been unexpectedly demonstrated that modification of the sumoylation site of the EKLF polypeptide in a mammal results in increased longevity, increased life span and increased health span of the mammal, as well as reduced tumorigenesis and reduced tumor metastasis in the mammal. In addition, the role of the EKLF K74R modification on cancerous cells was tested in melanoma bearing mice. Surprisingly, the expression of EKLF K74R allele prevented the cancerous melanoma cells from metastasizing. Accordingly, one further aspect of the present disclosure is to provide a method of treating a subject suffering from a cellular proliferative disorder. Without wishing to be bound to any particular theory, it is believed that modification of the sumoylation site inhibits or destroys sumoylation of the EKLF polypeptide, which alters its activity in a manner resulting in increased longevity and health, as well as reduced tumorigenesis and tumor metastasis.

Accordingly, the present invention includes methods for increasing or enhancing longevity, life span or health span of a subject, as well as methods for inhibiting tumorigenesis or tumor metastasis, which include providing a modified EKLF polypeptide of the invention to the subject, and/or providing a first agent that alters an activity of an endogenous or wild-type EKLF polypeptide to the subject. In certain embodiments, a second agent that reduces the activity or expression of endogenous, wild-type EKLF polypeptides in the subject is also be provided to the subject. In particular embodiments, a subject is a mammal, e.g., a human or non-human mammal. The first active agent, second active agent and/or modified EKLF polypeptide may be provided to the subject in an effective amount. The modified EKLF polypeptide by be provided by administering a modified EKLF polypeptide or a polynucleotide encoding the modified EKLF polypeptide to the subject. In particular embodiments, the modified EKLF polypeptide is a modified human EKLF polypeptide. In particular embodiments, it comprises a mutation that inhibits sumoylation, In certain embodiments, it comprises a modification of Lys54. These methods may also be used to achieve, or retain for a longer period of time, a specific phenotype or characteristic associated with youthfulness or increased longevity, including any of those described or demonstrated herein, such as reduced graying of the hair, increased motor coordination, increased muscle strength, reduced osteoporosis, greater bone volume, greater bone density, greater trabecular number, or reduced trabecular spacing, e.g., as compared to untreated subjects of the same age.

In particular embodiments, the subject is a mammal, e.g., a human. In certain embodiments, the subject has been diagnosed with or is considered at risk of developing a tumor or a tumor metastasis. In particular embodiments, the subject has been diagnosed with or is considered at risk of developing a disease or disorder associated with aging. In certain embodiments, the subject is at least 20 years old, at least 30 years old, at least 40 years old, at least 50 years old, at least 60 years old, at least 70 years old, or at least 80 years old.

In one embodiment, the present invention includes a method of treating or preventing a cellular proliferative disorder (e.g., tumorigenesis or tumor metastasis) in a subject in need thereof, comprising administering to the subject an effective amount of a polypeptide, or a nucleic acid encoding the polypeptide, wherein the polypeptide is a modified EKLF polypeptide comprising one or more amino acid modifications that confer decreased sumoylation and/or decreased nuclear translocation of the modified EKLF polypeptide as compared to a wild-type EKLF polypeptide. In certain embodiments, the modified EKLF polypeptide is a modified human EKLF polypeptide. In certain embodiments, the modified EKLF polypeptide has decreased sumoylation as compared to the wild-type EKLF polypeptide. In certain embodiments, the modified EKLF polypeptide has reduced translocation from the cytoplasm to the nucleus as compared to the wild-type EKLF polypeptide. In certain embodiments, the modified EKLF polypeptide has a modified transactivator activity or a modified repressor activity as compared to the wild-type EKLF polypeptide. In various embodiments, the one or more amino acid modifications comprises a modification at an amino acid position that is sumoylated or phosphorylated in the wild-type EKLF polypeptide, such as a modification of an amino acid at position 74 of the full length mouse wild-type EKLF polypeptide, e.g., substitution of Lys with Arg (K74R), or a modification of an amino acid at position 54 of the full length human wild-type EKLF polypeptide, e.g., substitution of Lys with Arg (K54R), or a modification of an amino acid at position 68 of the full length wild-type EKLF polypeptide. One method includes administering to the subject an effective amount of a polypeptide or a nucleic acid encoding the polypeptide, wherein the polypeptide is a modified human EKLF, in which the lysine residue at position 54 is mutated, optionally to arginine. In particular embodiments, the modified human EKLF is not sumoylated at position 54.

Polypeptides may be administered to a subject in a variety of manner, including as "naked" polypeptides or complexed with a delivery-enhancing agent. In particular embodiments, a polypeptide is associated with an agent that enhances cellular uptake. Nucleic acids may be administered to a subject in a variety of manners, including as "naked" DNA or RNA, or complexed with lipids or encapsulated in a lipid particle. In particular embodiments wherein a nucleic acid, i.e., a polynucleotide, is administered to the subject, the nucleic acid is present in an expression vector. In certain embodiments, the nucleic acid is present in a viral vector. The viral vector may be a replication defective or replication competent viral vector. In various embodiments, the viral vector is derived from a herpes virus, a retrovirus, a lentivirus, a vaccinia virus, an attenuated vaccinia virus, a canary pox virus, an adenovirus, or an adeno-associated virus. The nucleic acid may be present in an expression vector, in which the nucleic acid sequence encoding the modified EKLF polypeptide is operatively linked to a promoter or enhancer-promoter combination. Suitable expression vectors include plasmids and viral vectors such as herpes viruses, retroviruses, vaccinia viruses, attenuated vaccinia viruses, canary pox viruses, adenoviruses and adeno-associated viruses. In particular embodiments, the nucleic acid is operably linked to a promoter sequence and, optionally enhancer elements. In particular embodiments, the promoter and/or enhancer elements confer tissue-specific expression of the nucleic acid and its encoded polypeptide. In particular embodiments, the promoter and/or enhancer elements are EKLF gene promoter and/or enhancer elements, and confer a similar or the same expression pattern to the nucleic acid as endogenous EKLF.

The above-mentioned nucleic acids or polynucleotide can be delivered by the use of polymeric, biodegradable microparticle or microcapsule delivery devices known in the art. Another way to achieve uptake of the nucleic acid in a host is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of "naked DNA" (i.e., without a delivery vehicle) to an intramuscular, intradermal, or subcutaneous site is another means to achieve in vivo expression.

The polypeptide can be synthesized using methods known in the art or be prepared using recombinant technology. For example, one can clone a nucleic acid encoding the polypeptide (e.g., the modified EKLF having K74R mutation) in an expression vector, in which the nucleic acid is operably linked to a regulatory sequence suitable for expressing the polypeptide in a host cell. One can then introduce the vector into a suitable host cell to express the polypeptide. The expressed recombinant polypeptide can be purified from the host cell by methods such as ammonium sulfate precipitation and fractionation column chromatography. A polypeptide thus prepared can be tested for its activity according to the methods described herein.

In certain embodiments wherein the polypeptide or the nucleic acid is administered to the subject, the methods further comprise administering to the subject a second active agent that inhibits expression of the endogenous EKLF polypeptide. In particular embodiments, the second active agent is a nucleic acid molecule, optionally an antisense RNA, siRNA, shRNA or miRNA that binds an mRNA or complement thereof that encodes the endogenous EKLF polypeptide.

In one embodiment, the present invention includes a method of treating or preventing a cellular proliferative disorder (e.g., tumorigenesis or tumor metastasis) in a subject in need thereof, comprising administering to the subject an effective amount of an active agent that inhibits sumoylation of the endogenous EKLF polypeptide and/or reduces translocation of the endogenous EKLF polypeptide from the cytoplasm to the nucleus. In one embodiment, the active agent inhibits sumoylation. In one embodiment, the active agent reduces translocation.

In one embodiment, the present invention includes a method of treating or preventing a cellular proliferative disorder (e.g., tumorigenesis or tumor metastasis) in a subject in need thereof, comprising administering to the subject an effective amount of an active agent that alters one or more activities of the endogenous EKLF polypeptide. In one embodiment, the active agent inhibits sumoylation. In one embodiment, the active agent reduces translocation. In certain embodiments, the active agent modifies a transactivator activity or modifies a repressor activity of the endogenous EKLF polypeptide.

In particular embodiments, active agents used in methods of the present invention bind to the endogenous EKLF polypeptide. In particular embodiments, an active agent is a small organic molecule or a polypeptide, optionally an antibody or functional fragment thereof.

Methods of the present invention may be used to treat or prevent a variety of cellular proliferative disorders, including but not limited to tumors and tumor metastases, including but not limited to any of those described herein. In particular embodiments, the tumor or tumor metastasis is a liver cancer, a colon cancer, a breast cancer, a prostate cancer, a hepatocellular carcinoma, a melanoma, a lung cancer, a glioblastoma, a brain tumor, a hematopoetic malignancy, a retinoblastoma, a renal cell carcinoma, a head and neck cancer, a cervical cancer, a pancreatic cancer, an esophageal cancer, or a squamous cell carcinoma.

In particular embodiments, methods of treating or preventing a proliferative disorder further comprise administering to the subject an effective amount of an anti-proliferation agent for treating the cellular proliferative disorder. In particular embodiments, the anti-proliferation agent is an alkylating agent, a topoisomerase inhibitor, an anti-metabolite, or a cytotoxicity antibiotic. In some embodiments, the alkylating agent is cisplatin, carboplatin, oxaliplatin, mechlorethamine, cyclophosphamide, melphalan, chlorambucil, ifosfamide, busulfan, N-nitroso-N-methylurea (MNU), carmustine, lomustine, semustine, fotemustine, streptozotocin, dacarbazine, mitozolomide, temozolomide, thiotepa, mytomycin, or diaziquone. In some embodiments, the topoisomerase inhibitor is camptothecin, irinotecan, topotecan, etoposide, doxorubicin, teniposide, novobiocin, merbarone, or aclarubicin. In some embodiments, the antimetabolite is fluoropymidine, deoxynucleoside analogue, thiopurine, methotrexate, or pemetrexed. In some embodiments, the cytotoxicity antibiotic is actinomycin, bleomycin, plicamycin, mitomycin, doxorubicin, daunorubicin, epirubicin, idarubicin, pirarubicin, alcarubicin, or mitoxantrone.

In other embodiments, the present invention includes a method of extending the lifespan or health span of a subject, comprising administering to the subject an effective amount of a polypeptide, or a nucleic acid encoding the polypeptide, wherein the polypeptide is a modified EKLF polypeptide comprising one or more amino acid modifications that confer decreased sumoylation and/or decreased nuclear translocation of the modified EKLF polypeptide as compared to a wild-type EKLF polypeptide. In certain embodiments, the modified EKLF polypeptide has decreased sumoylation as compared to the wild-type EKLF polypeptide. In certain embodiments, the modified EKLF polypeptide has reduced translocation from the cytoplasm to the nucleus as compared to the wild-type EKLF polypeptide. In certain embodiments, the modified EKLF polypeptide has a modified transactivator activity or a modified repressor activity as compared to the wild-type EKLF polypeptide. In particular embodiments, the nucleic acid is present in an expression vector. In certain embodiments, the nucleic acid is present in a viral vector. In various embodiments, the viral vector is derived from a herpes virus, a retrovirus, a vaccinia virus, an attenuated vaccinia virus, a canary pox virus, an adenovirus, or an adeno-associated virus. In various embodiments, the one or more amino acid modifications comprises a modification at an amino acid position that is sumoylated or phosphorylated in the wild-type EKLF polypeptide, such as a modification of an amino acid at position 74 of the full length wild-type EKLF polypeptide, e.g., substitution of Lys with Arg (K74R), or a modification of an amino acid at position 68 of the full length wild-type EKLF polypeptide.

In certain embodiments wherein the polypeptide or the nucleic acid is administered to the subject, the methods further comprise administering to the subject a second active agent that inhibits expression of the endogenous EKLF polypeptide. In particular embodiments, the second active agent is a nucleic acid molecule, optionally an antisense RNA, siRNA, shRNA or miRNA that binds an mRNA or complement thereof that encodes the endogenous EKLF polypeptide.

In one embodiment, the present invention includes a method of extending the lifespan or health span of a subject, comprising administering to the subject an effective amount of an active agent that inhibits sumoylation of the endogenous EKLF polypeptide and/or reduces translocation of the endogenous EKLF polypeptide from the cytoplasm to the nucleus. In one embodiment, the active agent inhibits sumoylation. In one embodiment, the active agent reduces translocation.

In one embodiment, the present invention includes a method of extending the lifespan or health span of a subject, comprising administering to the subject an effective amount of an active agent that alters one or more activities of the endogenous EKLF polypeptide. In one embodiment, the active agent inhibits sumoylation. In one embodiment, the active agent reduces translocation. In certain embodiments, the active agent modifies a transactivator activity or modifies a repressor activity of the endogenous EKLF polypeptide.

The present invention further includes pharmaceutical compositions comprising a polynucleotide encoding a modified EKLF, a modified EKLF polypeptide, a candidate agent, or an active agent, and one or more pharmaceutically acceptable excipients, diluents or carriers. Methods of the present invention may be performed using pharmaceutical composition comprising any of these. Embodiments of the present invention include compositions comprising modified EKLF polypeptide, polynucleotides encoding modified EKLF polypeptides, or active agents formulated in pharmaceutically-acceptable or physiologically-acceptable solutions for administration to a cell, subject, or an animal, either alone, or in combination with one or more other modalities of therapy. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect the modulatory or other effects desired to be achieved.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

In certain circumstances it will be desirable to deliver the pharmaceutical compositions disclosed herein parenterally, subcutaneously, intravenously, intramuscularly, intra-arterially, intrathecally, intraparenchymally, intracisternally, intraventricularlly, intraurethrally, intrasternally, intracranially, intrasynovially, or even intraperitoneally as described, for example, in U.S. Pat. Nos. 5,543,158; 5,641,515 and 5,399,363 (each specifically incorporated herein by reference in its entirety). Suitable devices for parenteral administration include needle (including microneedle) injectors, needle-free injectors, and infusion techniques.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington's Pharmaceutical Sciences, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the delivery may occur by use of liposomes, nanocapsules, microparticles, microspheres, lipid particles, vesicles, and the like. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

In certain embodiments, the agents provided herein may be attached to a pharmaceutically acceptable solid substrate, including biocompatible and biodegradable substrates such as polymers and matrices. Examples of such solid substrates include, without limitation, polyesters, hydrogels (for example, poly(2-hydroxyethyl-methacrylate), or poly(vinyl-alcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as poly(lactic-co-glycolic acid) (PLGA) and the LUPRON DEPOT™ (injectable microspheres composed of lactic acid-glycolic acid copolymer and leuprolide acetate), poly-D-(−)-3-hydroxybutyric acid, collagen, metal, hydroxyapatite, bioglass, aluminate, bioceramic materials, and purified proteins.

Methods of formulation are well known in the art and are disclosed, for example, in Remington: The Science and Practice of Pharmacy, Mack Publishing Company, Easton, Pa., 19th Edition (1995). The compositions and agents provided herein may be administered according to the methods of the present invention in any therapeutically effective dosing regime. The dosage amount and frequency are selected to create an effective level of the agent without harmful effects. The effective amount of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

Embodiments of the present invention, in other aspects, provide kits comprising one or more containers filled with one or more pharmaceutical compositions of the polypeptides, polynucleotides, active agents, etc., of the invention, as described herein. The kits can include written instructions on how to use such compositions (e.g., to enhance longevity, life span or health span, or to inhibit or reduce tumorigenesis or tumor metastasis).

The kits herein may also include one or more additional therapeutic agents or other components suitable or desired for the indication being treated, or for the desired diagnostic application. An additional therapeutic agent may be contained in a second container, if desired. Examples of additional therapeutic agents include, but are not limited to anti-neoplastic agents.

The kits herein can also include one or more syringes or other components necessary or desired to facilitate an intended mode of delivery (e.g., stents, implantable depots, etc.).

EXAMPLES

Materials and Methods
Experimental Animals
Adult C57BL mice (18 to 25 g) were obtained from the National Laboratory Animal Center in Taiwan. All mice were maintained in the animal facility in accordance with the procedures approved by the Experimental Animal Committee, Academia Sinica (Taiwan, R.O.C.).

Generation of the EKLF (K74R) Knock-in Mice

Knock-in mice were generated by introducing the sumoylation site mutation (K74R) of EKLF into the 2nd exon of the mouse EKLF (klf1) gene through homologous recombination in ES cells by a standard gene-targeting approach using the Cre-loxP recombination system, the targeting BAC Clone RP24-319P23 (Invitrogen) and the counter-selection BAC modification Kit (Gene brides). Using mouse genomic DNA from C57B/6J ES cells as template, a fragment containing portions of EKLF exon 2 was PCR amplified and used for constructing a target vector. Prior to cloning into the template targeting vector, codon 74 encoded by exon 2 was mutated to code for arginine (K74R) using standard mutagenesis techniques. A neomycin cassette was also constructed into the target vector, in which a PGK-gb2-neo template encodes the neomycin/kanamycin resistance gene which combines a prokaryotic promoter (gb2) for expression of kanamycin resistance in *E. coli* with a eukaryotic promoter (PGK) for expression of neomycin resistance in mammalian cells. In addition, the modified wild-type DNA was flanked by 'loxP' sites to facilitate its removal (FIG. 1A). The loxP-PGK-loxP cassette was inserted at intron 1 of the EKLF gene. The target construct was then electroporated into C57B/6J ES cells and selected for neomycin resistance. Appropriately targeted ES clones were identified by 5' and 3' Southern blotting. Following removal of the neo cassette and confirmation of the architecture of the modified genomic region encoding EKLF K74R, the ES clones were injected into blastocytes to generate chimera mice. To obtain heterozygous mice containing the knock-in allele, the germline transmitting F1 lines were crossed with EIIa-Cre mice expressing the Cre recombinase in the whole body. The eklf heterozygotes carrying one allele containing the point mutation were intercrossed to achieve the homozygous eklf (K74R) knock-in mice.

The EKLF K74R knock-in targeting vector sequence is shown in Table E1 below. The sequence is listed in the order from 5' to 3', and the nucleotide positions are numbered in the 5' to 3' direction with the first 5' nucleotide numbered as 1. Regions of the targeting vector, e.g. exons and introns of the EKLF gene, loxP sites, PolyA sites, Neo, and the PGK promoter are indicated by their nucleotide region, i.e. the range of nucleotide positions that the region spans.

TABLE E1

| Targeting Vector Polynucleotide Sequence |  |
| --- | --- |
| Vector SEQ ID NO: 8 | GTGGGCAGACAGGAGCCCTCCAAGAAACTTTCCTAGCCT CATAGCCCATGAGGCAGAAGAGAGAGAGGAGGCCTGAGG TCCAGGGTGGACACCAGCCAGCCATGGCCTCAGCTGAGA CTGTCTTACCCTCCATCAGTACACTCACCACCCTGGGAC AGTTCCTGGACACCCAGGAGGACTTCCTCAAGGTGGGGC CAGTGTGAGTGTGTGGGAGGGGGCAGGTGGTCTTGCATA GGGCATAGTGCTTAGGGGTGGGGCGTCTATCTTACTTTA ATATCCTCTGCTCTGTTTTTTGGGGGTGGAGGAGTGGGA GAGCCTCTGAGCCTTGTTTGGGGGAGATGTTCTAGGGGT CTGAGATCAAGGTGAGGTGACACTATAGAATACTCAAGC TATCGAGATAACTTCGTATAATGTATGCTATACGAAGTT ATCGCGCCGCACACAAAAACCAACACACAGATCATGAAA ATAAAGCTCTTTTATTGGTACCGAATTCGCCAGGGAGCT CTCAGACGTCGCTTGGTCGGTCTTTATTCGAACCCCAGA GTCCCGCTCAGAAGAACTCGTCAAGAAGGCGATAGAAGG CGATGCGCTGCGAATCGGGGGCGGCGATACCGTAAAGCA CGAGGAAGCGGTCAGCCCATTCGCCGCCAAGCTCTTCAG CAATATCACGGGTAGCCAACGCTATGTCCTGATAGCGGT CCGCCACACCCAGCCGGCCACAGTCGATGAATCCAGAAA AGCGGCCATTTTCCACCATGATATTCGGCAAGCAGGCAT CGCCATGGGTCACGACGAGATCCTCGCCGTCGGGCATGC GCGCCTTGAGCCTGGCGAACAGTTCGGCTGGCGCGAGCC CCTGATGCTCTTCGTCCAGATCATCCTGATCGACAAGAC CGGCTTCCATCCGAGTACGTGCTCGCTCGATGCGATGTT |

TABLE E1-continued

Targeting Vector Polynucleotide Sequence

TCGCTTGGTGGTCGAATGGGCAGGTAGCCGGATCAAGCG
TATGCAGCCGCCGCATTGCATCAGCCATGATGGATACTT
TCTCGGCAGGAGCAAGGTGAGATGACAGGAGATCCTGCC
CCGGCACTTCGCCCAATAGCAGCCAGTCCCTTCCCGCTT
CAGTGACAACGTCGAGCACAGCTGCGCAAGGAACGCCCG
TCGTGGCCAGCCACGATAGCCGCGCTGCCTCGTCCTGCA
GTTCATTCAGGGCACCGGACAGGTCGGTCTTGACAAAAA
GAACCGGGCGCCCCTGCGCTGACAGCCGGAACACGGCGG
CATCAGAGCAGCCGATCGTCTGTTGTGCCCAGTCATAGC
CGAATAGCCTCTCCACCCAAGCGGCCGGAGAACCTGCGT
GCAATCCATCTTGTTCAATGGCCGATCCCATGGTTTAGT
TCCTCACCTTGTCGTATTATACTATGCCGATATACTATG
CCGATGATTAATTGTCAACACGTGCTGCTGCAGGTCGAA
AGGCCCGGAGATGAGGAAGAGGAGAACAGCGCGGCAGAC
GTGCGCTTTTGAAGCGTGCAGAATGCCGGGCCTCCGGAG
GACCTTCGGGCGCCCGCCCCGCCCCTGAGCCCGCCCCTG
AGCCCGCCCCCGGACCCACCCCTTCCCAGCCTCTGAGCC
CAGAAAGCGAAGGAGCAAAGCTGCTATTGGCCGCTGCCC
CAAAGGCCTACCCGCTTCCATTGCTCAGCGGTGCTGTCC
ATCTGCACGAGACTAGTGAGACGTGCTACTTCCATTTGT
CACGTCCTGCACGACGCGAGCTGCGGGCGGGGGGGAAC
TTCCTGACTAGGGGAGGAGTAGAAGGTGGCGCGACGGGG
CCACCAAAGAACGGAGCCGGTTGGCGCCTACCGGTGGAT
GTGGAATGTGTGCGAGGCCAGAGGCCACTTGTGTAGCGC
CAAGTGCCCAGCGGGGCTGCTAAAGCGCATGCTCCAGAC
TGCCTTGGGAAAAGCGCCTCCCCTACCCGGTAGAATATA
ACTTCGTATAATGTATGCTATACGAAGTTATGCGGCCCT
AGTGATTTAGGCTCATAGAGACAAAGGTCCAGATAAAGG
TGTCCTGGGATTTCCAGGCTTTGAGCTGTAATTTTCTGG
GCTATGTGAAGACAGGGAAAGGCTAGGGAAAACGGAGTC
GAAGCTGTCCCCTTTGACTCAGAACTCTGCAACCCCTTC
TCCCATCCTGAATACTATTCTTGGTAAGTGTCTTAGCTG
TCTCTAGCAAGACCTAATGGAGTTGTCTGGAGCTGAGAA
AGGGGTTAGGGGAACCGTGTGGGTAAATGACAGGCACCA
ACGGTGTTTCCAGCCAGGGTTGTTTGAGGGCCAGGTACC
CAGTGCCTACCATTCAAGCAGTACGCTCCCTCCCGCAGT
GGTGGCGGTCTGAGGAGACGCAGGATTTGGGGCCGGGGC
CCCCGAATCCCACGGGGCCGTCCCATCACGTGAGTCTGA
GATCGGAGGACCCTTCCGGAGAGGACGATGAGAGGGACG
TGACCTGTGCGTGGGACCCGGATCTTTTCCTTACAAACT
TTCCAGGTTCCGAGTCTCCCGGCACTTCCCGGACCTGTG
CCCTGGCGCCCAGCGTGGGGCCAGTGGCACAGTTCGAGC
CGCCTGAGTCTCTGGGCGCCTATGCGGGTGGCCCAGGGT
TGGTGACTGGGCCTTTGGGCTCCGAGGAGCACACAAGCT
GGGCGCACCCGACTCCGAGACCCCCAGCCCCTGAACCCT
TCGTGGCCCCTGCCCTGGCCCCGGGACTCGCTCCCAAGG
CTCAGCCCTCGTACTCCGACTCGCGAGCGGGCTCCGTAG
GGGGCTTCTTCCCGCGGGCGGGGCTTGCGGTGCCCGCAG
CTCCAGGCGCCCCCTATGGGCTGCTGTCGGGATACCCCG
CGCTGTACCCCGCGCCACAGTACCAAGGCCACTTCCAGC
TCTTTCGCGGGCTCGCGGCGCCTTCTGCTGGTCCCACGG
CGCCCCTTCCTTCTTGAATTGTCTGGGACCTGGGACTG
TGGCCACAGAACTCGGGGCCACTGCGATCGCCGGAGACG
CAGGCTTGTCCCGGGAACTGCGCCGCCCAAACGCAGCC
GGCGAACTTTGGCACCTAAGAGGCAGGCGGCACATACGT
GCGGGCACGAAGGCTGCGGGAAGAGCTACACCAAGAGCT
CGCACCTCAAGGCGCACCTGCGCACGCACACGGGTAAGG
GCGGGGCCAGACGGGCGGGGCGGGGCGGGAGCCGCTAG
TGAACGAAGGGAGGGGCCGGAGGGTAGTCAGAGGCGTGG
CTAAAGGCGGCCCAGTTCTAGGGGTCGTGAAGACCGCA
CCTGAGACACTGGGTCAAGTCTAGAAGGGGCGATTCCAG
ACCCAAATGGGCTAATACAAACACTCGGGAGGCAGAGGC
AGGTGGATAGCAGTGACTTCGAGGCCATTTGGGCTATTA
TAGCGAGTTTCAGCAGCCTGAGCTACTTAGTGAGATCCT
GGTTCATAAATAAATAGGTGTAACAGAGGACCTGGGGAA
CACTTTGGGGACTTCGGTGTTAGAAGTGGATGTGTAAGG
CCTGGGTTAGAGATGGGAGAAGAAACTAGAGGGGTGAAC
CCGAAAGGTACAAGCTTGGAATGCCAGAGCTCAGGATAT
AGCCAGTATTTACATGCATGCTCGAGCTGGAACCATCTG
GGATCAGGAGGTTGAGACACTCAAGTAAAATCAGTTTCA
GGGCAACTGACAGAGGTCCCAGAGTTAAGAAAAGAAGA
GAAGGGGCTGGAGAGATGGCTCAGTGGTTAAGAGCACT
GACTGCTCTTCCAGAGGTCCTGAGTTTAAATCCCAGCAC
CACATGGTGGCTCACAACCATCTGTAATGGGATCCGATG
CCCTCTTCTGGTGTGACTGAAGCAGCTACAGTGTACTT
ACATATAATAAATAAATAAATTAAAAAAAAAAAGAAAGA
AAGAAAAAAGAAAAGAAGAGAAGGAAATGCTGAGAGACA
GGGCCTAGAAAGAGAAACGGGGTCATCCCAGGACTGGAA

TABLE E1-continued

Targeting Vector Polynucleotide Sequence

GACAGCTGAGGGTCTCCCAAGCATGGCAGGGCACGCAAC
AGGCTGTAACAGGAAGAGAGGGAATCACCAGAGACAGGG
CCTTGAACACTGGGGTGGATTTCTGGGCTTGAACCAAGT
TGAGGAACAAGACTGGATATCATCGGGAGGCTCTGCCAG
AGCAAGAAATAGCTGCAACGCGGAGAACAAAGAACGAAG
GTGCAGCCACATAAAAAGGCAGGGAACTAGCACACCGGA
AGTGGGATAGGAGACCGGAAGTGAGAAAACTGCAGGATT
GCAGCTGTAGATACAGAAAAGGATTGAGTCACAGAAGGC
AGGATTATGTGACCTTTTAACTGTGTGGGCTAGGTATGT
CCTAAGACTTGGCTCTACTTCATCAAGGGTGCAAACTGG
AGCTGGGTTGCTTGGAGGGTGGTACTTACAGCTCCCTGT
CCTTCAGGAGAGAAGCCTTATGCCTGCTCCTGGGACGGC
TGTGACTGGAGGTTCGCTCGCTCAGACGAACTGACGCGC
CACTACCGGAAGCACACTGGACATCGTCCCTTCTGCTGT
GGCCTCTGCCCACGTGCTTTTTCACGCTCTGACCACTTA
GCTCTGCACATGAAGCGTCACCTCTGAGTGATCCTGCAC
AAGGACTGGGGATGAAATAAGAGTGGATCAAGGACCGT
ATCCCAAAAGATGGGCCATTATATAGTCCTACCCAGATC
AAAAACTGACCAGAAGACCATACAAAGGAGCCTTCAGGA
CAAACCTCACATGTCCTCAGGGAGCCCCACACATGGCCC
CACAGACCCAGCAATATAGACCACCAGATAAATCAACTC
AAATGGACCCCTAGACCAGAGGAGTGACCCTGTGTCCTG
GACGCAGATGGACTGGGGTGAGATTTCCTAAGATCTAGA
AGGGAGCTTCACACTGTGCCCATCTGCTAGGATTGTTGT
CGTTACTATAAAAATTTCCCATATAAAACCAG

| Nucleotide Region | Description of Feature |
|---|---|
| 1-4,946 | EKLF K74R Knock in Targeting Vector |
| 1-188 | Exon 1 of EKLF gene |
| 189-368 | Intron 1 of EKLF gene |
| 397-431 | LoxP site |
| 432-508 | PolyA region |
| 554-1,357 | Neo |
| 1,358-1,944 | PGK |
| 1,948-1,981 | LoxP site |
| 1,997-2,339 | Intron 1 of EKLF gene |
| 2,340-3,153 | Exon 2 of EKLF gene |
| 3,154-4,414 | Intron 2 of EKLF gene |
| 4,415-4,946 | Exon 3 |

TaqMan Gene Expression Assay

RNA was prepared using TRIzol reagent (Invitrogen) and reverse transcribed using oligo-5 dT primer and SuperScript III Reverse Transcriptase (RT) (Invitrogen) according to standard procedures. Quantitative PCR (qPCR) using the validated TaqMan assays was carried out on an Applied Biosystems 7500 Real-Time PCR System (Applied Biosystems) instrument under default cycling conditions (50° C. for 2 min, 95° C. for 10 min, 95° C. for 15 s, and 60° C. for 1 min for 40 cycles). The relative EKLF (Mm04208330_g1 and Mm00516096_m1; Applied Biosystems) expression levels were determined from a standard curve of serial dilutions of the cDNA samples and then normalized to the β-actin (Actb:Mm00607939_s1; Applied Biosystems) or Gapdh (Mm99999915_g1; Applied Biosystems) expression levels.

Lifespan Measurement

Lifespan was measure using standard procedures. The life spans of the EKLF (K74R) knock-in mice were followed-up in specific-pathogen-free (SPF) animal facility.

Assay of Resistance to Tumorigenesis

To study the anti-carcinogenesis effect of EKLF (K74R) knock-in mice, a lung colonization assay as described previously (Cha et al., 2003; Stackpole, 1981) was employed for the study. The murine metastatic melanoma cells, B16-F10 (106 cells/0.2 mL), were injected intravenously into the tail vein (i.v. injection) of EKLF (K74R) Kin mice and wild type mice (3 mice per group), respectively, to examine the potentials of tumor formation from these cells and metastasis. B16F10 cells were chosen for test because they are derived from C57BL/6 mice and immunologically compatible with the C57BL/6 mice (wild type and EKLF (K74R) knock-in mice). Two weeks later, the mice were killed by asphyxiation with $CO_2$ and their lungs were removed for further examination. Metastatic nodules on the surface of the lungs were measured by image analysis software (Image Inc.; Cha et al., 2003). The measurements of tumor number of each mouse were performed 14 days after injection.

Microarray Experiment

E14.5 mouse fetal livers or 3 months mouse bone marrow from WT and Eklf K74R knockin mices were homogenized by repeated pipetting in phosphate-buffered saline (PBS) (10 mM phosphate, 0.15 M NaCl [pH 7.4]). Total RNAs were then isolated with Trizol reagent (Invitrogen) and subjected to genome-scale gene expression profiling using the Mouse Genome Array 430A 2.0 (Affymetrix, Inc.). Standard MAS5.0 method was applied to normalize the gene expression data. Gene expression values were log-transformed for later comparative analysis. Statistical analysis was carried out using R 3.0.2 language (R Development Core Team, 2013, www.R-project.org)

Quantitative PCR (qPCR) of EKLF Target Genes

The total RNAs were extracted by means of the commercial Trizol reagent (Invitrogen) and reverse-transcribed using SuperScriptIII according to the manufacturer's protocol (Invitrogen). Mouse Cola1, Mpv17l and actin mRNA levels were determined by real-time PCR or semi-quantitative RT-PCR using appropriate primers from Mission Biotech (Taiwian, ROC). The qPCR assays were performed using an Applied Biosystems 7500 Real-Time PCR System (Applied Biosystems, Foster City, Calif., USA) with the following profile: 1 cycle at 50° C. for 2 min, 1 cycle at 95° C. for 10 min, and 35 cycles each at 95° C. for 15 s and 60° C. for 1 min. The threshold cycle (Ct) was calculated by the instrument's software (7500 System SDS software vers. 1.3.1). Actin served as an internal control, and the relative amount of Cola1 or Mpv17l mRNA was normalized to Actin. Data are presented as histograms where each bar represents the mean±SEM of data derived from 3 times. semi-quantitative RT-PCR consisted of polymerase chain reactions (PCR) incubated at 94° C. for 5 min, followed by 22 cycles at 94° C. for 30 s, 55° C. for 40 s, and 72° C. for 30 s (actin); 28 cycles at 94° C. for 30 s, 52° C. for 30 s, and 72° C. for 27 s (Cola1) and 24 cycles at 94° C. for 30 s, 52° C. for 40 s, and 72° C. for 20 s (Mpv17l), respectively. Data are presented as histograms where each bar represents the mean±SEM of data derived from 2 times.

Food/Water Intake Measurements

Spontaneous home cage activity was monitored using fully automated computer vision analysis of continuous video recordings.

Metabolism Measurements $O_2$ consumption, $CO_2$ production, food, and water intake were measured using the comprehensive lab animal monitoring system (CLAMS, Oxymax Open Circuit calorimeter, Columbus Instruments).

Insulin and Glucose Measurements

Blood samples were collected from mice. After spinning, the plasma was used to quantify insulin and glucose by ELISA (Mediagnost, Germany) following the manufacturer recommendations. The plasma was also used to quantify glucose.

Grip Strength Test

The Grip Strength test was performed with the Muromachi, MK-380CM/R apparatus. Experiments were recorded.

Rotarod Test

The rotarod test was performed with the Ugo Basile Rota-Rod 47600 apparatus. For the testing sessions, the rotarod was accelerated continuously from 2 to 80 revolutions per min.

Bone Imaging

Bone density was assessed using a Scanco Medical Micro-CT 40 instrument on whole animals immediately after euthanasia.

Tumor Imaging

MicroPET images (MicroPET R4,) of mice were taken by scanning the mice at 0.5 h after administration of the mice with 100 Ci of 18F-FDG.

Example 1

Generation of EKLF K74R Mice

Figure 1B:
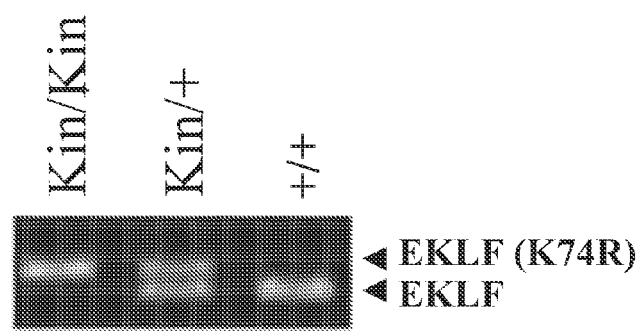
Figure 1C:
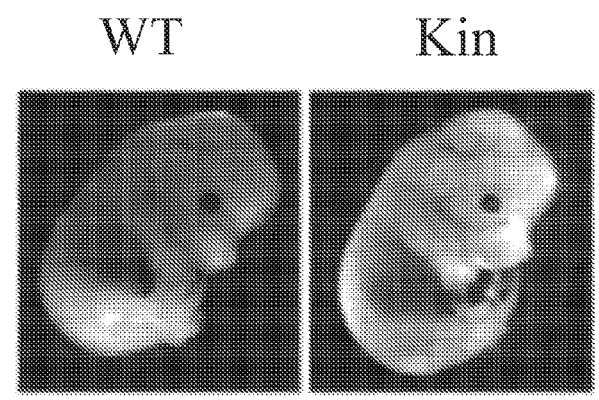
Figure 1D:
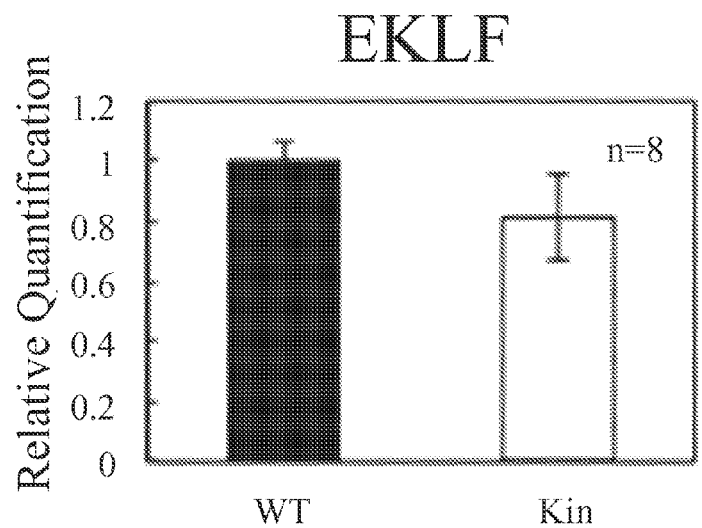

Transgenic mice carrying the EKLF K74R mutant allele were generated according to procedures described in the "Materials and Methods" section. Schematic drawings of the target vector constructs for generating EKLF K74R mice are illustrated in FIG. 1A. Genomic DNA from mouse tails were analyzed by PCR and confirmed that both the heterologous and homozygous mice contained the EKLF K74R mutant allele (FIG. 1B). The EKLF K74R Knock-in mice bred normally and produced offspring in the expected Mendelian ratios, indicating that this modified EKLF gene functioned analogous to the wild type EKLF allele, and does not cause embryonic lethality. Quantitative mRNA analysis of embryos indicated that EKLF K74R mice and wild-type littermates possessed similar levels of total EKLF mRNA (FIG. 1D).

The EKLF protein is a transcription factor with promoter and repressor activities. The transcriptome is changed by the K74R mutation. As analyzed by microarray hybridization, in either bone marrow or in E14.5 fetal liver, at least 40 genes are down-regulated and upregulated, respectively. As exemplified in FIG. 2, some of these expression changes have been validated by PCR. The mRNA of Col1a1 was significantly reduced in the bone marrow of adult EKLF K74R knock-in mice compared to wild-type type mice (FIG. 2A). The mRNA Mpv17l was significantly reduced in the E14.5 fetal liver of the EKLF K74R knock-in mice compared to wild-type mice (FIG. 2B).

Example 2

EKLF K74R Mutation Leads to Enhanced Lifespan

Figure 3A:
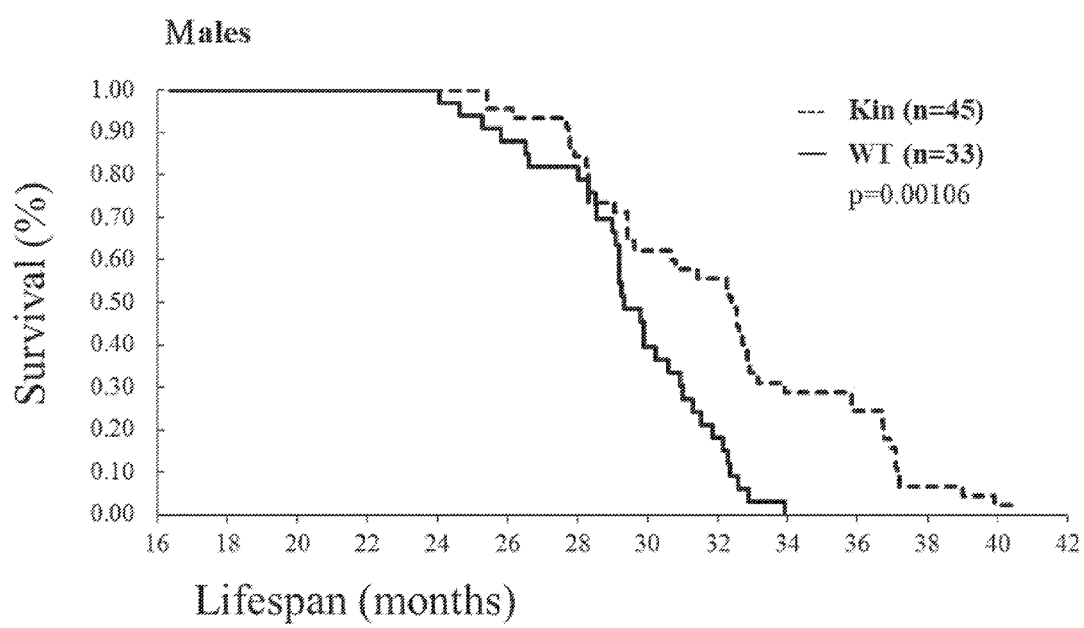
FIGS. 3A and 3B show a comparison of lifespan between EKLF K74R (Kin) and wild-type littermates (WT).

The EKLF K74R transgenic mice had an extended lifespan compared to wild-type littermates. Specifically, the median life span of the EKLF K74R mice (n=45) was 3 months longer, as compared with that of the wild-type mice (n=33) (FIG. 3A). Results of the lifespan study are summarized in Table E2.

TABLE E2

Lifespan of EKLF K74R Mice
Extended Median and Maximum Lifespan of EKLF K74R

| Genotype (males) | Mean | Maximum | Minimum | Oldest 10% | Youngest 10% | n |
|---|---|---|---|---|---|---|
| K74R | 32.2 ± 4.0 | 40.4 | 25.4 | 38.7 ± 1.5 | 26.5 ± 1.2 | 45 |
| WT | 29.5 ± 2.4 | 33.9 | 24.1 | 32.9 ± 0.7 | 24.9 ± 0.7 | 33 |

Figure 3B:
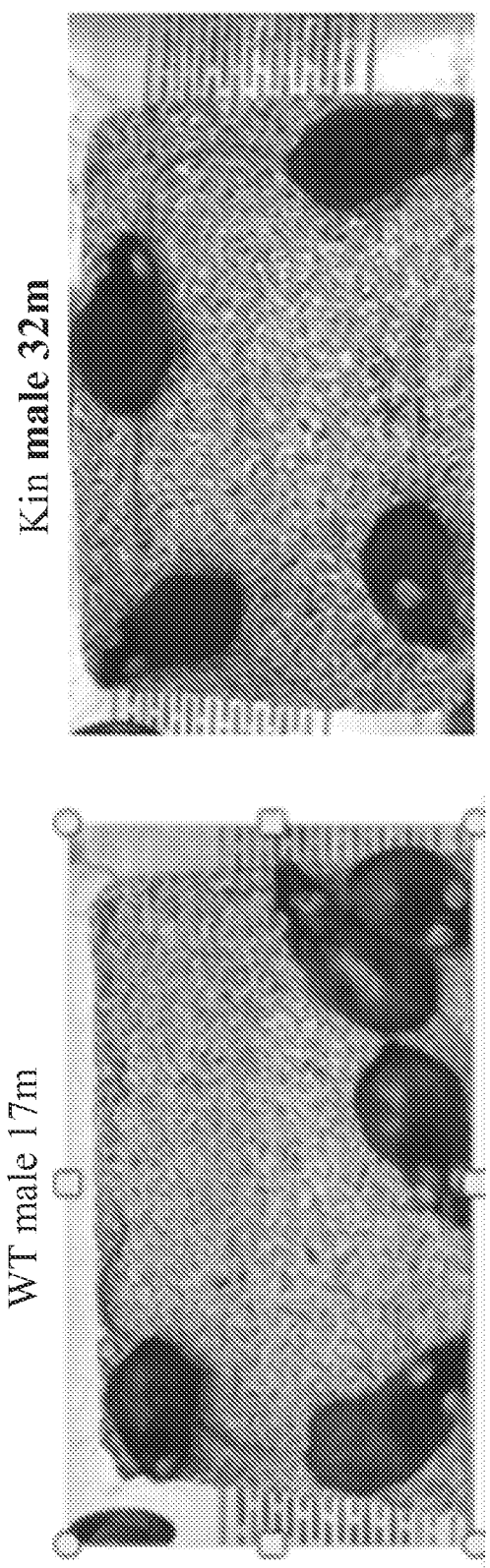

As evident from Table 1, the maximum lifespan (mean lifespan of the oldest 10% within a cohort) of the EKLF K74R male mice increased by 6.5 months compared to wild-type littermates. The maximum lifespan of EKLF K74R mice was about 40 months, which was longer than other longevity mice reported in the literature, e.g., CISD2 (Wu et al., Human Molecular Genetics (2012) 21, 3965-3968). Furthermore, 32 month-old EKLF K74R mice had less grey hairs compared with that of the 17 month-old wild-type mice (FIG. 3B). The EKLF K74R mice were found to be healthy and grew normally, in addition to their long life span.

Figure 4A:
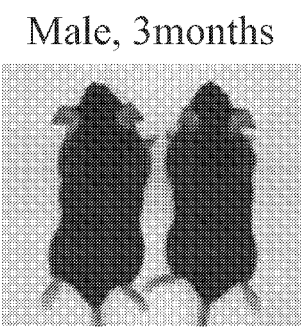
FIGS. 4A-4D show analysis of wild-type (WT) and EKLF K74R (Kin) metabolism.
Figure 4B:
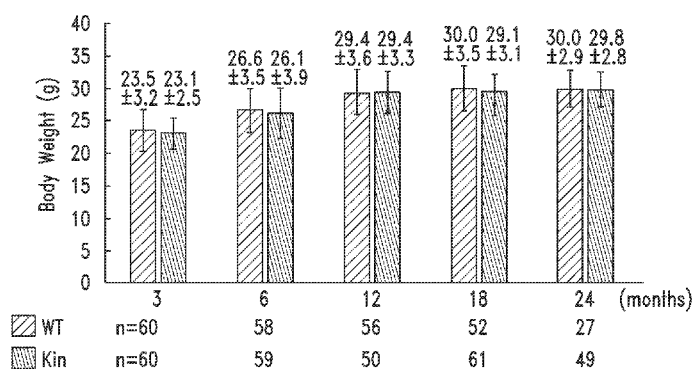
Figure 4C:
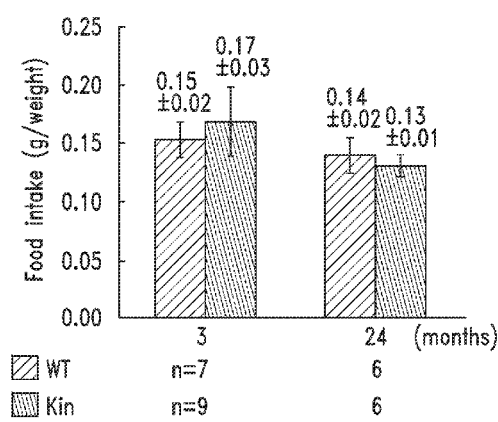
Figure 4D:
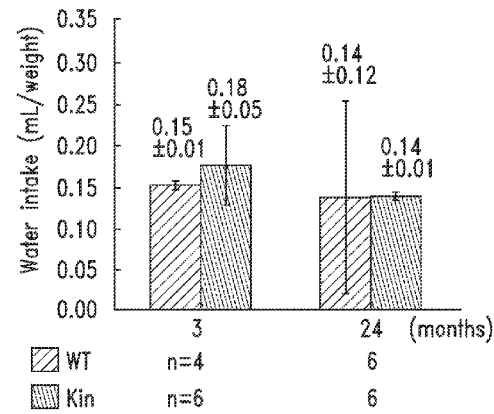

Dietary restriction or caloric restriction has been performed on a variety of species, including the yeast, fish, rodents and dogs, to decelerate the biological aging process, resulting in increased lifespan and health span. Direct change of the metabolism also been reported to extended lifespan. Preliminary data of small-scale phenotypic analysis of mice on the normal chow diet are shown in FIGS. 4 and 5. As seen, the patterns of the body weight changes of both wild-type and EKLF K74R mice between 3 months to 24 months of age were similar (FIG. 4B). Indeed, 48-hour spontaneous food intake, either normalized to body weight or expressed as an absolute value, was similar between wild-type and EKLF K74R mice, as was the water intake (FIGS. 4C and 4D).

Figure 5A:
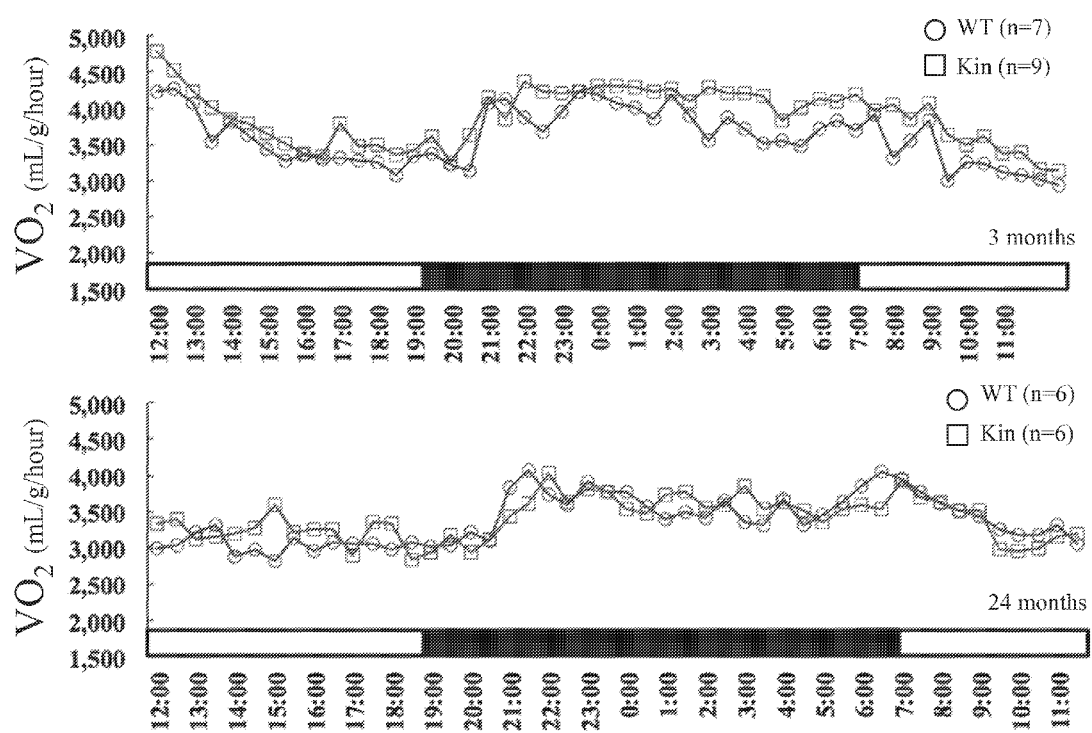
FIGS. 5A-5D show comparisons of whole-body energy expenditures of wild-type (WT) and EKLF K74R (Kin) mice. The canonical diurnal metabolic parameters measured for the 3-month and 24-month old mice include $VO_2$ (FIG. 5A), $VCO_2$ (FIG. 5B), heat production (FIG. 5C) and respiratory exchange ratio (RER) (FIG. 5D). The data are presented as means±SEM. Statistical significance was assessed by the two-tailed Student's t-test.
Figure 5B:
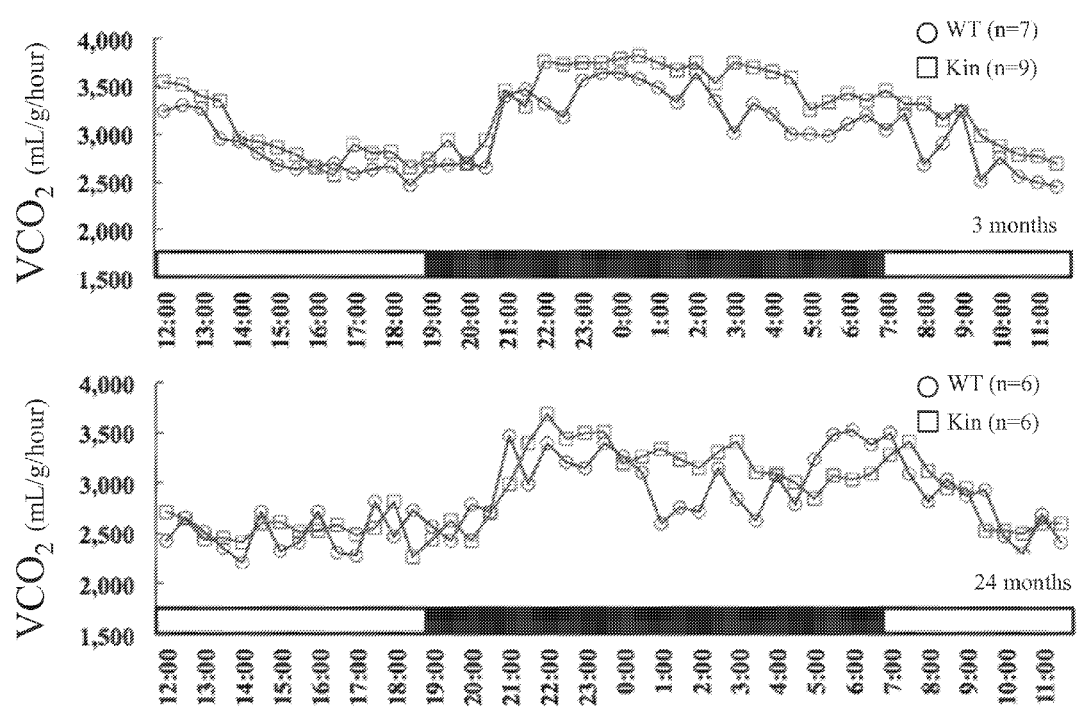
Figure 5C:
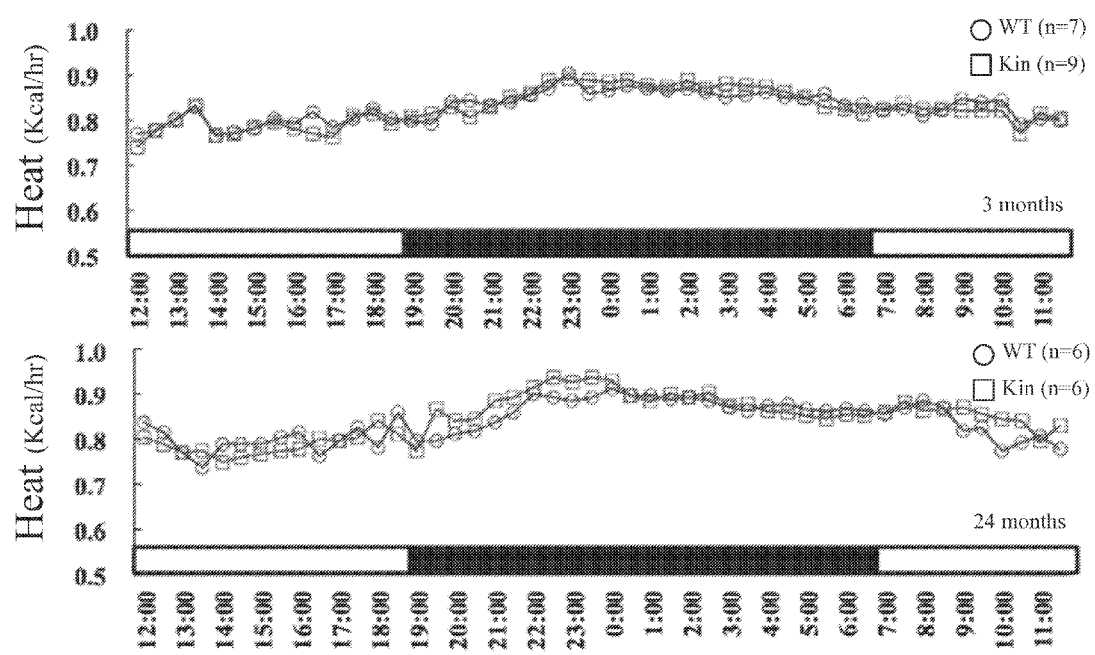
Figure 5D:
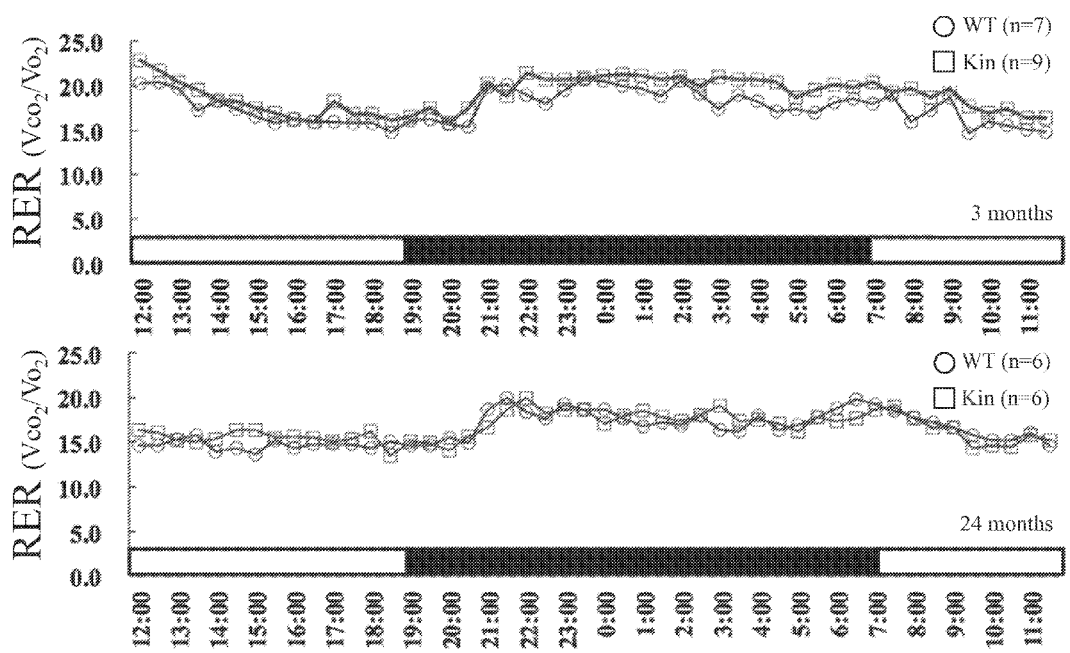

Normal chow-fed mice did not show obvious alterations of metabolic phenotypes, such as the oxygen consumption ($VO_2$, FIG. 5A), carbon dioxide production ($VCO_2$, FIG. 5B), heat production (FIG. 5C), and respiratory exchange ratio (RER) (FIG. 5D). These data suggested similar use of lipids and carbohydrates as the energetic fuel sources in EKLF K74R mice as the wild-type.

Figure 6C:
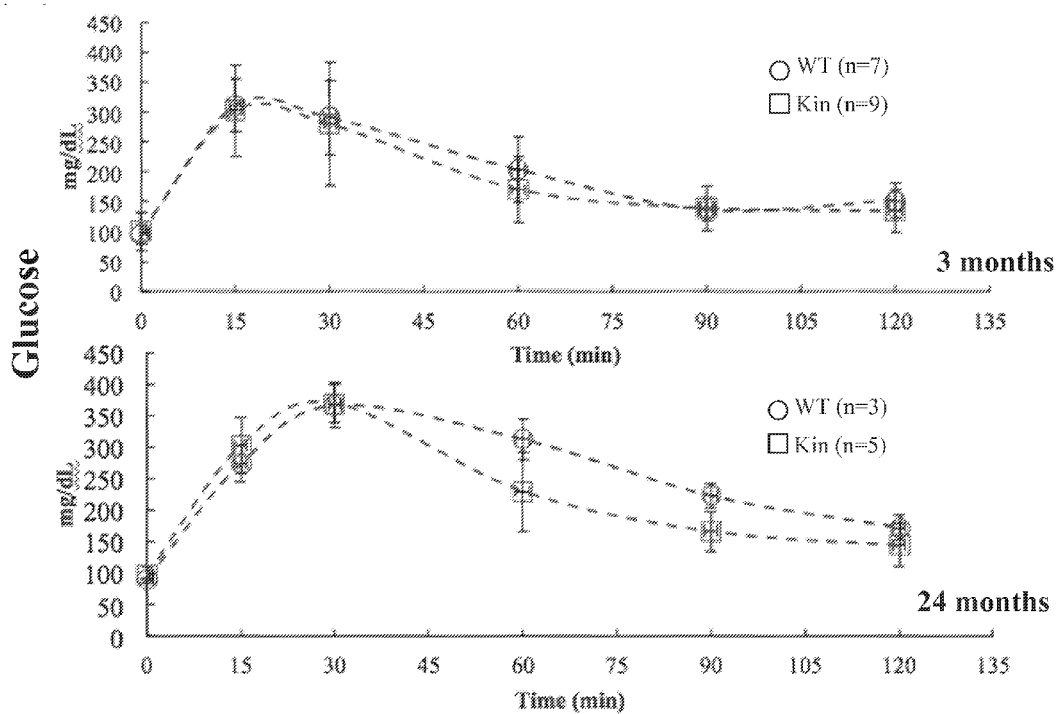

Since dietary restriction or caloric restriction is often associated with alterations in glucose tolerance, we measured the blood concentration of fasting glucose and fasting insulin, as well as the ability to clear glucose from the circulation in normal chow-fed mice. As seen in FIG. 6, there was no significant difference in fasting glucose concentration (FIG. 6A), fasting insulin concentration (FIG. 6B) or glucose tolerance (FIG. 6C) between the EKLF K74R and wild-type mice.

Tests were performed to evaluate muscle strength and motor coordination. The 3-month old EKLF K74R mice exhibited similar grip strength as the 3-month old wild-type mice, but a significant increase of grip strength was observed for the 24-month old EKLF K74R mice when compared to wild-type mice of the same age (FIG. 7A). On the other hand, the latencies to fall from rotarod were similar between EKLF K74R mice and wild-type mice of either 3-month or 12-month of age (FIG. 7B). The latency to fall from an accelerating rotarod was measured in three trials per day.

Figure 8:
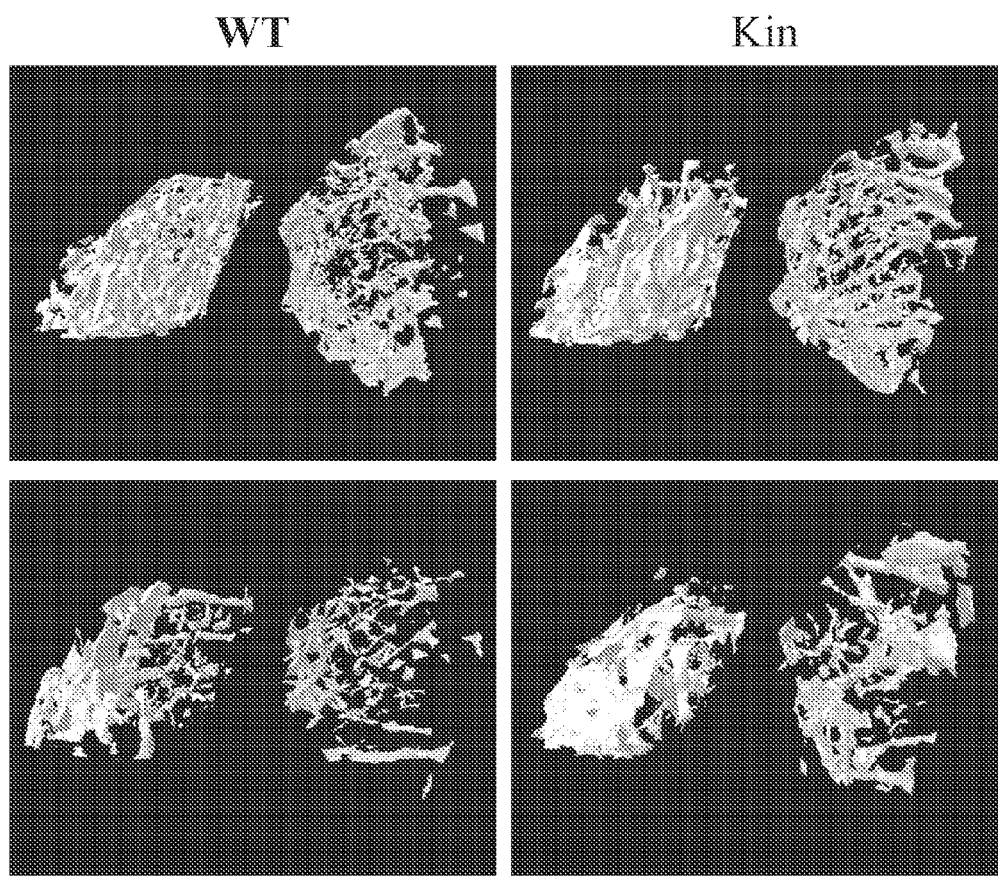
FIG. 8 shows an assessment of osteoporosis in male mice. The trabecular bones of wild-type (WT; left panels) and EKLF K74R (Kin; right panels) mice of the age of 3 months (top panels) or 24 months (bottom panels) were analyzed by high-resolution micro-computed tomography (mCT) imaging. n=3-6.

An important component of aging is osteoporosis. As seen in FIG. 8, both bone volume and trabecular number declined with age in wild-type mice, whereas the trabecular spacing increased (FIG. 8, left panels). On the contrary, all these parameters of old EKLF K74R mice were indistinguishable from the young EKLF K74R animals, indicating that EKLF K74R mice did not develop osteoporosis when aging (FIG. 8; right panels).

The phenotypes observed in EKLF K74R mice differ from previously described long-lived mouse models. Table E3 shows a phenotype comparison of the EKLF K74R mice to other known longevity rodent models. Upward arrows indicate increase, downward arrows indicate decrease, and equal signs indicate no change, as compared to the wild-type mice. For the column of "Aging", the comparison is for the old wild-type mice relative to the young wild-type mice. This table is modified from Table S7 of Hofmann, et al. (2015) Cell 160, 477-488.

TABLE E3

Phenotypes of Mouse Models of Longevity

| | | | | Insulin Signaling | | | | | | |
|---|---|---|---|---|---|---|---|---|---|---|
| | | | | IGF1 | | | | mTOR | | |
| | Aging | EKLF K74R | CR | Metformin | IGF1R+/− | Pappa−/− | Pten Tg | Myc+/− | Mtor tg | Rapamycin | S6K1−/− |
| Median lifespan | | ↑ | ↑ | ↑ | ↑ | ↑ | ↑ | ↑ | ↑ | ↑ | ↑ |
| Maximum lifespan | ↓ | ↑ | ↑ | ↑= | = | ↑ | ↑ | ↑ | ↑ | ↑ | ↑ |
| Body Mass | ↑ | = | ↓ | ↑↓ | ↓ | ↓ | ↓ | ↓ | ↓ | ↓ | ↓ |
| Adiposity | ↑ | = | ↓ | = | | | ↓ | = | = | = | ↓ |
| Body Temp | = | | ↓ | ↑ | | | = | = | | = | |
| Cholesterol | ↑ | = | ↓ | ↓ | | = | ↓ | ↓ | | ↑ | |
| Cancer | ↑ | ↓ | ↓ | ↓ | = | ↓ | ↓ | ↓ | ↓ | ↓ | = |
| Serum IGF-1 | = | | ↓ | ↓ | ↑ | = | ↓ | ↓ | | | = |
| Fibrosis | ↑ | | ↓ | ↓ | | | | | = | = | |
| DNA damage | ↑ | | ↓ | ↓ | | | | | = | = | |
| Endogenous oxidative stress | ↑ | | ↓ | ↓ | | | | | = | ↓ | = |
| Susceptibility to chemical stress | ↑ | ↓ | | ↑ | ↑↓ | | | | = | | |
| Fertility | ↓ | = | ↓ | | = | ↓ | | = | | ↓ | |
| Motor coordination | ↓ | ↑ | ↑ | ↑ | | | | ↑ | ↑ | ↑ | = | ↑ |

TABLE E3-continued

Phenotypes of Mouse Models of Longevity

| | | | | | | | | | |
|---|---|---|---|---|---|---|---|---|---|
| Bone density | ↓ | ↑ | ↑↓ | | | | ↑ | ↓ | = | ↑ |
| Senescence | ↑ | | ↓ | | | | = | | | |
| Apoptosis | ↑ | | ↑ | ↑ | ↓ | | = | | = | |
| Mitochondrial number | = | | = | = | | | ↑ | ↑= | = | |
| Inflammation | | ↓ | | | | | | | ↓ | |
| Susceptibility to infection | ↑ | ↓ | ↑ | | | | | ↑ | ↓ | |

| | Fat10−/− | Autophagy Sirt1 Tg | Atg5 | Gene stability p53 Tg | Mitochondria Cisd2 Tg |
|---|---|---|---|---|---|
| Median lifespan | ↑ | ↑ | ↑ | ↓ | ↑ |
| Maximum lifespan | ↑ | ↑ | ↑ | ↓ | ↑ |
| Body Mass | ↓ | = | ↓ | ↓ | = |
| Adiposity | ↓ | | ↓ | | ↑ |
| Body Temp | = | ↑ | = | | = |
| Cholesterol | ↓= | | | | |
| Cancer | ↓ | = | = | ↑ | |
| Serum IGF-1 | | = | | | |
| Fibrosis | | | | ↓ | |
| DNA damage | | | | | |
| Endogenous oxidative stress | | | | | = |
| Susceptibility to chemical stress | | | | | |
| Fertility | | = | | | |
| Motor coordination | | ↑ | ↑ | | ↑ |
| Bone density | | | | ↓ | |
| Senescence | | | | | ↓ |
| Apoptosis | | | | | ↓ |
| Mitochondrial number | | ↑ | | | ↑ |
| Inflammation | ↓ | | | ↑ | |
| Susceptibility to infection | ↑ | | | | |

Example 3

EKLF K74R Mutation Leads to Cancer Resistance

Figures 9A, 9B:
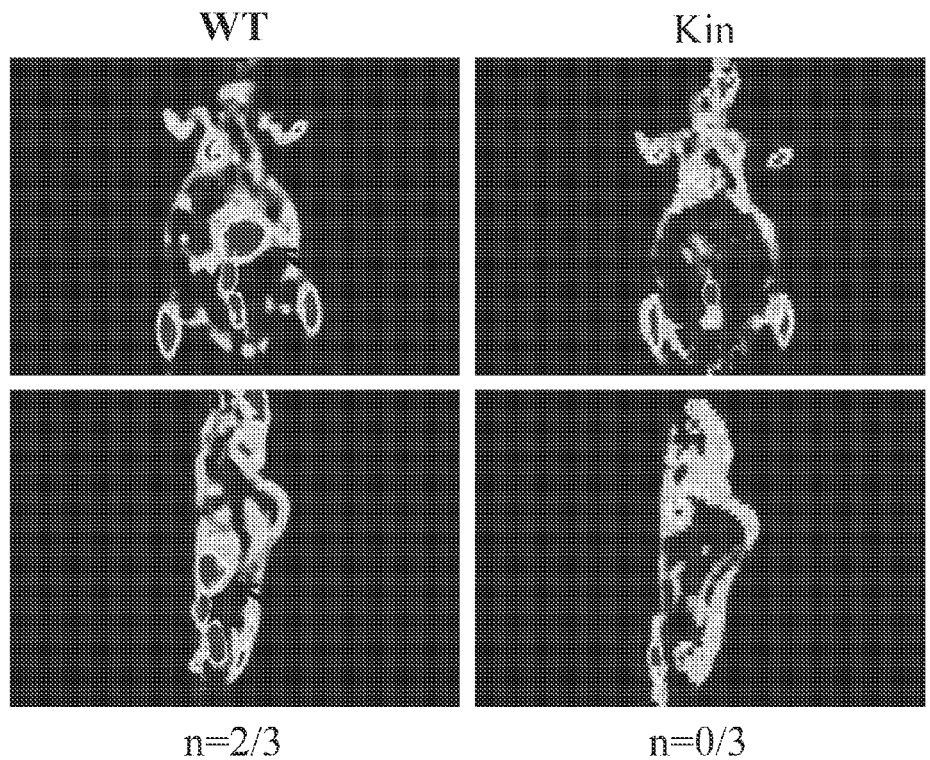
FIGS. 9A and 9B show MicroPET images of 24-month old wild-type (WT) and EKLF K74R (Tg) mice.

Phenotypic observations showed lower age-related cancer incidence rates in the EKLF K74R mice than in wild-type littermates, as exemplified by the Micro-PET imaging analysis (FIG. 9A) and examination of dissected 24-month old mice (FIG. 9B).

Figures 10A, 10B:
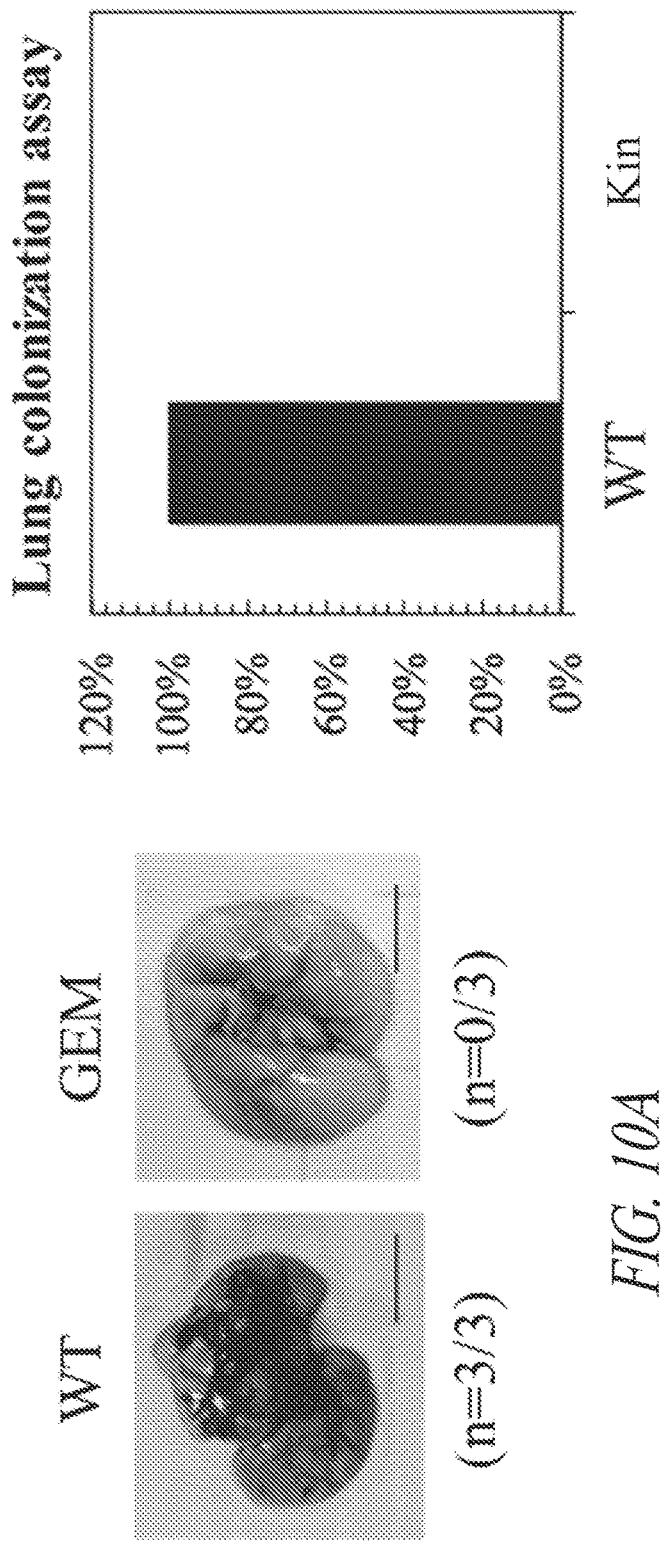
FIGS. 10A and 10B show the anti-carcinogenesis capability of the EKLF K74R mice.

Cancer cells were implanted in EKLF K74R mice and wild-type littermates by intravenous injection. B16F10 melanoma cells (ATCC# CRL6475) were derived from the same (C57BL/6J) genetic background as the EKLF K74R mice. An in vivo metastasis assay was performed by tail vein injection (i.v. injection) of B16F10 cells into the mice (FIG. 10). Lungs were examined 2 weeks after injection of the B16F10 cells. These data indicate that the EKLF K74R mice have reduced incidence of cancer occurrence. A preliminary study showed a non-statistically significant small trend towards reduced tumor growth in Kin mice when the B16F10 melanoma cells were injected into the mice subcutaneously.

Together, these data showed a lower cancer incidence rate in the EKLF K74R mice (FIG. 9), which correlated well with the data of the lung tumorassay (FIG. 10). These data are consistent with EKLF K74R reducing or inhibiting tumor occurrence and reducing or inhibiting the metastasis of the cancer cells.

The detailed description provided herein in connection with the appended drawings is intended as a description of the present examples and is not intended to represent the only forms in which the present invention may be constructed or utilized. The description sets forth certain functions of the example and the sequence of steps for constructing and operating the example. However, the same or equivalent functions and sequences may be accomplished by different examples. The various embodiments described herein can be combined to provide further embodiments. Aspects of the embodiments can be modified, if necessary, to employ concepts of the various patents, applications and publications described herein to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety.

What is claimed is:

1. A method of inhibiting a cellular proliferative disorder, or reducing the incidence of tumor occurrence or tumor metastasis, in a subject in need thereof, comprising administering to the subject an effective amount of:
a modified Erythroid Kruppel-like factor (EKLF) polypeptide comprising an amino acid modification that confers reduced sumoylation in a wild-type EKLF polypeptide, wherein the amino acid modification is a substitution of lysine with arginine at the amino acid position 54 (K54R) of a wild-type EKLF polypeptide of SEQ ID NO: 3.

2. The method of claim 1, wherein the polypeptide is administered, and the modified EKLF polypeptide has reduced translocation from the cytoplasm to the nucleus as compared to the wild-type EKLF polypeptide.

3. The method of claim 2, wherein the polypeptide is administered, and the modified EKLF polypeptide has a modified transactivator activity or a modified repressor activity as compared to the wild-type EKLF polypeptide.

4. The method of claim 1, wherein the modified EKLF polypeptide of the wild-type mouse EKLF polypeptide of SEQ ID NO: 3 further comprises a modification at position 68.

5. The method of claim 1, wherein the cellular proliferative disorder, tumor or tumor metastasis is a liver cancer, a colon cancer, a breast cancer, a prostate cancer, a hepatocellular carcinoma, a melanoma, a lung cancer, a glioblastoma, a brain tumor, a hematopoetic malignancy, a cholangiocarcinoma, a retinoblastoma, a renal cell carcinoma, a head and neck cancer, a cervical cancer, a pancreatic cancer, an esophageal cancer, or a squamous cell carcinoma.

* * * * *

SEQUENCE LISTING

<160> NUMBER OF SEQ ID NOS: 10

<210> SEQ ID NO 1
<211> LENGTH: 376
<212> TYPE: PRT
<213> ORGANISM: Mus musculus

<400> SEQUENCE: 1

Met Arg Gln Lys Arg Glu Arg Pro Glu Val Gln Gly Gly His Gln
1               5                   10                  15

Pro Ala Met Ala Ser Ala Glu Thr Val Leu Pro Ser Ile Ser Thr Leu
            20                  25                  30

Thr Thr Leu Gly Gln Phe Leu Asp Thr Gln Glu Asp Phe Leu Lys Trp
        35                  40                  45

Trp Arg Ser Glu Glu Thr Gln Asp Leu Gly Pro Gly Pro Pro Asn Pro
    50                  55                  60

Thr Gly Pro Ser His His Val Ser Leu Lys Ser Glu Asp Pro Ser Gly
65                  70                  75                  80

Glu Asp Asp Glu Arg Asp Val Thr Cys Ala Trp Asp Pro Asp Leu Phe
                85                  90                  95

Leu Thr Asn Phe Pro Gly Ser Glu Ser Pro Gly Thr Ser Arg Thr Cys
            100                 105                 110

Ala Leu Ala Pro Ser Val Gly Pro Val Ala Gln Phe Glu Pro Pro Glu
        115                 120                 125

Ser Leu Gly Ala Tyr Ala Gly Gly Pro Gly Leu Val Thr Gly Pro Leu
    130                 135                 140

Gly Ser Glu Glu His Thr Ser Trp Ala His Pro Thr Pro Arg Pro Pro
145                 150                 155                 160

Ala Pro Glu Pro Phe Val Ala Pro Ala Leu Ala Pro Gly Leu Ala Pro
                165                 170                 175

Lys Ala Gln Pro Ser Tyr Ser Asp Ser Arg Ala Gly Ser Val Gly Gly
            180                 185                 190

Phe Phe Pro Arg Ala Gly Leu Ala Val Pro Ala Ala Pro Gly Ala Pro
        195                 200                 205

Tyr Gly Leu Leu Ser Gly Tyr Pro Ala Leu Tyr Pro Ala Pro Gln Tyr
    210                 215                 220

Gln Gly His Phe Gln Leu Phe Arg Gly Leu Ala Ala Pro Ser Ala Gly
225                 230                 235                 240

Pro Thr Ala Pro Pro Ser Phe Leu Asn Cys Leu Gly Pro Gly Thr Val
                245                 250                 255

Ala Thr Glu Leu Gly Ala Thr Ala Ile Ala Gly Asp Ala Gly Leu Ser
            260                 265                 270

Pro Gly Thr Ala Pro Pro Lys Arg Ser Arg Arg Thr Leu Ala Pro Lys
        275                 280                 285

Arg Gln Ala Ala His Thr Cys Gly His Glu Gly Cys Gly Lys Ser Tyr
    290                 295                 300

Thr Lys Ser Ser His Leu Lys Ala His Leu Arg Thr His Thr Gly Glu
305                 310                 315                 320

Lys Pro Tyr Ala Cys Ser Trp Asp Gly Cys Asp Trp Arg Phe Ala Arg
                325                 330                 335

Ser Asp Glu Leu Thr Arg His Tyr Arg Lys His Thr Gly His Arg Pro
            340                 345                 350

Phe Cys Cys Gly Leu Cys Pro Arg Ala Phe Ser Arg Ser Asp His Leu
        355                 360                 365

```
Ala Leu His Met Lys Arg His Leu
    370                 375

<210> SEQ ID NO 2
<211> LENGTH: 376
<212> TYPE: PRT
<213> ORGANISM: Rattus norvegicus

<400> SEQUENCE: 2

Met Arg Gln Lys Arg Glu Arg Pro Glu Ala Gln Gly Gly Gln Gln
1               5                   10                  15

Pro Val Met Ala Ser Ala Glu Thr Val Leu Pro Ser Ile Ser Thr Leu
            20                  25                  30

Thr Thr Leu Gly Gln Phe Leu Asp Thr Gln Glu Asp Phe Leu Lys Trp
        35                  40                  45

Trp Arg Ser Glu Glu Thr Gln Asp Leu Gly Pro Gly Pro Pro Asn Pro
    50                  55                  60

Thr Glu Pro Ser Phe His Val Ser Leu Lys Ser Glu Asp Pro Gly
65                  70                  75                  80

Glu Asp Asp Glu Arg Asp Val Thr Cys Ala Trp Asp Pro Asp Leu Phe
                85                  90                  95

Leu Thr Asn Phe Ser Gly Pro Glu Pro Pro Ser Thr Pro Arg Thr Cys
            100                 105                 110

Ala Leu Ala Pro Ser Gly Gly Pro Val Ala Gln Phe Ala Pro Pro Glu
        115                 120                 125

Ser Leu Ser Ala Tyr Ala Gly Gly Pro Gly Leu Val Thr Gly Pro Leu
        130                 135                 140

Gly Ser Glu Glu His Ala Gly Trp Ala His Pro Thr Pro Arg Pro Pro
145                 150                 155                 160

Thr Pro Glu Pro Phe Val Ala Pro Val Leu Ala Pro Gly Leu Ala Pro
                165                 170                 175

Lys Ala Gln Pro Ala Phe Ser Glu Ser Arg Ala Val Ser Ala Gly Gly
            180                 185                 190

Phe Phe Pro Arg Ala Gly Leu Ala Val Pro Ala Ala Pro Ser Ala Pro
        195                 200                 205

Tyr Gly Leu Leu Ser Gly Tyr Pro Ala Leu Tyr Pro Ala Pro Gln Tyr
        210                 215                 220

Gln Gly His Phe Gln Leu Phe Arg Gly Leu Ala Ala Pro Ser Ala Gly
225                 230                 235                 240

Pro Thr Ala Pro Pro Ser Phe Leu Asn Cys Leu Gly Pro Gly Ala Val
                245                 250                 255

Gly Thr Glu Leu Gly Ala Thr Ala Ile Ala Gly Asp Ala Gly Leu Ser
            260                 265                 270

Pro Gly Ala Ala Pro Pro Lys Arg Ser Arg Arg Thr Leu Ala Gln Lys
        275                 280                 285

Arg Gln Ala Ala His Thr Cys Gly His Glu Gly Cys Gly Lys Ser Tyr
    290                 295                 300

Thr Lys Ser Ser His Leu Lys Ala His Leu Arg Thr His Thr Gly Glu
305                 310                 315                 320

Lys Pro Tyr Ala Cys Ser Trp Asp Gly Cys Asn Trp Arg Phe Ala Arg
                325                 330                 335

Ser Asp Glu Leu Thr Arg His Tyr Arg Lys His Thr Gly His Arg Pro
            340                 345                 350

Phe Cys Cys Gly Leu Cys Pro Arg Ala Phe Ser Arg Ser Asp His Leu
        355                 360                 365
```

```
Ala Leu His Met Lys Arg His Leu
    370             375
```

<210> SEQ ID NO 3
<211> LENGTH: 362
<212> TYPE: PRT
<213> ORGANISM: Homo sapients

<400> SEQUENCE: 3

```
Met Ala Thr Ala Glu Thr Ala Leu Pro Ser Ile Ser Thr Leu Thr Ala
1               5                   10                  15

Leu Gly Pro Phe Pro Asp Thr Gln Asp Asp Phe Leu Lys Trp Trp Arg
            20                  25                  30

Ser Glu Glu Ala Gln Asp Met Gly Pro Gly Pro Pro Asp Pro Thr Glu
        35                  40                  45

Pro Pro Leu His Val Lys Ser Glu Asp Gln Pro Gly Glu Glu Glu Asp
    50                  55                  60

Asp Glu Arg Gly Ala Asp Ala Thr Trp Asp Leu Asp Leu Leu Leu Thr
65                  70                  75                  80

Asn Phe Ser Gly Pro Glu Pro Gly Gly Ala Pro Gln Thr Cys Ala Leu
                85                  90                  95

Ala Pro Ser Glu Ala Ser Gly Ala Gln Tyr Pro Pro Pro Pro Glu Thr
            100                 105                 110

Leu Gly Ala Tyr Ala Gly Gly Pro Gly Leu Val Ala Gly Leu Leu Gly
        115                 120                 125

Ser Glu Asp His Ser Gly Trp Val Arg Pro Ala Leu Arg Ala Arg Ala
    130                 135                 140

Pro Asp Ala Phe Val Gly Pro Ala Leu Ala Pro Ala Pro Ala Pro Glu
145                 150                 155                 160

Pro Lys Ala Leu Ala Leu Gln Pro Val Tyr Pro Gly Pro Gly Ala Gly
                165                 170                 175

Ser Ser Gly Gly Tyr Phe Pro Arg Thr Gly Leu Ser Val Pro Ala Ala
            180                 185                 190

Ser Gly Ala Pro Tyr Gly Leu Leu Ser Gly Tyr Pro Ala Met Tyr Pro
        195                 200                 205

Ala Pro Gln Tyr Gln Gly His Phe Gln Leu Phe Arg Gly Leu Gln Gly
    210                 215                 220

Pro Ala Pro Gly Pro Ala Thr Ser Pro Ser Phe Leu Ser Cys Leu Gly
225                 230                 235                 240

Pro Gly Thr Val Gly Thr Gly Leu Gly Gly Thr Ala Glu Asp Pro Gly
                245                 250                 255

Val Ile Ala Glu Thr Ala Pro Ser Lys Arg Gly Arg Arg Ser Trp Ala
            260                 265                 270

Arg Lys Arg Gln Ala Ala His Thr Cys Ala His Pro Gly Cys Gly Lys
        275                 280                 285

Ser Tyr Thr Lys Ser Ser His Leu Lys Ala His Leu Arg Thr His Thr
    290                 295                 300

Gly Glu Lys Pro Tyr Ala Cys Thr Trp Glu Gly Cys Gly Trp Arg Phe
305                 310                 315                 320

Ala Arg Ser Asp Glu Leu Thr Arg His Tyr Arg Lys His Thr Gly Gln
                325                 330                 335

Arg Pro Phe Arg Cys Gln Leu Cys Pro Arg Ala Phe Ser Arg Ser Asp
            340                 345                 350

His Leu Ala Leu His Met Lys Arg His Leu
```

<210> SEQ ID NO 4
<211> LENGTH: 362
<212> TYPE: PRT
<213> ORGANISM: Pan troglodytes

<400> SEQUENCE: 4

Met Ala Thr Ala Glu Thr Ala Leu Pro Ser Ile Ser Thr Leu Thr Ala
1               5                   10                  15

Leu Gly Pro Phe Pro Asp Thr Gln Asp Asp Phe Leu Lys Trp Trp Arg
            20                  25                  30

Ser Glu Glu Ala Gln Asp Met Gly Pro Gly Pro Asp Pro Thr Glu
        35                  40                  45

Pro Pro Leu His Val Lys Ser Glu Asp Gln Pro Gly Glu Glu Glu Asp
    50                  55                  60

Asp Glu Arg Gly Ala Asp Ala Thr Trp Asp Leu Asp Leu Leu Leu Thr
65                  70                  75                  80

Asn Phe Ser Gly Pro Glu Pro Gly Gly Ala Pro Gln Thr Cys Ala Leu
                85                  90                  95

Ala Pro Ser Glu Ala Pro Gly Ala Gln Tyr Pro Pro Pro Glu Thr
            100                 105                 110

Leu Gly Ala Tyr Ala Gly Gly Pro Gly Leu Val Ala Gly Leu Leu Gly
            115                 120                 125

Ser Glu Asp His Ser Gly Trp Val Arg Pro Ala Leu Arg Ala Arg Ala
130                 135                 140

Pro Asp Ala Phe Val Gly Pro Ala Leu Ala Pro Ala Pro Ala Pro Glu
145                 150                 155                 160

Pro Lys Ala Leu Ala Leu Gln Pro Val Tyr Pro Gly Pro Gly Ala Gly
                165                 170                 175

Ser Ser Gly Gly Tyr Phe Pro Arg Thr Gly Leu Ser Val Pro Ala Ala
            180                 185                 190

Ser Gly Ala Pro Tyr Gly Leu Leu Ser Gly Tyr Pro Ala Met Tyr Pro
        195                 200                 205

Ala Pro Gln Tyr Gln Gly His Phe Gln Leu Phe Arg Gly Leu Gln Gly
    210                 215                 220

Pro Ala Pro Gly Pro Ala Thr Ser Pro Ser Phe Leu Ser Cys Leu Gly
225                 230                 235                 240

Pro Gly Thr Val Gly Thr Gly Leu Gly Gly Thr Ala Glu Asp Pro Gly
                245                 250                 255

Val Ile Ala Glu Thr Ala Pro Ser Lys Arg Gly Arg Arg Ser Trp Ala
            260                 265                 270

Arg Lys Arg Gln Ala Ala His Thr Cys Ala His Pro Gly Cys Gly Lys
        275                 280                 285

Ser Tyr Thr Lys Ser Ser His Leu Lys Ala His Leu Arg Thr His Thr
290                 295                 300

Gly Glu Lys Pro Tyr Ala Cys Thr Trp Glu Gly Cys Gly Trp Arg Phe
305                 310                 315                 320

Ala Arg Ser Asp Glu Leu Thr Arg His Tyr Arg Lys His Thr Gly Gln
                325                 330                 335

Arg Pro Phe Arg Cys Gln Leu Cys Pro Arg Ala Phe Ser Arg Ser Asp
            340                 345                 350

His Leu Ala Leu His Met Lys Arg His Leu
        355                 360

<210> SEQ ID NO 5
<211> LENGTH: 362
<212> TYPE: PRT
<213> ORGANISM: Macaca mulatta

<400> SEQUENCE: 5

```
Met Ala Thr Ala Lys Thr Ala Leu Pro Ser Ile Ser Thr Leu Thr Ala
1               5                   10                  15

Leu Gly Pro Phe Pro Asp Thr Gln Asp Asp Phe Leu Lys Trp Trp Arg
            20                  25                  30

Ser Glu Glu Ala Gln Asp Met Gly Pro Gly Pro Pro Asp Pro Thr Glu
        35                  40                  45

Pro Pro Leu His Val Lys Ser Glu Asp Gln Pro Gly Glu Glu Glu Asp
    50                  55                  60

Asp Glu Arg Gly Ala Asp Ala Thr Trp Asp Leu Asp Leu Phe Leu Thr
65                  70                  75                  80

Asn Phe Ser Gly Pro Glu Pro Gly Gly Ala Pro Gln Thr Cys Ala Leu
                85                  90                  95

Ala Pro Ser Glu Ala Pro Gly Val Gln Tyr Pro Pro Pro Glu Thr
            100                 105                 110

Leu Gly Ala Tyr Ala Gly Gly Pro Gly Met Val Ala Gly Leu Leu Gly
            115                 120                 125

Ser Glu Asp His Ser Gly Trp Val Arg Pro Ala Leu Arg Ala Pro Ala
130                 135                 140

Pro Asp Ala Phe Val Gly Pro Ala Leu Ala Pro Ala Pro Ala Pro Glu
145                 150                 155                 160

Pro Lys Ala Leu Ala Leu Gln Pro Val Tyr Pro Gly Pro Gly Ala Gly
                165                 170                 175

Ser Ser Gly Gly Tyr Phe Gln Arg Thr Gly Leu Ser Val Pro Ala Ala
            180                 185                 190

Ser Gly Ala Pro Tyr Gly Leu Leu Ser Gly Tyr Pro Ala Val Tyr Pro
            195                 200                 205

Ala Pro Gln Tyr Gln Gly His Phe Gln Leu Phe Arg Gly Leu Gln Gly
    210                 215                 220

Pro Ala Pro Gly Pro Ala Thr Ser Pro Ser Phe Leu Ser Cys Leu Gly
225                 230                 235                 240

Pro Gly Thr Val Gly Thr Gly Leu Gly Gly Thr Ala Gly Asp Pro Gly
                245                 250                 255

Val Ile Ala Glu Ala Ala Pro Ser Lys Arg Gly Arg Arg Ser Trp Ala
            260                 265                 270

Arg Lys Arg Gln Ala Ala His Thr Cys Ala His Pro Gly Cys Gly Lys
        275                 280                 285

Ser Tyr Thr Lys Ser Ser His Leu Lys Ala His Leu Arg Thr His Thr
290                 295                 300

Gly Glu Lys Pro Tyr Ala Cys Thr Trp Glu Gly Cys Gly Trp Arg Phe
305                 310                 315                 320

Ala Arg Ser Asp Glu Leu Thr Arg His Tyr Arg Lys His Thr Gly Gln
                325                 330                 335

Arg Pro Phe Arg Cys Gln Leu Cys Pro Arg Ala Phe Ser Arg Ser Asp
            340                 345                 350

His Leu Ala Leu His Met Lys Arg His Leu
            355                 360
```

<210> SEQ ID NO 6

```
<211> LENGTH: 369
<212> TYPE: PRT
<213> ORGANISM: Canis lupus

<400> SEQUENCE: 6

Met Ala Thr Ala Glu Thr Ala Leu Pro Ser Ile Ser Thr Leu Thr Thr
1               5                   10                  15

Leu Gly Pro Phe Pro Asp Thr Gln Glu Asp Phe Leu Lys Trp Trp Arg
                20                  25                  30

Ser Glu Glu Val Gln Asp Leu Gly Pro Gly Pro Asp Pro Thr Gly
            35                  40                  45

Leu Pro Leu His Val Arg Pro Glu Ser Gln Asp Ala Pro Gly Glu Asp
    50                  55                  60

Glu Asp Asp Glu Arg Asp Ser Ala Thr Ala Trp Asp Leu Asp Leu Leu
65                  70                  75                  80

Leu Thr Asn Phe Pro Cys Pro Glu Pro Gly Gly Ala Pro Gln Thr Cys
                85                  90                  95

Ala Leu Ala Pro Gly Glu Cys Ser Gly Val Gln Phe Pro Pro Pro Pro
            100                 105                 110

Leu Pro Pro Pro Gln Ala Pro Glu Thr Pro Cys Pro Tyr Val Gly Gly
        115                 120                 125

Pro Gly Leu Val Ala Gly Leu Leu Gly Pro Glu Glu His Pro Gly Trp
    130                 135                 140

Ala Arg Pro Ala Pro Arg Ala Pro Val Pro Asp Ala Phe Val Gly Ser
145                 150                 155                 160

Ala Leu Gly Pro Ala Pro Glu Pro Lys Pro Leu Pro Leu Gln Pro Val
                165                 170                 175

Tyr Pro Gly Pro Gly Ala Gly Ser Ser Gly Ser Tyr Phe Ser Arg Thr
            180                 185                 190

Gly Leu Ser Val Pro Thr Ala Pro Gly Ala Pro Tyr Gly Leu Leu Pro
        195                 200                 205

Gly Tyr Pro Pro Leu Tyr Pro Val Pro Gln Tyr Gln Gly His Phe Gln
    210                 215                 220

Leu Phe Arg Gly Leu Pro Ala Pro Ala Pro Gly Pro Thr Ser Pro Pro
225                 230                 235                 240

Ser Phe Leu Ser Cys Leu Gly Pro Gly Thr Ala Gly Ser Gly Leu Arg
                245                 250                 255

Gly Thr Ala Gly Asp Pro Gly Gly Val Ala Asp Ala Ala Pro Ser Lys
            260                 265                 270

Arg Ser Arg Arg Ser Trp Ala Arg Lys Arg Gln Ala Ala His Thr Cys
        275                 280                 285

Thr His Pro Gly Cys Gly Lys Ser Tyr Thr Lys Ser Ser His Leu Lys
    290                 295                 300

Ala His Leu Arg Thr His Thr Gly Glu Lys Pro Tyr Ala Cys Thr Trp
305                 310                 315                 320

Asp Gly Cys Gly Trp Arg Phe Ala Arg Ser Asp Glu Leu Thr Arg His
                325                 330                 335

Tyr Arg Lys His Thr Gly Gln Arg Pro Phe Arg Cys Gln Leu Cys Pro
            340                 345                 350

Arg Ala Phe Ser Arg Ser Asp His Leu Ala Leu His Met Lys Arg His
        355                 360                 365

Leu

<210> SEQ ID NO 7
```

```
<211> LENGTH: 372
<212> TYPE: PRT
<213> ORGANISM: Bos taurus

<400> SEQUENCE: 7
```

| | | | | | | | | | | | | | | |
|---|---|---|---|---|---|---|---|---|---|---|---|---|---|---|
| Met | Ala | Ala | Ala | Glu | Thr | Ala | Leu | Pro | Ser | Ile | Ser | Thr | Leu | Thr | Ala |
| 1 | | | | 5 | | | | | 10 | | | | | 15 | |

Leu Gly Pro Phe Ser Asp Thr Gln Glu Asp Ile Leu Lys Trp Trp Arg
            20                  25                  30

Ser Glu Asp Val Gln Asp Leu Gly Pro Gly Pro Asp His Thr Gly
        35                  40                  45

Pro Pro Leu His Val Arg Pro Glu Leu Glu Asp Ala Pro Gly Glu Asp
    50                  55                  60

Glu Asp Asp Asp Arg Asp Ala Ala Thr Pro Trp Asp Leu Asp Leu Leu
65                  70                  75                  80

Phe Thr Asn Phe Pro Cys Pro Glu Pro Gly Gly Ala Pro Gln Thr Cys
                85                  90                  95

Ala Pro Gln Thr Cys Ala Pro Gln Ala Cys Ala Leu Ala Pro Ser Glu
            100                 105                 110

Gly Ser Gly Ala Gln Phe Pro Pro Pro Glu Thr Leu Gly Ala Tyr
        115                 120                 125

Ala Gly Gly Pro Gly Leu Val Ala Gly Leu Leu Gly Pro Glu Glu His
    130                 135                 140

Leu Gly Trp Ala Arg Pro Ala Pro Arg Thr Pro Ala Pro Asp Thr Phe
145                 150                 155                 160

Val Gly Pro Ser Leu Ile Pro Thr Pro Glu Pro Lys Ala Leu Pro Leu
                165                 170                 175

Gln Pro Leu Tyr Pro Gly Pro Gly Ser Gly Ser Ser Gly Ser Tyr Phe
            180                 185                 190

Pro Arg Thr Gly Leu Ser Val Pro Ala Ala Pro Gly Ala Pro Tyr Gly
        195                 200                 205

Leu Leu Ser Gly Tyr Pro Ala Leu Tyr Pro Met Pro Gln Tyr Gln Gly
    210                 215                 220

His Phe Gln Leu Phe Arg Gly Leu Gln Ala Pro Ala Pro Gly Pro Pro
225                 230                 235                 240

Ser Pro His Ser Phe Leu Ser Cys Leu Gly Pro Gly Thr Thr Gly Ala
                245                 250                 255

Gly Leu Gly Gly Thr Thr Gly Asp Pro Gly Gly Thr Thr Glu Ala Ala
            260                 265                 270

Pro Ser Lys Arg Ser Arg Arg Ser Trp Ala Arg Lys Arg Gln Ala Ala
        275                 280                 285

His Thr Cys Thr His Pro Gly Cys Gly Lys Ser Tyr Thr Lys Ser Ser
    290                 295                 300

His Leu Lys Ala His Leu Arg Thr His Thr Gly Glu Lys Pro Tyr Ala
305                 310                 315                 320

Cys Thr Trp Asp Gly Cys Gly Trp Arg Phe Ala Arg Ser Asp Glu Leu
                325                 330                 335

Thr Arg His Tyr Arg Lys His Thr Gly Gln Arg Pro Phe Arg Cys Gln
            340                 345                 350

Leu Cys Ser Arg Ala Phe Ser Arg Ser Asp His Leu Ala Leu His Met
        355                 360                 365

Lys Arg His Leu
    370

<210> SEQ ID NO 8
<211> LENGTH: 4946
<212> TYPE: DNA
<213> ORGANISM: Artificial Sequence
<220> FEATURE:
<223> OTHER INFORMATION: EKLF-PGK knock-in cassette

<400> SEQUENCE: 8

| | | | | | |
|---|---|---|---|---|---|
| gtgggcagac | aggagccctc | caagaaactt | tcctagcctc | atagcccatg | aggcagaaga | 60 |
| gagagaggag | gcctgaggtc | cagggtggac | accagccagc | catggcctca | gctgagactg | 120 |
| tcttaccctc | catcagtaca | ctcaccaccc | tgggacagtt | cctggacacc | caggaggact | 180 |
| tcctcaaggt | ggggccagtg | tgagtgtgtg | ggagggggca | ggtggtcttg | catagggcat | 240 |
| agtgcttagg | ggtggggcgt | ctatcttact | ttaatatcct | ctgctctgtt | ttttgggggt | 300 |
| ggaggagtgg | gagagcctct | gagccttgtt | tgggggagag | gttctagggg | tctgagatca | 360 |
| aggtgaggtg | acactataga | atactcaagc | tatcgagata | acttcgtata | atgtatgcta | 420 |
| tacgaagtta | tcgcgccgca | cacaaaaacc | aacacacaga | tcatgaaaat | aaagctcttt | 480 |
| tattggtacc | gaattcgcca | gggagctctc | agacgtcgct | tggtcggtct | ttattcgaac | 540 |
| cccagagtcc | cgctcagaag | aactcgtcaa | gaaggcgata | gaaggcgatg | cgctgcgaat | 600 |
| cggggcggc | gataccgtaa | agcacgagga | agcggtcagc | ccattcgccg | ccaagctctt | 660 |
| cagcaatatc | acgggtagcc | aacgctatgt | cctgatagcg | gtccgccaca | cccagccggc | 720 |
| cacagtcgat | gaatccagaa | aagcggccat | tttccaccat | gatattcggc | aagcaggcat | 780 |
| cgccatgggt | cacgacgaga | tcctcgccgt | cgggcatgcg | cgccttgagc | ctggcgaaca | 840 |
| gttcggctgg | cgcgagcccc | tgatgctctt | cgtccagatc | atcctgatcg | acaagaccgg | 900 |
| cttccatccg | agtacgtgct | cgctcgatgc | gatgtttcgc | ttggtggtcg | aatgggcagg | 960 |
| tagccggatc | aagcgtatgc | agccgccgca | ttgcatcagc | catgatggat | actttctcgg | 1020 |
| caggagcaag | gtgagatgac | aggagatcct | gccccggcac | ttcgcccaat | agcagccagt | 1080 |
| cccttcccgc | ttcagtgaca | acgtcgagca | cagctgcgca | aggaacgccc | gtcgtggcca | 1140 |
| gccacgatag | ccgcgctgcc | tcgtcctgca | gttcattcag | gcaccggac | aggtcggtct | 1200 |
| tgacaaaaag | aaccgggcgc | ccctgcgctg | acagccggaa | cacggcggca | tcagagcagc | 1260 |
| cgatcgtctg | ttgtgcccag | tcatagccga | atagcctctc | cacccaagcg | gccggagaac | 1320 |
| ctgcgtgcaa | tccatcttgt | tcaatggccg | atcccatggt | ttagttcctc | accttgtcgt | 1380 |
| attatactat | gccgatatac | tatgccgatg | attaattgtc | aacacgtgct | gctgcaggtc | 1440 |
| gaaaggcccg | gagatgagga | agaggagaac | agcgcggcag | acgtgcgctt | ttgaagcgtg | 1500 |
| cagaatgccg | ggcctccgga | ggaccttcgg | gcgcccgccc | cgcccctgag | cccgcccctg | 1560 |
| agcccgcccc | cggacccacc | ccttcccagc | ctctgagccc | agaaagcgaa | ggagcaaagc | 1620 |
| tgctattggc | cgctgcccca | aaggcctacc | cgcttccatt | gctcagcggt | gctgtccatc | 1680 |
| tgcacgagac | tagtgagacg | tgctacttcc | atttgtcacg | tcctgcacga | cgcgagctgc | 1740 |
| ggggcggggg | ggaacttcct | gactagggga | ggagtagaag | gtggcgcgac | ggggccacca | 1800 |
| aagaacggag | ccggttggcg | cctaccggtg | gatgtggaat | gtgtgcgagg | ccagaggcca | 1860 |
| cttgtgtagc | gccaagtgcc | cagcggggct | gctaaagcgc | atgctccaga | ctgccttggg | 1920 |
| aaaagcgcct | cccctacccg | gtagaatata | acttcgtata | atgtatgcta | tacgaagtta | 1980 |
| tgcggcccta | gtgatttagg | ctcatagaga | caaaggtcca | gataaaggtg | tcctgggatt | 2040 |
| tccaggcttt | gagctgtaat | tttctgggct | atgtgaagac | agggaaaggc | tagggaaaac | 2100 |

```
ggagtcgaag ctgtcccctt tgactcagaa ctctgcaacc ccttctccca tcctgaatac    2160
tattcttggt aagtgtctta gctgtctcta gcaagaccta atggagttgt ctggagctga    2220
gaaaggggtt aggggaaccg tgtgggtaaa tgacaggcac caacggtgtt tccagccagg    2280
gttgtttgag ggccaggtac ccagtgccta ccattcaagc agtacgctcc ctcccgcagt    2340
ggtggcggtc tgaggagacg caggatttgg ggccggggcc cccgaatccc acggggccgt    2400
cccatcacgt gagtctgaga tcggaggacc cttccggaga ggacgatgag agggacgtga    2460
cctgtgcgtg ggacccggat cttttcctta caaactttcc aggttccgag tctcccggca    2520
cttcccggac ctgtgccctg cgcccagcg tggggccagt ggcacagttc gagccgcctg    2580
agtctctggg cgcctatgcg ggtggcccag ggttggtgac tgggcctttg ggctccgagg    2640
agcacacaag ctgggcgcac ccgactccga gaccccagc ccctgaaccc ttcgtggccc    2700
ctgccctggc cccgggactc gctcccaagg ctcagccctc gtactccgac tcgcgagcgg    2760
gctccgtagg gggcttcttc ccgcgggcgg ggcttgcggt gcccgcagct ccaggcgccc    2820
cctatgggct gctgtcggga taccccgcgc tgtaccccgc gccacagtac caaggccact    2880
tccagctctt tcgcgggctc gcggcgcctt ctgctggtcc cacggcgccc ccttccttct    2940
tgaattgtct gggacctggg actgtggcca cagaactcgg ggccactgcg atcgccggag    3000
acgcaggctt gtccccggga actgcgccgc ccaaacgcag ccggcgaact ttggcaccta    3060
agaggcaggc ggcacatacg tgcgggcacg aaggctgcgg gaagagctac accaagagct    3120
cgcacctcaa ggcgcacctg cgcacgcaca cgggtaaggg cggggccaga cgggcggggg    3180
cggggcggga gccgctagtg aacgaaggga ggggccggag ggtagtcaga ggcgtggcta    3240
aaggcggccc cagttctagg ggtcgtgaag accgcacctg agacactggg tcaagtctag    3300
aaggggcgat tccagaccca aatgggctaa tacaaacact cggaggcag aggcaggtgg    3360 atagcagtga cttcgaggcc atttgggcta ttatagcgag tttcagcagc ctgagctact    3420
tagtgagatc ctggttcata aataaatagg tgtaacagag gacctgggga acactttggg    3480
gacttcggtg ttagaagtgg atgtgtaagg cctgggttag agatgggaga agaaactaga    3540
ggggtgaacc cgaaaggtac aagcttggaa tgccagagct caggatatag ccagtattta    3600
catgcatgct cgagctggaa ccatctggga tcaggaggtt gagacactca agtaaaatca    3660
gtttcagggg caactgacag aggtcccaga gttaagaaaa aagagaagg gggctggaga    3720 gatggctcag tggttaagag cactgactgc tcttccagag gtcctgagtt aaatcccag    3780 caccacatgg tggctcacaa ccatctgtaa tgggatccga tgccctcttc tggtgtgact    3840
gaagacagct acagtgtact tacatataat aaataaataa attaaaaaa aaagaaaga    3900 aagaaaaaag aaaagaagag aaggaaatgc tgagagacag ggcctagaaa gagaaacggg    3960
gtcatcccag gactggaaga cagctgaggg tctcccaagc atggcagggc acgcaacagg    4020
ctgtaacagg aagagaggga atcaccagag acagggcctt gaacactggg gtggatttct    4080
gggcttgaac caagttgagg aacaagactg gatatcatcg ggaggctctg ccagagcaag    4140
aaatagctgc aacgcggaga acaaagaacg aaggtgcagc cacataaaaa ggcagggaac    4200
tagcacaccg gaagtgggat aggagaccgg aagtgagaaa actgcaggat tgcagctgta    4260
gatacagaaa aggattgagt cacagaaggc aggattatgt gacccttttaa ctgtgtgggc    4320 taggtatgtc ctaagacttg gctctacttc atcaagggtg caaactggag ctgggttgct    4380
tggagggtgg tacttacagc tccctgtcct tcaggagaga agcctatgc ctgctcctgg    4440 gacggctgtg actggaggtt cgctcgctca gacgaactga cgcgccacta ccggaagcac    4500
```

```
actggacatc gtcccttctg ctgtggcctc tgcccacgtg cttttttcacg ctctgaccac    4560 ttagctctgc acatgaagcg tcacctctga gtgatcctgc acaaggactg gggatgaaat    4620
aagagtggat ccaaggaccg tatcccaaaa gatgggccat tatatagtcc tacccagatc    4680
aaaaactgac cagaagacca tacaaaggag ccttcaggac aaacctcaca tgtcctcagg    4740
gagccccaca catggcccca cagacccagc aatatagacc accagataaa tcaactcaaa    4800
tggaccccta gaccagagga gtgaccctgt gtcctggacg cagatggact ggggtgagat    4860
ttcctaagat ctagaaggga gcttcacact gtgcccatct gctaggattg ttgtcgttac    4920
tataaaaatt tcccatataa aaccag                                         4946

<210> SEQ ID NO 9
<211> LENGTH: 2782
<212> TYPE: DNA
<213> ORGANISM: Homo sapiens

<400> SEQUENCE: 9
tcagagttca cgaggcagcc gaggaagagg aggcttgagg cccagggtgg gcaccagcca      60
gccatggcca cagccgagac cgccttgccc tccatcagca cactgaccgc cctgggcccc     120
ttcccggaca cacaggatga cttcctcaag gtggggccta aaggtgggg tctaggtggg      180 ctggctggaa tccagggcca cagtcacaga tcttggggtc cagacctgca tcttgacctg     240
aaatcaagag acttaaccag gactgaggta cgctcagtcc aggagaggag atctcagctt     300
agtctggcag ggggtgagga gggtggtcta ggggtttgag gttctaagtg tgatctattt     360
cggtaataga aaacgaaggt agcctgggca acatggtgaa accctatctc tacaaaaaat     420
accaaaaaca ttaggccagg catgggggcg tgtgcctgta gtcccaggta ctccgtaggc     480
tgatgcagga ggatcattag agcccaggag attaaggata cagtgagctg caccactgca     540
ctccagcctg gcaaaagag taagacccta tctcaagaaa aaaaaaaaa aaaggaacg        600 agatctaggc tcacagacaa tcttccagat atcagcggga aatgatgagt gtgtctgggg     660
gacatccaaa atttcggaat taatcttgtt ttgggagaca gggaaggaga gggatgttct     720
gggggaaaac taagtcaagg ctggcatcct ctcccccgtc ccctgccagt tttccatctc     780
cagcagctct gctaccccctt cccccatccc cgagtgtggt tccagatagt ggaagtctta     840
tctcctgtct ccagccagac ctgatcggtt tctgtccctg gagctggggg gggagcgggg     900
agaggggcgg ttagaggggc agtgttgggg aagtgggaca gacagacagg caaacaagac     960 cccttttccaa agcctctgcg tcagagtgtc cagcccgcga tgtccctggg cagggcaccc    1020
cagtgtccac cgaacctcga gctgcctgct ccctcccgca gtggtggcgc tccgaagagg    1080
cgcaggacat gggcccgggt cctcctgacc ccacggagcc gcccctccac gtgaagtctg    1140
aggaccagcc cggggaggaa gaggacgatg agagggggcgc ggacgccacc tgggacctgg    1200
atctcctcct caccaacttc tcgggcccgg agccggtgg cgcgcccag acctgcgctc       1260 tggcgcccag cgaggcctcc ggggcgcaat atccgccgcc gcccgagact ctgggcgcat    1320
atgctggcgg cccgggggctg gtggctggc ttttgggttc ggaggatcac tcgggttggg      1380
tgcgccctgc cctgcgagcc cgggctcccg acgccttcgt gggcccagcc ctggctccag    1440
ccccggcccc cgagcccaag gcgctggcgc tgcaaccggt gtacccgggg cccggcgccg    1500
gctcctcggg tggctacttc ccgcggaccg ggctttcagt gcctgcggcg tcgggcgccc    1560
cctacgggct actgtccggg tacccgcgca tgtacccggc gcctcagtac caagggcact    1620
```

-continued

| | |
|---|---:|
| tccagctctt ccgcgggctc cagggacccg cgcccggtcc cgccacgtcc ccctccttcc | 1680 |
| tgagttgttt gggacccggg acggtgggca ctggactcgg ggggactgca gaggatccag | 1740 |
| gtgtgatagc cgagaccgcg ccatccaagc gaggccgacg ttcgtgggcg cgcaagaggc | 1800 |
| aggcagcgca cacgtgcgcg cacccgggtt gcggcaagag ctacaccaag agctcccacc | 1860 |
| tgaaggcgca tctgcgcacg cacacaggtg aggggcggg gccccggaca tgagaaaggg | 1920 |
| cgcggcgccc gctgtagtta caggggaaga agggttgcag agggcgggac ttggacttgg | 1980 |
| ctggcctctg agagtgagtg cctccttaaa ttttgtgccc taggggcctc actttgttca | 2040 |
| tcctagtccc agcccaggct gagtaaaggg gtgtggccag atgcagggga cccgggggaca | 2100 |
| tgactgggca gacagtggcg cttatggctt ccttgtcccc taggggagaa gccatacgcc | 2160 |
| tgcacgtggg aaggctgcgg ctggagattc gcgcgctcgg acgagctgac ccgccactac | 2220 |
| cggaaacaca cggggcagcg cccccttccgc tgccagctct gcccacgtgc ttttttcgcgc | 2280 |
| tctgaccacc tggccttgca catgaagcgc cacctttgag ccctgccctg gcacttggac | 2340 |
| tctcctagtg actggggatg ggacaagaag cctgttttggt ggtctcttca cacggacgcg | 2400 |
| cgtgacacaa tgctgggtgg ttttcccacg aatggaccct ctcctggact cgcgttccca | 2460 |
| aagatccacc caaatatcaa acacggaccc atagacagcc ctgggggagc ctcttacgga | 2520 |
| aaatccgaca agccttcagc cacagggagc cacacagaga tgtccaaact gtcgtgcaaa | 2580 |
| cccagtgaga cagaccgcca aataaacgga ctcagtggac actcagacca gctcccagat | 2640 |
| ggccctggac agcaggagag ggtgtgggat gaggcttccc agagaccctg ggtctagaaa | 2700 |
| gcggctcctg aaggtccctt attgtggctg atattaactg tcaatggtta tgggtcctat | 2760 |
| aaaaatgccc ctcccagata aa | 2782 |

<210> SEQ ID NO 10
<211> LENGTH: 3368
<212> TYPE: DNA
<213> ORGANISM: Mus musculus

<400> SEQUENCE: 10

| | |
|---|---:|
| gtgggcagac aggagccctc caagaaactt tcctagcctc atagcccatg aggcagaaga | 60 |
| gagagaggag gcctgaggtc cagggtggac accagccagc catggcctca gctgagactg | 120 |
| tcttaccctc catcagtaca ctcaccaccc tgggacagtt cctggacacc caggaggact | 180 |
| tcctcaaggt ggggccagtg tgagtgtgtg ggaggggca ggtggtcttg catagggcat | 240 |
| agtgcttagg ggtggggcgt ctatcttact ttaatatcct ctgctctgtt ttttgggggt | 300 |
| ggaggagtgg gagagcctct gagccttgtt tgggggagat gttctagggg tctgagatca | 360 |
| aggtgaggcc tatttctcca acaggaagca gaattctaag ctctatatct taagagacta | 420 |
| ggctcataga gacaaaggtc cagataaagg tgtcctggga tttccaggct ttgagctgta | 480 |
| attttctggg ctatgtgaag acagggaaag gctagggaaa acggagtcga agctgtcccc | 540 |
| tttgactcag aactctgcaa ccccttctcc catcctgaat actattcttg gtaagtgtct | 600 |
| tagctgtctc tagcaagacc taatggagtt gtctggagct gagaaagggg ttaggggaac | 660 |
| cgtgtgggta aatgacaggc accaacgtgt tttccagcca gggttgtttg agggccaggt | 720 |
| acccagtgcc taccattcaa gcagtacgct ccctcccgca gtggtggcgg tctgaggaga | 780 |
| cgcaggattt ggggccgggg cccccgaatc ccacggggcc gtccatcac gtgagtctga | 840 |
| aatcggagga cccttccgga gaggacgatg agagggacgt gacctgtgcg tgggacccgg | 900 |
| atcttttcct tacaaacttt ccaggttccg agtctcccgg cacttccgg acctgtgccc | 960 |

```
tggcgcccag cgtggggcca gtggcacagt tcgagccgcc tgagtctctg ggcgcctatg   1020
cgggtggccc agggttggtg actgggcctt tgggctccga ggagcacaca agctgggcgc   1080
acccgactcc gagaccccca gcccctgaac ccttcgtggc ccctgccctg ccccgggac    1140 tcgctcccaa ggctcagccc tcgtactccg actcgcgagc gggctccgta gggggcttct   1200
tcccgcgggc ggggcttgcg gtgcccgcag ctccaggcgc ccctatggg ctgctgtcgg    1260 gataccccgc gctgtacccc gcgccacagt accaaggcca cttccagctc tttcgcgggc   1320
tcgcggcgcc ttctgctggt cccacggcgc ccccttcctt cttgaattgt ctgggacctg   1380
ggactgtggc cacagaactc ggggccactg cgatcgccgg agacgcaggc ttgtccccgg   1440
gaactgcgcc gcccaaacgc agccggcgaa ctttggcacc taagaggcag gcggcacata   1500
cgtgcgggca cgaaggctgc gggaagagct acaccaagag ctcgcacctc aaggcgcacc   1560
tgcgcacgca cacgggtaag ggcggggcca gacgggcggg ggcggggcgg gagccgctag   1620
tgaacgaagg gaggggccgg agggtagtca gaggcgtggc taaaggcggc cccagttcta   1680
ggggtcgtga agaccgcacc tgagacactg ggtcaagtct agaaggggcg attccagacc   1740
caaatgggct aatacaaaca ctcgggaggc agaggcaggt ggatagcagt gacttcgagg   1800
ccatttgggc tattatagcg agtttcagca gcctgagcta cttagtgaga tcctggttca   1860
taaataaata ggtgtaacag aggacctggg gaacactttg gggacttcgg tgttagaagt   1920
ggatgtgtaa ggcctgggtt agagatggga gaagaaacta gaggggtgaa cccgaaaggt   1980
acaagcttgg aatgccagag ctcaggatat agccagtatt tacatgcatg ctcgagctgg   2040
aaccatctgg gatcaggagg ttgagacact caagtaaaat cagtttcagg ggcaactgac   2100
agaggtccca gagttaagaa agaagagaa ggggctgga gagatggctc agtggttaag    2160
agcactgact gctcttccag aggtcctgag tttaaatccc agcaccacat ggtggctcac   2220
aaccatctgt aatgggatcc gatgccctct tctggtgtga ctgaagacag ctacagtgta   2280
cttacatata ataaataaat aaattaaaaa aaaaagaaa gaagaaaaa agaaaagaag    2340 agaaggaaat gctgagagac agggcctaga aagagaaacg gggtcatccc aggactggaa   2400
gacagctgag ggtctcccaa gcatggcagg gcacgcaaca ggctgtaaca ggaagagagg   2460
gaatcaccag agacagggcc ttgaacactg gggtggattt ctgggcttga accaagttga   2520
ggaacaagac tggatatcat cgggaggctc tgccagagca agaaatagct gcaacgcgga   2580
gaacaaagaa cgaaggtgca gccacataaa aaggcaggga actagcacac cggaagtggg   2640
ataggagacc ggaagtgaga aaactgcagg attgcagctg tagatacaga aaaggattga   2700
gtcacagaag gcaggattat gtgacctttt aactgtgtgg gctaggtatg tcctaagact   2760
tggctctact tcatcaaggg tgcaaactgg agctgggttg cttggagggt ggtacttaca   2820
gctccctgtc cttcaggaga gaagccttat gcctgctcct gggacggctg tgactggagg   2880
ttcgctcgct cagacgaact gacgcgccac taccggaagc acactggaca tcgtcccttc   2940
tgctgtggcc tctgcccacg tgcttttca cgctctgacc acttagctct gcacatgaag    3000
cgtcacctct gagtgatcct gcacaaggac tggggatgaa ataagagtgg atccaaggac   3060
cgtatcccaa aagatgggcc attatatagt cctacccaga tcaaaaactg accagaagac   3120
catacaaagg agccttcagg acaaacctca catgtcctca gggagcccca cacatggccc   3180
cacagaccca gcaatataga ccaccagata aatcaactca aatggacccc tagaccagag   3240
gagtgaccct gtgtcctgga cgcagatgga ctggggtgag atttcctaag atctagaagg   3300
```

```
gagcttcaca ctgtgcccat ctgctaggat tgttgtcgtt actataaaaa tttcccatat    3360
aaaaccag                                                             3368
```